US010022357B2

(12) United States Patent
Rogers et al.

(10) Patent No.: US 10,022,357 B2
(45) Date of Patent: Jul. 17, 2018

(54) AMYLOID PRECURSOR PROTEIN MRNA BLOCKERS FOR TREATING DOWN SYNDROME AND ALZHEIMER'S DISEASE

(71) Applicants: THE GENERAL HOSPITAL CORPORATION, Boston, MA (US); THE BROAD INSTITUTE, INC., Cambridge, MA (US)

(72) Inventors: Jack T Rogers, Arlington, MA (US); Xudong Huang, Andover, MA (US); James Spoonamore, Somerville, MA (US)

(73) Assignees: THE GENERAL HOSPITAL CORPORATION, Boston, MA (US); THE BROAD INSTITUTE, INC., Cambridge, MA (US)

(*) Notice: Subject to any disclaimer, the term of this patent is extended or adjusted under 35 U.S.C. 154(b) by 0 days.

(21) Appl. No.: 14/787,873

(22) PCT Filed: Apr. 29, 2014

(86) PCT No.: PCT/US2014/035860
§ 371 (c)(1),
(2) Date: Oct. 29, 2015

(87) PCT Pub. No.: WO2014/179303
PCT Pub. Date: Nov. 6, 2014

(65) Prior Publication Data
US 2016/0074367 A1    Mar. 17, 2016

Related U.S. Application Data

(60) Provisional application No. 61/817,081, filed on Apr. 29, 2013.

(51) Int. Cl.
*A61K 31/4184*    (2006.01)
*A61K 31/416*    (2006.01)
*A61K 31/4439*    (2006.01)

(52) U.S. Cl.
CPC ........ *A61K 31/4184* (2013.01); *A61K 31/416* (2013.01); *A61K 31/4439* (2013.01)

(58) Field of Classification Search
CPC .................................................. A61K 31/4184
USPC ........................................................ 514/249
See application file for complete search history.

(56) References Cited

U.S. PATENT DOCUMENTS

2012/0082623 A1* 4/2012 Kottmann .......... A61K 31/4747 424/9.2
2013/0035342 A1    2/2013 Masliah et al.

FOREIGN PATENT DOCUMENTS

WO    2010/117727 A2    10/2010

OTHER PUBLICATIONS

Cui, Nuclear Medicine and Biology 38 (2011) 313-320.*
Zhuang et al., Structure-Activity Relationship of Imidazo[1,2-a]pyridines as Ligands for Detecting beta-Amyloid Plaques in the Brain, 2003, J. Med. Chem., 46, pp. 237-243 (Year: 2003).*
Shaw et al., "Phenserine regulates translation of β-amyloid precursor protein mRNA by a putative interleukin-1 responsive element, a target for drug development", PNAS 98(13):7605-7610 (2001).
Singh et al., "Prion Protein (PrP) Knock-Out Mice Show Altered Iron Metabolism: A Functional Role for PrP in Iron Uptake and Transport", PLoS One 4(7): e6115 (2009). (14 pages).
Singh et al., "Abnormal Brain Iron Homeostasis in Human and Animal Prion Disorders", PLoS Pathogens 5(3): e1000336 (2009). (16 pages).
Skibo et al., "Structure-Activity Studies of Benzimidazole-Based DNA-Cleaving Agents. Comparison of Benzimidazole, Pyrrolobenzimidazole, and Tetrahydropyridobenzimidazole Analogues", Journal of Medicinal Chemistry 37:78-92 (1994).
Smith et al., "Excess brain protein oxidation and enzyme dysfunction in normal aging and in Alzheimer disease", Proc. Natl. Acad. Sci. USA 88:10540-10543 (1991).
Stys et al., "Iron Regulatory Protein 1 Outcompetes Iron Regulatory Protein 2 in Regulating Cellular Iron Homeostasis in Response to Nitric Oxide", The Journal of Biological Chemistry 286(26)22846-22854 (2011).
Theuns et al., "Promoter Mutations That Increase Amyloid Precursor-Protein Expression Are Associated with Alzheimer Disease", The American Journal of Human Genetics 78:936-946 (2006).
Tibodeau et al., "The up-regulation of ferritin expression using a small-molecule ligand to the native mRNA", PNAS 103(2):253-257 (2006).
Tucker et al., "RNA Therapeutics Directed to the Non Coding Regions of APP mRNA, In Vivo Anti-Amyloid Efficacy of Paroxetine, Erythromycin, and N-acetyl cysteine", Current Alzheimer Research 3(3)221-227 (2006).
Utsuki et al., "Identification of Novel Small Molecule Inhibitors of Amyloid Precursor Protein Synthesis as a Route to Lower Alzheimer's Disease Amyloid-β Peptide", The Journal of Pharmacology and Experimental Therapeutics 318 (2):855-862 (2006).
Varvel et al., "Aβ Oligomers Induce Neuronal Cell Cycle Events in Alzheimer's Disease", J Neurosci. 28 (43):10786-10793 (2008).
Venti et al., "The Integrated Role of Desferrioxamine and Phenserine Targeted to an Iron-Responsive Element in the APP-mRNA 5'-Untranslated Region", Annals New York Academy of Science 1035:34-48 (2004).

(Continued)

*Primary Examiner* — Kortney L. Klinkel
*Assistant Examiner* — Tori Strong
(74) *Attorney, Agent, or Firm* — Nixon Peabody LLP; David S. Resnick; Ravinderjit Braich

(57) ABSTRACT

The present disclosure relates to methods for treating a neurodegenerative disorder by administering an effective amount of an agent that inhibits or reduces translation of amyloid precursor protein. In some embodiments, the neurodegenerative disorder is Alzheimer's disease or Down syndrome. Also disclosed are methods for decreasing amyloid-beta production in a subject's brain. Further disclosed is a method for restoring or maintaining iron homeostasis in a subject's brain.

14 Claims, 20 Drawing Sheets

(56) References Cited

OTHER PUBLICATIONS

Werstuck et al., "Controlling Gene Expression in Living Cells Through Small Molecule-RNA Interactions", Science 282:296-298 (1998).
Wisniewski et al., "Acceleration of Alzheimer's Fibril Formation by Apolipoprotein E In Vitro", American Journal of Pathology 145(5):1030-1035 (1994).
Wolk et al., "Update on Amyloid Imaging: From Healthy Aging to Alzheimer's Disease", Curr Neurol Neurosci Rep 9(5):345-352 (2009).
Yi et al., "Disposition and Metabolism of Semagacestat, a γ-Secretase Inhibitor, in Humans", Drug Metabolism and Disposition 38(4):554-565 (2010).
Adlard et al., "Rapid Restoration of Cognition in Alzheimer's Transgenic Mice with 8-Hydroxy Quinoline Analogs Is Associated with Decreased Interstitial Aβ", Neuron, 59:43-55 (2008).
Bandyopadhyay et al., "A High-Throughput Drug Screen Targeted to the 5'Untranslated Region of Alzheimer Amyloid Rrecursor Protein mRNA", Journal of Biomolecular Screening 11(5):469-480 (2006).
Bandyopadhyay et al., "Novel drug targets based on metallobiology of Alzheimer's disease", Expert Opinion on Therapeutic Targets 14(11):1177-1197 (2010).
Bandyopadhyay et al., "Novel 5' Untranslated Region Directed Blockers of Iron-Regulatory Protein-1 Dependent Amyloid Precursor Protein Translation: Implications for Down Syndrome and Alzheimer's Disease", PLOS ONE 8(7): e65978 (2013). (14 pages).
Butterfield, "Oxidative Stress in Alzheimer Disease: Synergy Between the Butterfield and Markesbery Laboratories", Neuromolecular Med. 13(1):19-22 (2011).
Cho et al., "Selective Translational Control of the Alzheimer Amyloid Precursor Protein Transcript by Iron Regulatory Protein-1", The Journal of Biological Chemistry 285(41):31217-31232 (2010).
Darnell et al., "FMRP Stalls Ribosomal Translocation on mRNAs Linked to Synaptic Function and Autism", Cell 146:247-261 (2011).
De Meyer et al., "Diagnosis-Independent Alzheimer Disease Biomarker Signature in Cognitively Normal Elderly People", Arch Neurol. 67(8):949-956 (2010).
Donahue et al., "Stabilization of the Tau Exon 10 Stem Loop Alters Pre-mRNA Splicing", The Journal of Biological Chemistry 281(33):23302-23306 (2006).
Donahue et al., "Identification of Tau Stem Loop RNA Stabilizers", Journal of Biomolecular Screening 12(6):789-799 (2007).
Doody et al., "A Phase 3 Trial of Semagacestat for Treatment of Alzheimer's Disease", The New England Journal of Medicine 369(4):341-350 (2013).
Duce et al., "An Iron-export ferroxidase activity of β-amyloid protein precursor is inhibited by zinc in Alzheimer's Disease", Cell 142(6):857-867 (2010).
Friedlich et al., "The 5'-untranslated region of Parkinson's disease α-synuclein messengerRNA contains a predicted Iron responsive element", Molecular Psychiatry 12:222-223 (2007).
Gilman et al., "p53 is Present in Synapses Where it Mediates Mitochondrial Dysfunction and Synaptic Degeneration in Response to DNA Damage, and Oxidative and Excitotoxic Insults", NeuroMolecular Medicine 3:159-172 (2003).
Goforth et al., "Multiple determinants within iron-responsive elements dictate iron regulatory protein binding and regulatory hierarchy", RNA 16:154-169 (2010).
Granic et al., "Alzheimer Aβ Peptide Induces Chromosome Mis-Segregation and Aneuploidy, Including Trisomy 21: Requirement for Tau and APP", Molecular Biology of the Cell 21:511-520 (2010).
Hamy et al., "An inhibitor of the Tat/TAR RNA interaction that effectively suppresses HIV-1 replication", Proc. Natl. Acad. Sci. USA 94:3548-3553 (1997).
Hooli et al., "Role of common and rare APP DNA sequence variants in Alzheimer disease", Neurology 78:1250-1257 (2012).

Iijima et al., "Tau Ser262 phosphorylation is critical for Aβ42-induced tau toxicity in a transgenic *Drosophila* model of Alzheimer's disease", Human Molecular Genetics 19(15):2947-2957 (2010).
Jalava et al., "Mutation at the position 2058 of the 23S rRNA as a cause of macrolide resistance in *Streptococcus pyogenes*", Annals of Clinical Microbiology and Antimicrobials 3:5 (2004). (6 pages).
Jonsson et al., "A Mutation in APP protects against Alzheimer's disease and age-related cognitive decline", Nature 488:96-99 (2012).
Komarova et al., "p53 Inhibitor Pifithrin α Can Suppress Heat Shock and Glucocorticoid Signaling Pathways", The Journal of Biological Chemistry 278(18):15465-15468 (2003).
Kuo et al., "Extensive enteric nervous system abnormalities in mice transgenic for artificial chromosomes containing Parkinson disease-associated α-synuclein gene mutations precede central nervous system changes", Human Molecular Genetics 19(9):1633-1650 (2010).
Kurogi et al., "Discovery of Novel Mesangial Cell Proliferation Inhibitors Using a Three-Dimensional Database Searching Method", Journal of Medicinal Chemistry 44:2304-2307 (2001).
Kwon et al., "Apolipoprotein E Polymorphism and Age at Onset of Alzheimer's Disease in a Quadriethnic Sample", Dementia and Geriatric Cognitive Disorders 30:486-491 (2010).
Lahiri et al., "The Experimental Alzheimer's Disease Drug Posiphen [(+)-Phenserine] Lowers Amyloid-β Peptide Levels in Cell Culture and Mice", The Journal of Pharmacology and Experimental Therapeutics 320(1):386-396 (2007).
Lancaster et al., "Initiation factor-independent translation mediated by the hepatitis C virus internal ribosome entry site", RNA 12:894-902 (2006).
Li et al., "Toward Structural Elucidation of the γ-Secretase Complex", Structure 17:326-334 (2009).
Li et al., "Virus-like Peptide Vaccines Against Aβ N-terminal or C-terminal Domains Reduce Amyloid Deposition in APP Transgenic Mice without Addition of Adjuvant", J Neuroimmune Pharmacol 5:133-142 (2010).
Lovell et al., "Copper, iron and zinc in Alzheimer's disease senile plaques", Journal of the Neurological Sciences 158:47-52 (1998).
Maccecchini et al., "Posiphen lowers amyloid precursor protein and amyloid β as well as acetylcholinesterase evels in culture, animals and humans", Alzheimer's & Dementia:The Journal of the Alzheimer's Association 5(4):P247-P248 (2009).
Mackenzie et al., "TDP-43 and FUS in amyotrophic lateral sclerosis and frontotemporal dementia", Lancet Neurol 9:995-1007 (2010).
Mathis et al., "Synthesis and Evaluation of 11C-Labeled 6-Substituted 2-Arylbenzothiazoles as Amyloid Imaging Agents", Journal of Medicinal Chemistry 46:2740-2754 (2003).
McNaughton et al., "Duplication of amyloid precursor protein (APP), but not prion protein (PRNP) gene is a significant cause of early onset dementia in a large UK series", Neurobiology of Aging 33:426.e13-426.e21 (2012). (9 pages).
Mikkilineni et al., "The Anticholinesterase Phenserine and its Enantiomer Posiphen as 5' Untranslated-Region-Directed Translation Blockers of the Parkinson's Alpha Synuclein Expression", Parkinson's Disease 2012:1-13 (2012).
Morales et al., "Molecular Cross Talk between Misfolded Proteins in Animal Models of Alzheimer's and Prion Diseases", The Journal of Neuroscience 30(13):4528-4535 (2010).
Morse et al., "FDA-Preapproved Drugs Targeted to the Translational Regulation and Processing of the Amyloid Precursor Protein", Journal of Molecular Neuroscience 24:129-136 (2004).
Nilsson et al., "Cognitive impairment in PDAPP mice depends on ApoE and ACT-catalyzed amyloid formation", Neurobiology of Aging 25:1153-1167 (2004).
Osenkowski et al., "Direct and Potent Regulation of γ-Secretase by Its Lipid Microenvironment", The Journal of Biological Chemistry 283(33):22529-22540 (2008).
Parvathy et al., "Atorvastatin-induced activation of Alzheimer's α secretase is resistant to standard inhibitors of protein phosphorylation-regulated ectodomain shedding", Journal of Neurochemistry 90:1005-1010 (2004).

(56) References Cited

OTHER PUBLICATIONS

Payton et al., "Drug Discovery Targeted to the Alzheimer's APP mRNA 5'-untranslated Region: The Action of Paroxetine and Dimercaptopropanol", Journal of Molecular Neuroscience 20:267-275 (2003).

Perry et al., "Is Oxidative Damage the Fundamental Pathogenic Mechanism of Alzheimer's and Other Neurodegenerative Diseases?", Free Radical Biology & Medicine 33(11):1475-1479 (2002).

Ray et al., "Molecular and immunocytochemical characterization of primary neuronal cultures from adult rat brain: differential expression of neuronal and glial protein markers", J Neurosci Methods 184(2):294-302 (2009).

Rogers et al., "Alzheimer's Disease Drug Discovery Targeted to the APP mRNA 5'Untranslated Region", Journal of Molecular Neuroscience, 19:77-82 (2002).

Rogers et al., "An Iron-responsive Element Type II in the 5'-Untranslated Region of the Alzheimer's Amyloid Precursor Protein Transcript", The Journal of Biological Chemistry 277(47):45518-45528 (2002).

Rogers et al., "The alpha-synuclein 5'untranslated region targeted translation blockers: anti-alpha synuclein efficacy of cardiac glycosides and Posiphen", Journal of Neural Transmission 118(3):493-507 (2011).

Rovelet-Lecrux et al., "APP locus duplication causes autosomal dominant early-onset Alzheimer disease with cerebral amyloid angiopathy", Nature Genetics 38(1):24-26 (2006).

Salehi et al,. "Increased App Expression in a Mouse Model of a Down's Syndrome Disrupts NGF Transport and Causes Cholinergic Neuron Degeneration", Neuron 51:29-42 (2006).

Salehi et al., "Restoration of Norepinephrine-Modulated Contextual Memory in a Mouse Model of Down Syndrome", Science Translational Medicine, 1(7):7ra17 (2009). (10 pages).

Schulz et al., "Evidence for DNA phosphate backbone alkylation and cleavage by pyrrolo[1,2-a]benzimidazoles: Small molecules capable of causing base-pair specific phosphodiester bond hydrolysis", Proc. Natl. Acad. Sci. USA 92:11854-11858 (1995).

* cited by examiner

| SEQ ID NO:8 | APP-IRE LOOP | | CAGAGCAAGGAC | | |
|---|---|---|---|---|---|
| SEQ ID NO:9 | 5' (65)... | GGCGGTGGCGGCGGCGGG | CAGAGCAAGGAC | GCGGGCGGATCCCACTC 3' | APP |
| SEQ ID NO:10 | 5' ... | TCGCCTGTCCTCCGAGC | CAGTC | GCTGACAGCCGCGGAG 3' | PrP VT2 |
| SEQ ID NO:11 | 5' (2)... | GAGTGGCCATTCGACGA | CAGT | GTGGTGTAAAGGAATTCATTAGCC 3' | αsyn |
| SEQ ID NO:12 | 5' (54)... | GGGGTTTCCTGCTTCAA | CAGT | GCTTGGACGGAACCCGGCGCTCGT 3' | H-Chain |
| SEQ ID NO:13 | 5' (22)... | TCTGTCTCTTGCTTCAA | CAGT | GTTTGGACGGAACAGATCCGGGGA 3' | L-Chain |
| SEQ ID NO:14 | H-Chain | IRE LOOP... | CAGTGC | | |
| SEQ ID NO:15 | 5' ... | CCGCCTGTCCTCCGAGC | CAGT | CGCTGACAGCCGGCGCCGAG 3' | PrP VT2 |
| SEQ ID NO:16 | 5' (54)... | GGGGTTTCCTGCTTCAA | CAGT | GCTTGGACGAACCCGGCGCTCGT 3' | H-Chain |
| SEQ ID NO:17 | 5' (22)... | TCTGTCTCTTGCTTCAA | CAGT | GTTTGGACGGAACAGATCCGGGGA 3' | L-Chain |

*FIG. 1C*

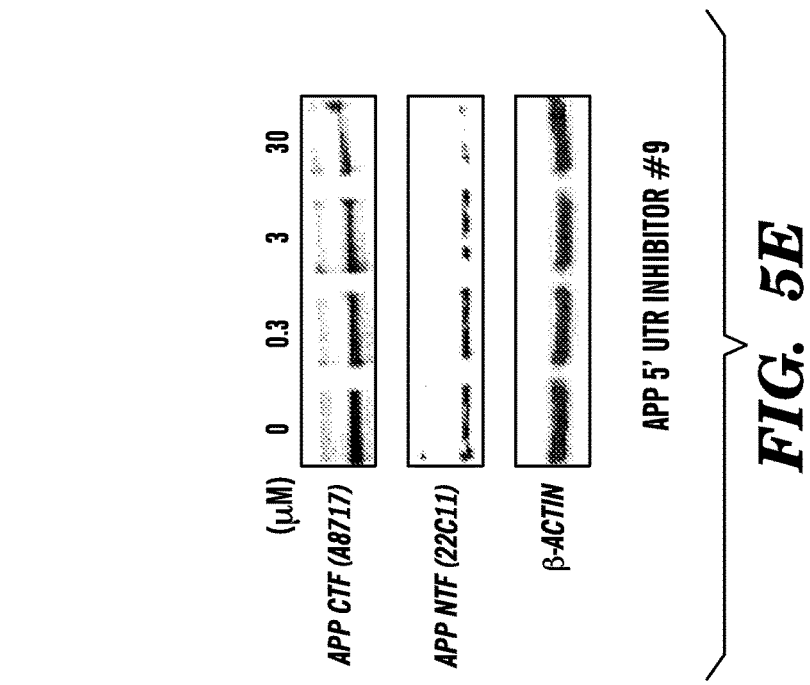
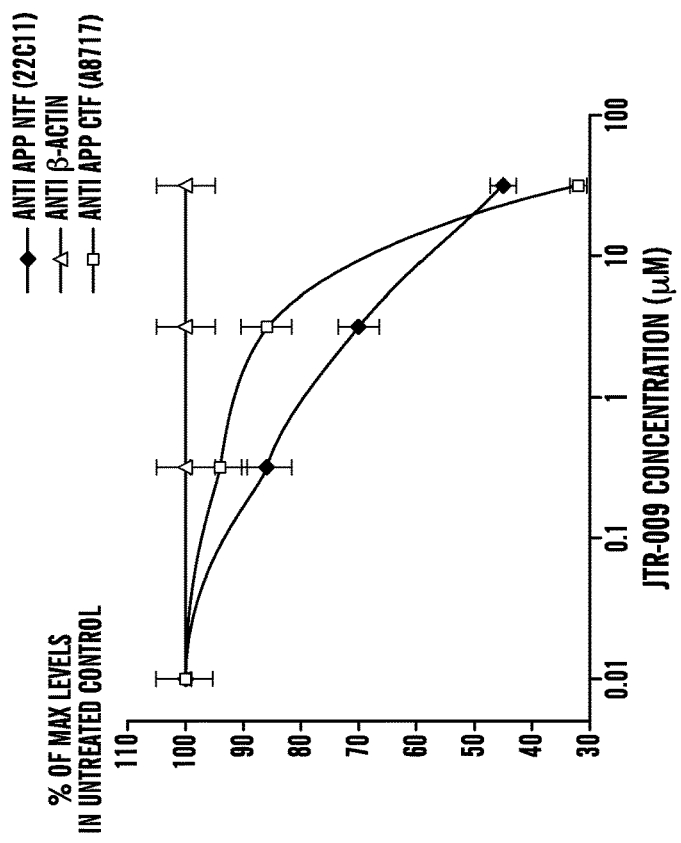
FIG. 5E
FIG. 5D

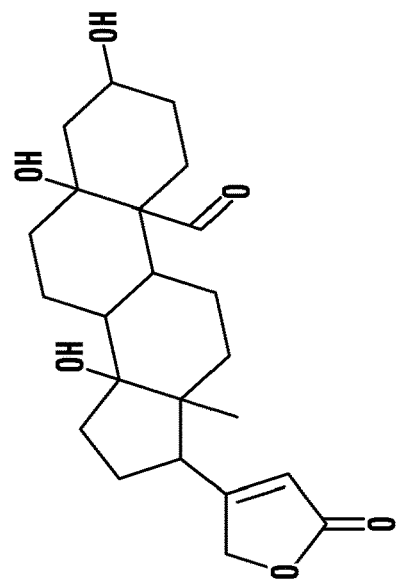
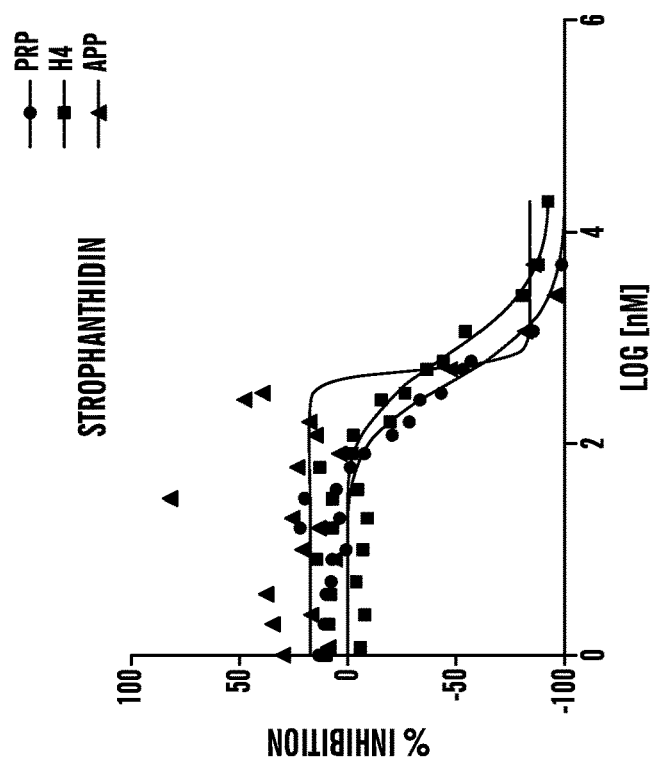
FIG. 8B
FIG. 8A

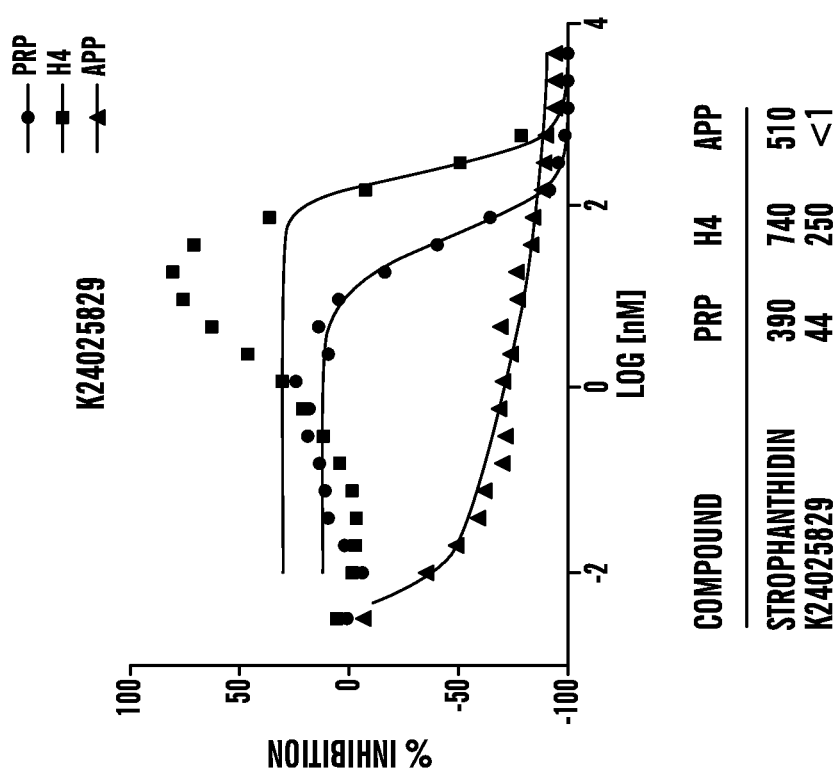
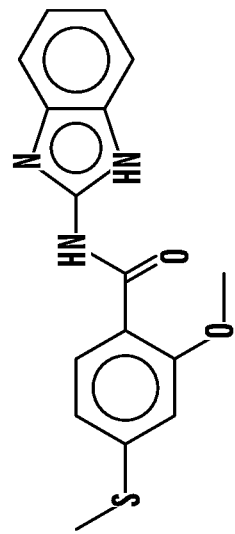
FIG. 8C
FIG. 8D

SEQUENCE LISTING

<160> NUMBER OF SEQ ID NOS: 19

<210> SEQ ID NO 1
<211> LENGTH: 57
<212> TYPE: RNA
<213> ORGANISM: Homo sapiens

<400> SEQUENCE: 1
ggggccccgg gagacggcgg cgguggcggc gcgggcagag caaggacgcg gcggauc    57

<210> SEQ ID NO 2
<211> LENGTH: 53
<212> TYPE: RNA
<213> ORGANISM: Mus musculus

<400> SEQUENCE: 2
ggggccaccg gagacggcgg cggcggcgcg gacagagcca agcgcggcgg auc    53

```
<210> SEQ ID NO 3
<211> LENGTH: 52
<212> TYPE: RNA
<213> ORGANISM: Homo sapiens

<400> SEQUENCE: 3
cccgcgcgcc gccuguccuc cgagcgaguc gcugacagcg cggcgcgcga gc            52

<210> SEQ ID NO 4
<211> LENGTH: 50
<212> TYPE: RNA
<213> ORGANISM: Homo sapiens

<400> SEQUENCE: 4
acugggagug gccauucgac gacagugugg uguaaaggaa uucacuagcc               50

<210> SEQ ID NO 5
<211> LENGTH: 52
<212> TYPE: RNA
<213> ORGANISM: Mus musculus

<400> SEQUENCE: 5
uccacgcagc cagaagucgg aaagugugga gcaaaaauac aucuuauuag cc            52

<210> SEQ ID NO 6
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6 ucgucgggu uccugcucc aagagugcuu ggacggaacc cggcgcucgu uuc             53

<210> SEQ ID NO 7
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7 gcggucugu cucuugcuuc aacaguguuu ggacggaaca gacccgggga cgc            53

<210> SEQ ID NO 8
<211> LENGTH: 12
<212> TYPE: DNA
<213> ORGANISM: Homo sapiens

<400> SEQUENCE: 8
cagagcaagg ac                                                        12

<210> SEQ ID NO 9
<211> LENGTH: 45
<212> TYPE: DNA
<213> ORGANISM: Homo sapiens

<400> SEQUENCE: 9
ggcggtggcg gcgcgggcag agcaaggacg cggcggatcc cactc                    45

<210> SEQ ID NO 10
<211> LENGTH: 45
```

<212> TYPE: DNA
<213> ORGANISM: Homo sapiens

<400> SEQUENCE: 10
tcgcctgtcc tccgagccag tcgctgacag ccgcggcgcc gcgag         45

<210> SEQ ID NO 11
<211> LENGTH: 45
<212> TYPE: DNA
<213> ORGANISM: Homo sapiens

<400> SEQUENCE: 11
gagtggccat tcgacgacag tgtggtgtaa aggaattcat tagcc         45

<210> SEQ ID NO 12
<211> LENGTH: 45
<212> TYPE: DNA
<213> ORGANISM: Homo sapiens

<400> SEQUENCE: 12
ggggtttcct gcttcaacag tgcttggacg gaacccggcg ctcgt         45

<210> SEQ ID NO 13
<211> LENGTH: 45
<212> TYPE: DNA
<213> ORGANISM: Homo sapiens

<400> SEQUENCE: 13
tctgtctctt gcttcaacag tgtttggacg gaacagatcc gggga         45

<210> SEQ ID NO 14
<211> LENGTH: 6
<212> TYPE: DNA
<213> ORGANISM: Homo sapiens

<400> SEQUENCE: 14 cagtgc         6

<210> SEQ ID NO 15
<211> LENGTH: 45
<212> TYPE: DNA
<213> ORGANISM: Homo sapiens

<400> SEQUENCE: 15
ccgcctgtcc tccgagccag tcgctgacag ccgcggcgcc gcgag         45

<210> SEQ ID NO 16
<211> LENGTH: 45
<212> TYPE: DNA
<213> ORGANISM: Homo sapiens

<400> SEQUENCE: 16
ggggtttcct gcttcaacag tgcttggacg gaacccggcg ctcgt         45

<210> SEQ ID NO 17
<211> LENGTH: 45
<212> TYPE: DNA
<213> ORGANISM: Homo sapiens

<400> SEQUENCE: 17
tctgtctctt gcttcaacag tgtttggacg gaacagatcc gggga         45

<210> SEQ ID NO 18

```
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-biotin

<400> SEQUENCE: 18
ggguuuccug cuucaacagu gcuuggacgg aacccgg                             37

<210> SEQ ID NO 19
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-biotin

<400> SEQUENCE: 19
gcgguggcgg cgcgggcaga gcaaggacgc ggcggau                             37
```

AMYLOID PRECURSOR PROTEIN MRNA BLOCKERS FOR TREATING DOWN SYNDROME AND ALZHEIMER'S DISEASE

CROSS-REFERENCE TO RELATED APPLICATION

This Application is a 35 U.S.C. § 371 National Phase Entry Application of International Application No. PCT/US14/35860 filed Apr. 29, 2014, which designates the U.S. and claims benefit under 35 U.S.C. § 119(e) of U.S. Provisional Application No. 61/817,081 filed Apr. 29, 2013, the entire contents of each of which are incorporated herein by reference in their entireties.

GOVERNMENT SUPPORT

This invention was made with government support under grant no. NS064853 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Apr. 24, 2014, is named 030258-080421-PCT_SL.txt and is 3,484 bytes in size.

TECHNICAL FIELD

The present disclosure relates generally to Down syndrome therapy and Alzheimer's disease therapy.

BACKGROUND

Over-expression of the amyloid precursor protein (APP) has been genetically proven as a direct cause of Alzheimer's disease in defined pedigrees in addition to more common APP processing mutation as that influences APP cleavage and Aβ peptide fibrilization (amyloid plaque formation). In addition, APP over-expression has been linked to Alzheimer's pathology of amyloidosis and dementia in older Down Syndrome (DS) patients. More recently genetic findings were reported that APP mutations can provide direct action to prolong life without dementia as much as other APP specific mutations at promoting neuronal death (Jonsson et al., Nature 2012, 488, 96-99).

In addition, increased levels of the metals iron, copper, zinc in the brain are associated with increased risk to accelerate the course of Alzheimer's disease (AD) (Lovell M A, et al., Neurol Sci 1998, 158: 47-52). To safely store excess iron, canonical iron-responsive elements (IREs) are the 5'UTR-specific RNA stem loops that control translation of L- and H-ferritin mRNAs (iron storage) so that the L- and H chains can assemble into this iron storage multimer. The iron-regulatory proteins (IRP1 (90 kDa) and IRP2 (105 kDa)) are the two known RNA-binding proteins that are key gatekeepers for cellular iron homeostasis because of their inducible interaction with IREs to control ferritin mRNA translation and transferrin receptor (TfR) mRNA stability (iron uptake) (Bandyopadhyay et al., Expert Opin Ther Targets 2011, 14: 1177-1197).

Consistent with the report that APP is an iron export ferroxidase (Duce J A, et al. Cell 2010, 691 142: 857-867), RNAi knockout studies showed that IRP1 binds strongly to 5'UTR sequences in the APP transcript to repress expression of the precursor (Cho H H, et al., Biol Chem 2010, 285: 31217-31232). In fact, the APP mRNA encodes an active IRE that binds with a different RNA-binding specificity to IRP1 relative to the IRE of ferritin mRNA (which interacts with IRP1 & IRP2). Thus the APP 5'UTR is a unique, highly specific drug target to identify APP (and Aβ) repressors. This model is consistent with a recent report that IRP1 outcompetes IRP2 in regulating cellular iron homeostasis in response to nitric oxide (Stys A, et al, J Biol Chem 2011, 286: 22846-22854).

The concept of repressing APP translation as a therapeutic strategy in DS and AD was proven as a novel anti-amyloid strategy as exemplified by the use of the APP 5'UTR-directed FDA drug N-acetyl-cysteine (NAC) in the TgCRND8 APP (Swe) mouse model of AD (Tucker et al., Curr Alzheimer Res. 2006, 3, 221-227). An additional benefit of limiting the APP levels may be to restore perturbations to iron homeostasis during DS since APP is over-expressed by one third on the DS trisomy chromosome 21 (Salehi A, et al., Neuron 2006, 51: 29-42). Increased APP may well alter brain iron homeostasis based on its capacity to bind ferroportin and export iron (Duce J A, et al. Cell 2010, 691142: 857-867). In this regard, mice that are trisomic for chromosome 16, the orthologue of human chromosome 21, over-express APP and are genetically shown to develop the DS phenotype because of a triplicated expression of the APP gene (Salehi A, et al., Neuron 2006, 51: 29-42; Salehi A, et al., Translational Medicine 2009, 1: 1-9).

The progression of familial Alzheimer's disease (FAD) can be the result of a genetically inherited over-expression of the APP gene or by somatically induced non-disjunction events that cause APP to be over-expressed (Granic A, et al., Mol Biol Cell 2012, 21: 511-520; Hooli B V, et al., Neurology 2012, 78: 1250-1257; Rovclet-Lecrux A, et al. Nat Genet 2006, 38: 24-26).

Thus, in addition to the altered processing of APP and other risk factors (e.g., inflammation, metal-catalyzed oxidative stress (Lovell M A, et al., Neurol Sci 1998, 158: 47-52; Perry G, et al. Free Radic Biol Med 2002, 33: 1475-1479; Smith C D, et al., Natl Acad Sci USA 1991, 88: 10540-10543; Butterfield D A, Neuromolecular Med 2012, 13: 19-22), and the increased levels of apolipoprotein-E (Kwon O D, et al., Dement Geriatr Cogn Disord 2012, 30: 486-491; Wisniewski T, et al., Am J Pathol 1994, 145: 1030-1035) and α-1 anti-chymotrypsin (ACT) (Nilsson L N, et al. Cognitive Neurobiol Aging 2004, 25: 1153-1167)), simple elevation of APP levels is a sufficient genetic cause of DS and AD (Hooli B V, et al., Neurology 2012, 78: 1250-1257; McNaughton D, et al., Neurobiol Aging 2012, 33: 426 e413-421).

Currently, improved early diagnosis for AD has been sufficiently refined so that levels of β-amyloid protein & phosphorylated tau neurofibrillary tangle protein in the cerebrospinal fluid of MCI patients predicts the onset of AD with greater accuracy than ever before (De Meyer et al., Arch Neurol 2010, 67, 949-956). It is now critically needed to develop novel therapies for neurodegenerative disorders such as AD and DS.

SUMMARY

Provided herein are compounds or agents that can be used to inhibit or reduce the translation of amyloid precursor protein (APP). Without wishing to be bound by theory, because APP over-expression has been linked to Alzheimer's disease (AD) and Down Syndrome (DS), the compounds or agents disclosed herein can be used to treat AD and DS.

In one aspect, disclosed herein is a method of treating a neurodegenerative disorder in a subject, the method comprising administering to the subject in need thereof an effective amount of an agent that inhibits or reduces translation of amyloid precursor protein, wherein the agent is a compound of Formula A or B, or a pharmaceutically acceptable salt thereof.

In some embodiments, the agent is a compound of Formula C or D, or a pharmaceutically acceptable salt thereof.

In some embodiments, the agent is selected from a compound of Formulas I-XII, or a pharmaceutically acceptable salt thereof.

In some embodiments, the agent is a compound of Formula I or XII, or a pharmaceutically acceptable salt thereof.

In some embodiments, the neurodegenerative disorder is selected from the group consisting of Alzheimer's disease, Down syndrome, Parkinson's disease, Huntington's Disease, Amyotrophic Lateral Sclerosis (also termed Lou Gehrig's disease) and Multiple Sclerosis.

In some embodiments, the neurodegenerative disorder is Alzheimer's disease or Down syndrome.

In another aspect, disclosed herein is a method of decreasing amyloid-beta production in a subject's brain, the method comprising administering to the subject in need thereof an effective amount of an agent that inhibits or reduces translation of amyloid precursor protein, wherein the agent is a compound of Formula A or B, or a pharmaceutically acceptable salt thereof.

In some embodiments, the agent is a compound of Formula C or D, or a pharmaceutically acceptable salt thereof.

In some embodiments, the agent is selected from a compound of Formulas I-XII, or a pharmaceutically acceptable salt thereof.

In some embodiments, the agent is a compound of Formula I or XII, or a pharmaceutically acceptable salt thereof.

In some embodiments, the subject is in need for treating a neurodegenerative disorder.

In some embodiments, the neurodegenerative disorder is selected from the group consisting of Alzheimer's disease, Down syndrome, Parkinson's disease, Huntington's Disease, Amyotrophic Lateral Sclerosis (also termed Lou Gehrig's disease) and Multiple Sclerosis.

In some embodiments, the neurodegenerative disorder is Alzheimer's disease or Down syndrome.

In some embodiments, the amyloid-beta is Aβ-42.

In another aspect, disclosed herein is a method of restoring or maintaining iron homeostasis in a subject's brain, the method comprising administering to the subject in need thereof an effective amount of an agent that inhibits or reduces translation of amyloid precursor protein, wherein the agent is a compound of Formula A or B, or a pharmaceutically acceptable salt thereof.

In some embodiments, the agent is a compound of Formula C or D, or a pharmaceutically acceptable salt thereof.

In some embodiments, the agent is selected from a compound of Formulas I-XII, or a pharmaceutically acceptable salt thereof.

In some embodiments, the agent is a compound of Formula I or XII, or a pharmaceutically acceptable salt thereof.

In some embodiments, the subject has a neurodegenerative disorder.

In some aspects of all embodiments, the subject is a mammal.

In some aspects of all embodiments, the mammal is a human.

A further aspect of the invention relates to the use of an agent which inhibits or reduces translation of amyloid precursor protein for the preparation of a medicament for treatment or prevention of a neurodegenerative disorder.

BRIEF DESCRIPTION OF THE DRAWINGS

FIGS. 1A-1D show the alignment of human and mouse APP 5'UTRs with human PrP 5'UTR sequences relative to the L- and H-ferritin Iron-responsive elements (IREs). FIG. 1A: The human and mouse APP 5'UTR specific IRE-like RNA stem loops, the human PrP 5'UTR, and the human and mouse SNCA specific IRE-like stem loops each aligned adjacent to the ferritin L- and H IRE RNA stem loops. Shown, the L- and H-mRNAs encode canonical IRE RNA stem loops whereas the APP IRE in non-canonical although fully iron responsive. The α-synuclein IRE (SNCA IRE) represents a non-canonical IRE traversing the central splice junction of exon-1 and exon-2 (the CAGUGN loop/splice site sequences) of SNCA mRNA. Typical IRE stem loops fold to exhibit an apical AGU pseudotriloop which is depicted in red lettering at the apex of the 11-ferritin and SNCA IREs relative to an analogous AGA from the IRE-like stem loop encoded by APP mRNA. The sequence ID for the sequences from left to right is SEQ ID NO: 1, SEQ ID NO: 2, SEQ ID NO: 3, SEQ ID NO: 4, SEQ ID NO: 5, SEQ ID NO: 6, and SEQ ID NO: 7. FIG. 1B: Maps of the 5'UTRs encoding by the human and mouse APP mRNAs, PrP mRNA, SNCA mRNA, and the mRNAs for L- and H-ferritin (IRE stem loops are displayed as lollipops). FIG. 1C: Relative alignment of the sequences that encode the 5'UTR specific IRE-like stem loops in APP mRNA (human and mouse), human PrP mRNA, human SNCA mRNA, and the L- and H-ferritin mRNAs. The sequence ID for the sequences from top to bottom is SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, and SEQ ID NO: 17. FIG. 1D: Screen and counter-screening Constructs: The APP 5'UTR cassette was subcloned in front of the luciferase reporter gene in the dicistronic pCD(APP) reporter construct. The same-sized and related PrP 5'UTR was subcloned in an identical format into the pCD(PrP).

FIG. 3A: Chemical structure of JTR-009, 4-(5-methyl-1H-benzimidazol-2yl) aniline, compared to the anti-apoptotic stroke agent PFTa, (275 Da), a tricyclic benzothiazole. FIGS. 3B and 3C: Dose-responsive (0, 10 µM, 20 µM, 30 µM) treatment of SH-SY5Y cells for 48 hours to measure the capacity of JTR-009 and PFT-α to limit APP expression relative to β-actin and SNCA levels. The representative western blot experiment in FIG. 3B contributed to densitometry for the histogram shown in FIG. 3C (N=3). FIG. 3D: Dose-responsive measurement of total amyloid Aβ levels in response to the APP 5'UTR inhibitors JTR-005 and JTR-009, measured by benchmarked ELISA in conditioned medium of 72-hour treated SH-SY5Y cells. Shown are the mean values for the reduction of levels of Aβ±SEM (N=4) after treatment of the cells with JTR-009 and JTR-005 at 0.01 μM (*=p<0.01), 0.1 μM (=p<0.015), and 1 μM (*=p<0.01) analyzed by ANOVA (N=5). Dotted line: Representative LDH assay parallel to AP determination for SH-SY5Y cells treated for 72 hours at concentrations up to 100 μM of JTR-009 (N=4). FIG. 3E: MTS assay for cellular mitochondrial viability after treatment of SH-SY5Y cells with JTR-005 and JTR-009 at the concentrations shown. Y axis: Percent of maximal viability ±SEM after treatment of the cells with JTR-009 and HR-005 (N=3)). Shown are the relative trend-lines for the dose-responsive viability of JTR-005 and JTR-009 compared to untreated cells ('poly'=nonlinear polynomial regression of the data).

FIG. 4A: Dose responsive measurement of the capacity of JTR-009 to limit APP 5'UTR-luciferase expression relative to posiphen, a known APP translation blocker (JTR-009: $IC_{50}$=0.1 μM; posiphen: $IC_{50}$=5 μM, N=4). FIG. 4B (Top Panel): Dose-responsive reduction APP levels in SH-SY5Y cells treated 48 hours at 0.1 μM, 0.5 μM and 1 μM JTR-009. Western blot for APP levels using N-terminal 22C11 antibody (standardization with Il-actin as loading control). Bottom Panel: Histogram quantitation of the relative expression of APP/I3-actin in SH-SY5Y cells. FIG. 4C (Top Panel): Lysates from the experiment in FIG. 4B was analyzed by Western blotting using APP the C-terminal specific (A8717) antibody and β-actin antibody. Bottom Panel: histogram quantitation of the relative expression of APP/(β-actin in SH-SY5Y cells from autoradiographic film subjected to densitometry (N=3). FIG. 4D: Dose-responsive capacity of JTR-009 to limit APP expression in primary E-18 mouse neurons (1 nM). The relative α-synuclein (SATCA) expression was calculated. Shown, the combined data was graphed into a histogram where mean values from separate assays were calculated from densitometry of Western blots (N=5). FIG. 4E: Real-time qPCR measurement of the dose-responsive measurement of the levels of APP mRNA and TfR mRNAs in SH-SY5Y cells treated with escalating concentrations of JTR-009. FIG. 4F: Equivalent real-time qRT-PCR analysis to measure TfR inRNA levels in SH-SY5Y cells treated with 25 μM desferrioxamine (DFO) (Positive control mRNA).

FIGS. 5A-5E show RNA pulldown assay to measure the dose-dependent capacity of the cyclic benzimidazole JTR-009 to substitute for IRP1 binding to APP 5'UTR sequences in SH-SY5Y cells: correlated repression of APP translation. RNA pulldown assays were conducted as illustrated in FIG. 6 and as described by Cho et al., 2010. FIGS. 5A and 5B: Representative RNA binding assays in which recovered beads measured the dose-responsive capacity of JTR-009 (0 μM, 0.3 μM, 3 μM and 30 μM) to inhibit IRP1 binding to 30 base biotinylated probes encoding the APP 5'UTR. In FIG. 5B, Western blots measured relative levels of IRP1 and IRP2 bound to biotinylated RNA probes for APP IRE sequences after recovery in steptavidin bead fractions. Densitomteric quantitation of bead-specific IRP1 is shown in FIG. 5A. FIG. 5C: Measurement of the dose-dependent off-target action of JTR-009 to suppress H-ferritin IRE binding to SH-SY5Y specific IRP1 and IRP2 (bead fraction). FIGS. 5D and 5E: Dose-dependent decrease of APP levels in response to JTR-009 measured in the supernatants of bead fractions (experimental<control set (p<0.001). FIG. 5E: Western blots of lysate supernatants showing APP as measured using the N terminal specific 22C11 and C-terminal specific A8717 antibodies. FIG. 5D: Densitometric quantitation of the data in FIG. 5E to measure the extent to which JTR-009 dose dependently repressed APP expression in SH-SY5Y cells (Dunnetts test, p=0.03). Data from 5 separate trials, each in triplicate.

FIG. 6A: Top Panel: Cartoon representation of the protocol employed to detect RNA binding between IRE probes and IRP1 in SH-SY5Y cell lysates. Bottom Panel: Effect of JTR-009 treatment of SH-SY5Y cells (24 hours, 10 μM) to alter ferritin-H IRE binding to IRP1 compared to that of the APP IRE. FIG. 6B: The calcein assay for iron levels in SH-SY5Y cells in response to treatment with JTR-009. Cells were treated with either DMSO (negative control), extracellular iron chelator (DPTA), or JTR-009 at 10 μM for 48 hours. FIG. 6C: The anti-amyloid-Aβ-42 efficacy of the APP 5'UTR inhibitors JTR-005 and JTR-009, as measured in conditioned medium from SH-SY5Y neuronal cells (Chemiluminescent BetaMark x-42 ELISA assay from Covance, Inc). Data shows the mean values for the reduction of levels of Aβ-42±SEM (N=3) after 72-hour treatment of the cells with JTR-009 compared to JTR-005 at 10 μM (p<0.01), analyzed by ANOVA.

FIGS. 8A-8D compare the compound BL-1 (K24025829 from the Broad Institute library) with strophanthidin. BL-1 (FIG. 8C) inhibited APP 5'UTR conferred translation at concentrations 500 times less than strophanthidin (FIG. 8A), the cardiac glycoside which is an FDA drug that blocked APP expression translation. FIG. 8B is the chemical structure for strophanthidin. FIG. 8D is the chemical structure for BL-1.

DETAILED DESCRIPTION

Figure 1A:
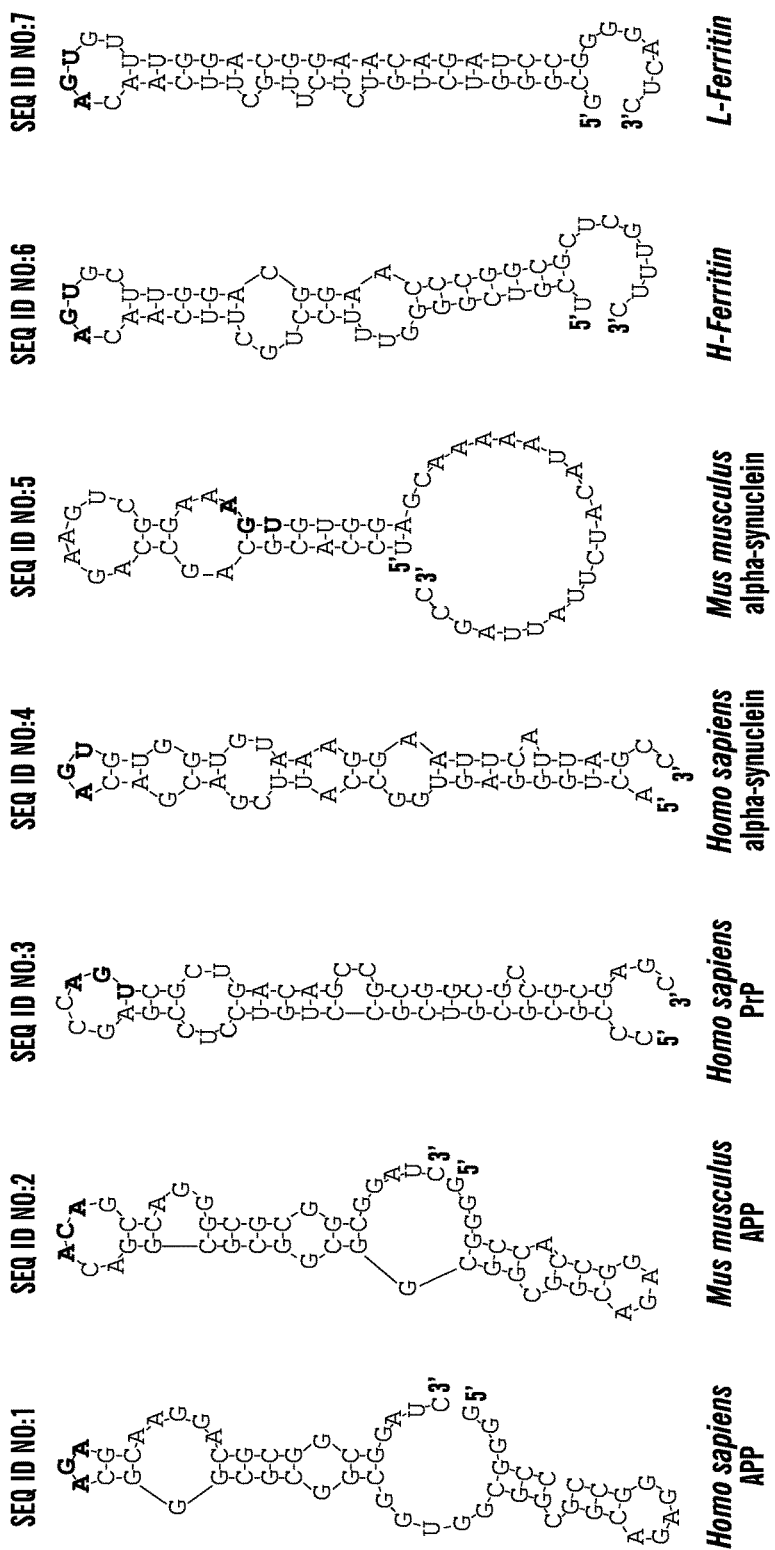

The invention discloses certain compounds or agents that can be used to inhibit or reduce the translation of amyloid precursor protein (APP). Without wishing to be bound by theory, iron influx drives the translational expression of the neuronal amyloid precursor protein (APP), which has a role in iron efflux, via a classic release of repressor interaction of its mRNA with iron-regulatory protein-1 (IRP1). The compounds or agents described herein inhibit or reduce APP translation by intercalating into RNA sequences folded from the APP 5'UTR and irreversibly replacing IRP1 (FIG. 7), while maintaining β-actin expression and cell viability.

Without wishing to be bound by theory, because APP over-expression has been linked to Alzheimer's disease (AD) and Down Syndrome (DS), the compounds or agents disclosed herein can be used to treat AD and DS. Accordingly, in one aspect, provided herein is a method of treating a neurodegenerative disorder in a subject, the method comprising administering to the subject in need thereof an effective amount of an agent that inhibits or reduces translation of amyloid precursor protein.

In some embodiments, the agent is a compound of Formula A or B, or a pharmaceutically acceptable salt thereof:

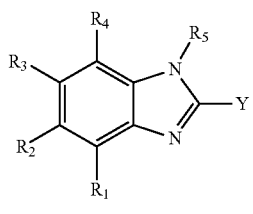

Formula A

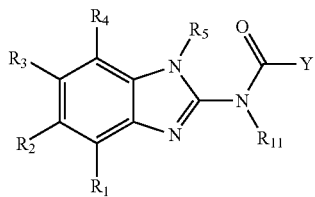

Formula B

In compounds of Formula A or B, Y can be an optionally substituted aryl or heteroaryl. In some embodiments, Y is an optionally substituted phenyl. When the phenyl group is substituted, the substituent can be present at the ortho, meta, or para position on the phenyl relative to the rest of the compound. In some embodiments, the optionally substituted phenyl is substituted with one or more substituents selected from amino, halogen, hydroxyl, thiol, methoxy, methylthioxy, carboxyl, nitro, triflouomethyl, cyano, and any combinations thereof.

In some embodiments, Y is 4-aminophenyl, 4-fluorophenyl, 4-methoxyphenyl, 4-N,N-dimethylaminophneyl, 2-aminophenyl, 2-fluorophenyl, 2-methoxy-4-(methylthio)phenyl, or 4-pyridyl.

In compounds of Formula A or B, $R_1$, $R_2$, $R_3$, $R_4$, $R_5$, and $R_{11}$ are each independently hydrogen, halogen, hydroxyl, nitro, cyano, isocyano, thiocyano, isothiocyano, alkyl, alkoxy, alkylthio, amino, monoalkylamino, dialkylamino, acyl, carbonyl, carboxyl, azide, sulfinyl, sulfonyl, sulfino, sulfo, or thiol.

In some embodiments, a compound of Formula A or B is a compound of Formula C or Formula D or a pharmaceutically acceptable salt thereof:

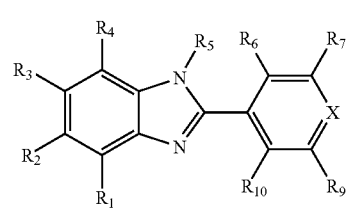

Formula C

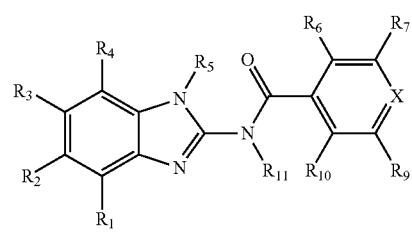

Formula D

In compounds of Formula C or D, X can be $CR_8$ or N and $R_1$, $R_2$, $R_3$, $R_4$, $R_5$, $R_6$, $R_7$, $R_8$, $R_9$, $R_{10}$, and $R_{11}$ are each independently hydrogen, halogen, hydroxyl, nitro, cyano, isocyano, thiocyano, isothiocyano, alkyl, alkoxy, alkylthio, amino, monoalkylamino, dialkylamino, acyl, carbonyl, carboxyl, azide, sulfinyl, sulfonyl, sulfino, sulfo, or thiol.

When X is $CR_8$, $R_8$ can be selected independently for each occurrence from the group consisting of hydrogen, halogen, hydroxyl, nitro, cyano, isocyano, thiocyano, isothiocyano, alkyl, alkoxy, alkylthio, amino, monoalkylamino, dialkylamino, acyl, carbonyl, carboxyl, azide, sulfinyl, sulfonyl, sulfino, sulfo, or thiol. In some embodiments, $R_8$ can be a hydrogen, amino, dialkylamino, halogen, hydroxyl, thiol, methoxy, methylthioxy, carboxyl, nitro, triflouomethyl, or cyano. In some embodiments, $R_8$ is hydrogen, amino, fluoro, methoxy dimethylamino, or methylthioxy.

In compounds of Formula A, B, C or D, at least one (e.g., one, two, three, four, five, or six) of $R_1$, $R_2$, $R_3$, $R_4$, $R_5$, and $R_{11}$ can be hydrogen. In some embodiments, $R_1$ is hydrogen. In some embodiments, $R_2$ is hydrogen. In some embodiments, $R_3$ is hydrogen. In some embodiments, $R_4$ is hydrogen. In some embodiments, $R_5$ is hydrogen. In some embodiments, $R_{11}$ is hydrogen.

In compounds of Formula A, B, C or D, at least one (e.g., one, two, three, four, five, or six) of $R_1$, $R_2$, $R_3$, $R_4$, $R_5$, and $R_{11}$ can be optionally substituted $C_1$-$C_6$ alkyl. In some embodiments, $R_1$ is optionally substituted $C_1$-$C_6$ alkyl. In some embodiments, $R_2$ is optionally substituted $C_1$-$C_6$ alkyl. In some embodiments, $R_3$ is optionally substituted $C_1$-$C_6$ alkyl. In some embodiments, $R_4$ is optionally substituted $C_1$-$C_6$ alkyl. In some embodiments, $R_5$ is optionally substituted $C_1$-$C_6$ alkyl. In some embodiments, $R_{11}$ is optionally substituted $C_1$-$C_6$ alkyl. Exemplary $C_1$-$C_6$ alkyl include, but are not limited to, methyl, ethyl, propyl, allyl, propargyl, butyl, but-2-yl, 2-methylpropyl, and pentyl. In some embodiments, at least one (e.g., one, two, three, four, five, or six) of $R_1$, $R_2$, $R_3$, $R_4$, $R_5$, and $R_{11}$ is a methyl.

In compounds of Formula A, B, C or D, at least one (e.g., one, two, three, four, five, or six) of $R_1$, $R_2$, $R_3$, $R_4$, $R_5$, and $R_{11}$ can be trifluoromethyl. In some embodiments, $R_1$ is trifluoromethyl. In some embodiments, $R_2$ is trifluoromethyl. In some embodiments, $R_3$ is trifluoromethyl. In some embodiments, $R_4$ is trifluoromethyl. In some embodiments, $R_5$ is trifluoromethyl. In some embodiments, $R_{11}$ is trifluoromethyl.

In compounds of Formula A, B, C or D, at least one (e.g., one, two, three, four, or five) of $R_1$, $R_2$, $R_3$, $R_4$, and $R_5$ can be amino, alkylamino or dialkyamino, which can be optionally substituted. In some embodiments, $R_1$ is amino, alkylamino or dialkyamino, which can be optionally substituted. In some embodiments, $R_2$ is amino, alkylamino or dialkyamino, which can be optionally substituted. In some embodiments, $R_3$ is amino, alkylamino or dialkyamino, which can be optionally substituted. In some embodiments, $R_4$ is amino, alkylamino or dialkyamino, which can be optionally substituted. In some embodiments, $R_5$ is amino, alkylamino or dialkyamino, which can be optionally substituted. In some embodiments, at least one (e.g., one, two, three, four, or five) of $R_1$, $R_2$, $R_3$, $R_4$, and $R_5$ is an amino.

In compounds of Formula A, B, C or D, at least one (e.g., one, two, three, four, five, or six) of $R_1$, $R_2$, $R_3$, $R_4$, $R_5$, and $R_{11}$ can be halogen. In some embodiments, $R_1$ is halogen. In some embodiments, $R_2$ is halogen. In some embodiments, $R_3$ is halogen. In some embodiments, $R_4$ is halogen. In some embodiments, $R_5$ is halogen. In some embodiments, $R_{11}$ is halogen. In some embodiments, at least one (e.g., one, two, three, four, five, or six) of $R_1$, $R_2$, $R_3$, $R_4$, $R_5$, and $R_{11}$ is fluoro.

In compounds of Formula A, B, C or D, at least one (e.g., one, two, three, four, or five) of $R_1$, $R_2$, $R_3$, $R_4$, and $R_5$ can be hydroxyl. In some embodiments, $R_1$ is hydroxyl. In some embodiments, $R_2$ is hydroxyl. In some embodiments, $R_3$ is hydroxyl. In some embodiments, $R_4$ is hydroxyl. In some embodiments, $R_5$ is hydroxyl.

In compounds of Formula A, B, C or D, at least one (e.g., one, two, three, four, or five) of $R_1$, $R_2$, $R_3$, $R_4$, and $R_5$ can be optionally substituted alkoxy. In some embodiments, $R_1$ is optionally substituted alkoxy. In some embodiments, $R_2$ is optionally substituted alkoxy. In some embodiments, $R_3$ is optionally substituted alkoxy. In some embodiments, $R_4$ is optionally substituted alkoxy. In some embodiments, $R_5$ is optionally substituted alkoxy. In some embodiments, alkoxy is methoxy.

In compounds of Formula A, B, C or D, at least one (e.g., one, two, three, four, or five) of $R_1$, $R_2$, $R_3$, $R_4$, and $R_5$ can be thiol. In some embodiments, $R_1$ is thiol. In some embodiments, $R_2$ is thiol. In some embodiments, $R_3$ is thiol. In some embodiments, $R_4$ is thiol. In some embodiments, $R_5$ is thiol.

In compounds of Formula A, B, C or D, at least one (e.g., one, two, three, four, or five) of $R_1$, $R_2$, $R_3$, $R_4$, and $R_5$ can be alkylthio, which can be optionally substituted. In some embodiments, $R_1$ is alkylthio, which can be optionally substituted. In some embodiments, $R_2$ is alkylthio, which can be optionally substituted. In some embodiments, $R_3$ is alkylthio, which can be optionally substituted. In some embodiments, $R_4$ is alkylthio, which can be optionally substituted. In some embodiments, $R_5$ is alkylthio, which can be optionally substituted.

In compounds of Formula A, B, C or D, at least one (e.g., one, two, three, four, or five) of $R_1$, $R_2$, $R_3$, $R_4$, and $R_5$ can be carboxyl. In some embodiments, $R_1$ is carboxyl. In some embodiments, $R_2$ is carboxyl. In some embodiments, $R_3$ is carboxyl. In some embodiments, $R_4$ is carboxyl. In some embodiments, $R_5$ is carboxyl.

In compounds of Formula A, B, C or D, at least one (e.g., one, two, three, four, or five) of $R_1$, $R_2$, $R_3$, $R_4$, and $R_5$ can be nitro. In some embodiments, $R_1$ is nitro. In some embodiments, $R_2$ is nitro. In some embodiments, $R_3$ is nitro. In some embodiments, $R_4$ is nitro. In some embodiments, $R_5$ is nitro.

In compounds of Formula A, B, C or D, at least one (e.g., one, two, three, four, or five) of $R_1$, $R_2$, $R_3$, $R_4$, and $R_5$ can be cyano. In some embodiments, $R_1$ is cyano. In some embodiments, $R_2$ is cyano. In some embodiments, $R_3$ is cyano. In some embodiments, $R_4$ is cyano. In some embodiments, $R_5$ is cyano.

In compounds of Formula C or D, at least one (e.g., one, two, three or four) of $R_6$, $R_7$, $R_9$ and $R_{10}$ can be hydrogen. In some embodiments, $R_6$ is hydrogen. In some embodiments, $R_7$ is hydrogen. In some embodiments, $R_8$ is hydrogen. In some embodiments, $R_8$ is hydrogen.

In compounds of Formula C or D, at least one (e.g., one, two, three or four) of $R_6$, $R_7$, $R_9$ and $R_{10}$ can be optionally substituted $C_1$-$C_6$alkyl. In some embodiments, $R_6$ is optionally substituted $C_1$-$C_6$alkyl. In some embodiments, $R_7$ is optionally substituted $C_1$-$C_6$alkyl. In some embodiments, $R_9$ is optionally substituted $C_1$-$C_6$alkyl. In some embodiments, $R_{10}$ is optionally substituted $C_1$-$C_6$alkyl. Exemplary $C_1$-$C_6$alkyl include, but are not limited to, methyl, ethyl, propyl, allyl, propargyl, butyl, but-2-yl, 2-methylpropyl, and pentyl. In some embodiments, at least one (e.g., one, two, three, four, five, or six) of $R_6$, $R_7$, $R_9$ and $R_{10}$ is a methyl.

In compounds of Formula C or D, at least one (e.g., one, two, three or four) of $R_6$, $R_7$, $R_9$ and $R_{10}$ can be trifluoromethyl. In some embodiments, $R_6$ is trifluoromethyl. In some embodiments, $R_7$ is trifluoromethyl. In some embodiments, $R_9$ is trifluoromethyl. In some embodiments, $R_{10}$ is trifluoromethyl.

In compounds of Formula C or D, at least one (e.g., one, two, three or four) of $R_6$, $R_7$, $R_9$ and $R_{10}$ can be amino, alkylamino or dialkyamino, which can be optionally substituted. In some embodiments, $R_6$ is amino, alkylamino or dialkyamino, which can be optionally substituted. In some embodiments, $R_7$ is amino, alkylamino or dialkyamino, which can be optionally substituted. In some embodiments, $R_9$ is amino, alkylamino or dialkyamino, which can be optionally substituted. In some embodiments, $R_{10}$ is amino, alkylamino or dialkyamino, which can be optionally substituted. In some embodiments, at least one (e.g., one, two, three, or four) of $R_6$, $R_7$, $R_9$ and $R_{10}$ is an amino. In some embodiments, at least one (e.g., one, two, three, or four) of $R_6$, $R_7$, $R_9$ and $R_{10}$ is a dimethylamino.

In compounds of Formula C or D, at least one (e.g., one, two, three or four) of $R_6$, $R_7$, $R_9$ and $R_{10}$ can be halogen. In some embodiments, $R_6$ is halogen. In some embodiments, $R_7$ is halogen. In some embodiments, $R_9$ is halogen. In some embodiments, $R_{10}$ is halogen. In some embodiments, at least one (e.g., one, two, three or four) of $R_6$, $R_7$, $R_9$, and $R_{10}$ is fluoro.

In compounds of Formula C or D, at least one (e.g., one, two, three or four) of $R_6$, $R_7$, $R_9$ and $R_{10}$ can be hydroxyl. In some embodiments, $R_6$ is hydroxyl. In some embodiments, $R_7$ is hydroxyl. In some embodiments, $R_9$ is hydroxyl. In some embodiments, $R_{10}$ is hydroxyl.

In compounds of Formula C or D, at least one (e.g., one, two, three or four) of $R_6$, $R_7$, $R_9$ and $R_{10}$ can be optionally substituted alkoxy. In some embodiments, $R_6$ is optionally substituted alkoxy. In some embodiments, $R_7$ is optionally substituted alkoxy. In some embodiments, $R_9$ is optionally substituted alkoxy. In some embodiments, $R_{10}$ is optionally substituted alkoxy. In some embodiments, alkoxy is methoxy.

In compounds of Formula C or D, at least one (e.g., one, two, three or four) of $R_6$, $R_7$, $R_9$ and $R_{10}$ can be thiol. In some embodiments, $R_6$ is thiol. In some embodiments, $R_7$ is thiol. In some embodiments, $R_9$ is thiol. In some embodiments, $R_{10}$ is thiol.

In compounds of Formula C or D, at least one (e.g., one, two, three or four) of $R_6$, $R_7$, $R_9$ and $R_{10}$ can be alkylthio, which can be optionally substituted. In some embodiments, $R_6$ is alkylthio, which can be optionally substituted. In some embodiments, $R_7$ is alkylthio, which can be optionally substituted. In some embodiments, $R_9$ is alkylthio, which can be optionally substituted. In some embodiments, $R_{10}$ is alkylthio, which can be optionally substituted. In some embodiments, alkylthio is methylthioxy.

In compounds of Formula C or D, at least one (e.g., one, two, three or four) of $R_6$, $R_7$, $R_9$ and $R_{10}$ can be carboxyl. In some embodiments, $R_6$ is carboxyl. In some embodiments, $R_7$ is carboxyl. In some embodiments, $R_9$ is carboxyl. In some embodiments, $R_{10}$ is carboxyl.

In compounds of Formula C or D, at least one (e.g., one, two, three or four) of $R_6$, $R_7$, $R_9$ and $R_{10}$ can be nitro. In some embodiments, $R_6$ is nitro. In some embodiments, $R_7$ is nitro. In some embodiments, $R_9$ is nitro. In some embodiments, $R_{10}$ is nitro.

In compounds of Formula C or D, at least one (e.g., one, two, three or four) of $R_6$, $R_7$, $R_9$ and $R_{10}$ can be cyano. In some embodiments, $R_6$ is cyano. In some embodiments, $R_7$ is cyano. In some embodiments, $R_9$ is cyano. In some embodiments, $R_{10}$ is cyano.

Compounds of formula A, B, C, or D are either commercially available or can be synthesized by methods well known to one of skill in the chemical arts.

In some embodiments, a compound of Formula C or D is a compound of Formulas I-XII, or a pharmaceutically acceptable salt thereof:

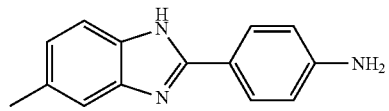

Formula I

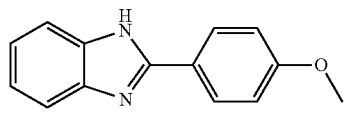

Formula II

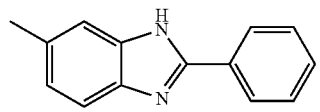

Formula III

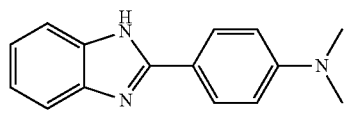

Formula IV

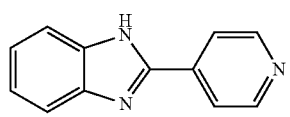

Formula V

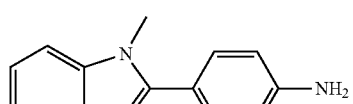

Formula VI

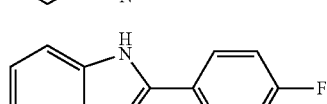

Formula VII

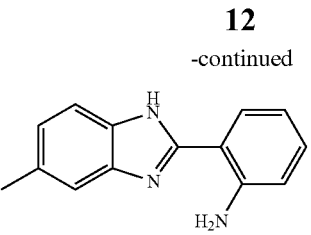

Formula VIII

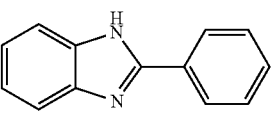

Formula VIIII

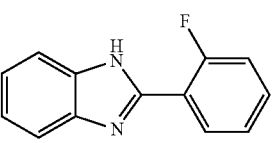

Formula X

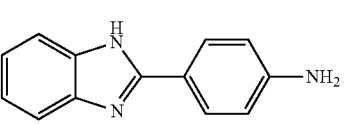

Formula XI

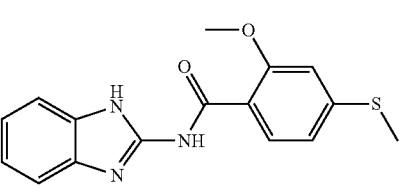

Formula XII

In some embodiments, the agent is a compound of Formula I (also referred to as JTR-009 herein) or XII (also referred to as BL-1 herein), or a pharmaceutically acceptable salt thereof. For example, the inventors have shown that the compound of Formula I was about 10-fold more effective to limit APP translation than posiphen, a well-tolerated APP translation blocker that is being developed for AD treatment.

APP level or concentration can be measured by methods including, but not limited to, immunoblotting and western blotting.

The agents disclosed herein can be used to treat, in a subject, any neurodegenerative disorder that results from overproduction of APP or amyloid-beta (Aβ). In some embodiments, the neurodegenerative disorder is Alzheimer's disease, Down syndrome, Parkinson's disease, Huntington's Disease, Amyotrophic Lateral Sclerosis (also termed Lou Gehrig's disease), or Multiple Sclerosis. In one embodiment, the neurodegenerative disorder is Alzheimer's disease or Down syndrome. It should be noted that the agents or methods disclosed herein are not limited to treat a particular stage (e.g., early or late stage) of a neurodegenerative disorder.

In some embodiments, the subject has amyloidosis. Amyloidosis is a disease that occurs when substances called amyloid proteins become insoluble and deposit in the subject's organs. And generally for a neurodegenerative disorder, the amyloid proteins deposit in the subject's brain, affecting the normal functions of the brain.

In some embodiments, the subject having amyloidosis has Alzheimer's disease. It is known in the art that Alzheimer's disease is a frequent type of amyloidosis in humans.

In some embodiments, the subject having amyloidosis has Down syndrome. It has been discovered that amyloid-beta deposition can occur in a subject having Down syndrome (for example, see Head & Lott, Curr Opin Neurol. 2004, 17, 95-100).

A related aspect of the invention relates to a method of decreasing amyloid-beta production in a subject's brain, the method comprising administering to the subject in need thereof an effective amount of the compound or agent disclosed herein. Amyloid-beta is produced in the brain by cutting APP, and is the main component of the amyloid plaques found in the brains of patients having e.g., Alzheimer's disease. Amyloid-beta has multiple isoforms, the most common of which are Aβ40 and Aβ42. By inhibiting or decreasing APP translation, the production of amyloid-beta can be inhibited or decreased. In some embodiments, the subject is in need for treating a neurodegenerative disorder.

Amyloid-beta can be measured by methods including, but not limited to, immunostaining, enzyme-linked immunosorbent assay (ELISA), imaging compounds (e.g., 6-OH-BTA-1) combined with positron emission tomography (PET) imaging, atomic force microscopy, and dual polarization interferometry.

Yet another aspect of the invention relates to a method of restoring or maintaining iron homeostasis in a subject's brain, the method comprising administering to the subject in need thereof an effective amount of the compound or agent disclosed herein. Without wishing to be bound by theory, increased APP can alter or perturb brain iron homeostasis based on its capacity to bind ferroportin and export iron (Duce et al., Cell 2010, 142, 857-867).

The methods described herein can be used in combination with other therapies for treating a neurodegenerative disease, decreasing amyloid-beta production, or restoring or maintaining iron homeostasis. For example, promising therapies for Alzheimer's disease include, but are not limited to, amyloid-chaperones, tau, and modulators of cholesterol metabolism. Methods of treating Alzheimer's disease are also disclosed in, for example, U.S. Pat. No. 5,292,730, U.S. Pat. No. 6,323,218, U.S. Pat. No. 7,119,085, U.S. Pat. No. 7,432,389, U.S. Pat. No. 8,377,947, WO2012034019, WO2013181618, US20020164668, and WO2014037532, the contents of each of which are incorporated by references in its entirety. Methods of treating Down syndrome are disclosed in, for example, U.S. Pat. No. 8,143,311, U.S. Pat. No. 8,680,105, US20120277218, US20120283248, US20040072744, and US20070054940, the contents of each of which are incorporated by references in its entirety.

Administration of Pharmaceutical Compositions

The agents disclosed herein or pharmaceutical compositions comprising the agents thereof may be administered in any dose or dosing regimen. With respect to the therapeutic methods of the invention, it is not intended that the administration be limited to a particular mode of administration, dosage, or frequency of dosing. An effective amount, e.g., a therapeutically effective dose of the agent disclosed herein may be administered to the patient in a single dose or in multiple doses. When multiple doses are administered, the doses may be separated from one another by, for example, one hour, three hours, six hours, eight hours, one day, two days, one week, two weeks, or one month. For example, a composition comprising the agent disclosed herein can be administered for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compositions. For example, the dosage of the therapeutic can be increased if the lower dose does not provide sufficient therapeutic activity.

While the attending physician ultimately will decide the appropriate amount and dosage regimen, an effective amount of a composition comprising the agent disclosed herein can be provided at a dose of 0.0001, 0.01, 0.01 0.1, 1, 5, 10, 25, 50, 100, 500, or 1,000 mg/kg. Effective doses may be extrapolated from dose-response curves derived from in vitro or animal model test bioassays or systems. In some embodiments, doses of a composition comprising the agent disclosed herein are about 1 pg/kg to 100 mg/kg (body weight of patient), although lower and higher doses can also be administered.

Dosages for a particular patient or subject can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose is determined by the efficacy of the particular formulation, and the activity, stability or serum half-life of a composition comprising the agent disclosed herein, and the condition of the patient, the particular neurodegenerative disorder to be treated, as well as the body weight or surface area of the patient to be treated. The size of the dose is also determined by the existence, nature, and extent of any adverse side-effects that accompany the administration of a particular formulation, or the like in a particular subject. Therapeutic compositions are optionally tested in one or more appropriate in vitro and/or in vivo animal models of disease, and known to persons of ordinary skill in the art, to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of the pharmaceutical composition at various concentrations, e.g., as applied to the mass and overall health of the patient. Administration can be accomplished via single or divided doses.

For example, a therapeutically effective amount can be estimated initially either in cell culture assays or in animal models, usually mice, rabbits, dogs, or pigs. The animal model is also used to achieve a desirable concentration range and route of administration. Such information can then be used to determine useful doses and routes for administration in other subjects. Generally, the therapeutically effective amount is dependent of the desired therapeutic effect.

In determining the effective amount of a composition comprising the agent disclosed herein to be administered in the treatment or prophylaxis of a disease, the physician can evaluate circulating plasma levels, formulation toxicities, and progression of the disease. The selected dosage level will also depend upon a variety of factors including the activity of the particular compound of the present invention employed, or the salt thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

In some embodiments, a composition comprising the agent disclosed herein can be administered at a dose in accordance with good medical practice, taking into account the clinical condition of the individual patient, the site and method of administration, scheduling of administration, patient age, sex, body weight and other factors known to medical practitioners.

Dosage regimens of a composition comprising the agent disclosed herein can be adjusted to provide the optimum desired response (e.g. a therapeutic or prophylactic response). For example, a single bolus can be administered, several divided doses may be administered over time or the dose may be proportionally reduced or increased as indicated by the exigencies of the therapeutic situation. It can be advantageous to formulate parenteral compositions in dosage unit form for ease of administration and uniformity of dosage.

Furthermore, actual dosage levels of the agent disclosed herein in a pharmaceutical composition can be varied so as to obtain an amount of the active ingredient which is effective to achieve the desired therapeutic response for a particular subject, composition, and mode of administration, without being toxic to the subject. A pharmaceutical composition comprising the agent disclosed herein can be a "therapeutically effective amount" and/or a "prophylactically effective amount". In general, a suitable daily dose of a composition comprising the agent disclosed herein will be that amount of the agent disclosed herein which is the lowest dose effective to produce a therapeutic effect, such as a reduction of a symptom of AD or DS. Such an effective dose will generally depend upon the factors described above.

The dosage level administered to a subject can be constant over a desired period of time, for example, at least 1 week, at least 2 weeks, at least 3 weeks, at least 1 month, at least 2 months, at least 3 months, at least 6 months, at least 1 year, or at least 5 years. Alternatively, the dosage level administered to a subject can vary depending on the progression of the neurodegenerative disorder being treated.

It is to be noted that dosage values may vary with the type and severity of the neurodegenerative disorder to be treated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The efficacy and toxicity of the compound can be determined by standard pharmaceutical procedures in cell cultures or experimental animals, e.g., ED50 (the dose is effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions which exhibit large therapeutic indices are preferred.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. It is also noted that humans are treated generally longer than the mice or other experimental animals, which treatment has a length proportional to the length of the disease process and drug effectiveness.

In one embodiment, it may be desirable to administer the pharmaceutical composition comprising the agent disclosed herein locally to the area in need of treatment; this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes.

In some embodiments, the pharmaceutical composition can be administered to a subject orally (e.g., in capsules, suspensions or tablets) or by parenteral administration. Conventional methods for oral administration include any one of the following; tablets, suspensions, solutions, emulsions, capsules, powders, syrups and the like are usable. Parenteral administration can include, for example, intramuscular, intravenous, intraarticular, intraarterial, intrathecal, subcutaneous, or intraperitoneal administration. The pharmaceutical composition can also be administered orally, transdermally, topically, by inhalation (e.g., intrabronchial, intranasal, oral inhalation or intranasal drops) or rectally. Administration can be local or systemic as indicated.

When administering a composition comprising the agent disclosed herein parenterally, it will generally be formulated in a unit dosage injectable form (e.g., solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (e.g., glycerol, propylene glycol, liquid polyethylene glycol), suitable mixtures thereof, and vegetable oils.

The term "Dosage unit" form as used herein refers to physically discrete units suited as unitary dosages for the subjects to be treated; each unit containing a predetermined quantity of active compound calculated to produce the desired therapeutic effect in association with the required pharmaceutical carrier.

The agent disclosed herein can also be administered in a slow-release formulation. Slow-release formulations are well known in the art and are not discussed in detail here.

Methods to Identify Subjects for Risk of or Having Alzheimer's Disease

Subjects amenable to treatment using the methods as disclosed herein include subjects at risk of a neurodegenerative disease, for example Alzheimer's Disease but not showing symptoms, as well as subjects showing symptoms of the neurodegenerative disease, for example subjects with symptoms of Alzheimer's Disease. Subjects can be screened for their likelihood of having or developing Alzheimer's Disease based on a number of biochemical and genetic markers.

One can also diagnose a subject with increased risk of developing Alzheimer's Disease using genetic markers for Alzheimer's Disease. Genetic abnormality in a few families has been traced to chromosome 21 (St. George-Hyslop et al., Science 235:885-890, 1987). One genetic marker is, for example mutations in the APP gene, particularly mutations at position 717 and positions 670 and 671 referred to as the Hardy and Swedish mutations respectively (see Hardy, TINS, supra). Other markers of risk are mutations in the presenilin genes, PS1 and PS2, and ApoE4, family history of Alzheimer's Disease, hypercholesterolemia or atherosclerosis. Subjects with APP, PS1 or PS2 mutations are highly likely to develop Alzheimer's disease. ApoE is a susceptibility gene, and subjects with the e4 isoform of ApoE (ApoE4 isoform) have an increased risk of developing Alzheimer's disease. Test for subjects with ApoE4 isoform are disclosed in U.S. Pat. No. 6,027,896, which is incorporated in its entirety herein by reference. Other genetic links have been associated with increased risk of Alzheimer's disease, for example variances in the neuronal sortilin-related receptor SORL1 may have increased likelihood of developing late-onset Alzheimer's disease (Rogaeva at al., Nat Genet. 2007 February; 39(2):168-77). Other potential Alzheimer disease susceptibility genes, include, for example ACE, CHRNB2, CST3, ESR1, GAPDHS, IDE, MTHFR, NCSTN, PRNP, PSEN1, TF, TFAM and TNF and be used to identify subjects with increased risk of developing Alzheimer's disease (Bertram et al, Nat Genet. 2007 January; 39(1): 17-23), as well as variances in the alpha-T catenin (VR22) gene (Bertram et al, J Med Genet. 2007 January; 44(1):e63) and Insulin-degrading enzyme (IDE) and Kim et al, J Biol Chem. 2007; 282:7825-32).

One can also diagnose a subject with increased risk of developing Alzheimer's disease on the basis of a simple eye test, where the presence of cataracts and/or Abeta in the lens identifies a subject with increased risk of developing Alzheimer's Disease. Methods to detect Alzheimer's disease include using a quasi-elastic light scattering device (Goldstein et al., Lancet. 2003; 12; 361:1258-65) from Neuroptix, using Quasi-Elastic Light Scattering (QLS) and Fluorescent Ligand Scanning (FLS) and a Neuroptix™ QEL scanning device, to enable non-invasive quantitative measurements of amyloid aggregates in the eye, to examine and measure deposits in specific areas of the lens as an early diagnostic for Alzheimer's disease. Method to diagnose a subject at risk of developing Alzheimer's disease using such a method of non-invasive eye test are disclosed in U.S. Pat. No. 7,107,092, which is incorporated in its entirety herein by reference.

Individuals presently suffering from Alzheimer's disease can be recognized from characteristic dementia, as well as the presence of risk factors described above. In addition, a number of diagnostic tests are available for identifying individuals who have AD. These include measurement of CSF tau and Ax3b242 levels. Elevated tau and decreased Ax3b242 levels signify the presence of Alzheimer's Disease.

There are two alternative "criteria" which are utilized to clinically diagnose Alzheimer's Disease: the DSM-IIIR criteria and the NINCDS-ADRDA criteria (which is an acronym for National Institute of Neurological and Communicative Disorders and Stroke (NINCDS) and the Alzheimer's Disease and Related Disorders Association (ADRDA); see McKhann et al., Neurology 34:939-944, 1984). Briefly, the criteria for diagnosis of Alzheimer's Disease under DSM-IIIR include (1) dementia, (2) insidious onset with a generally progressive deteriorating course, and (3) exclusion of all other specific causes of dementia by history, physical examination, and laboratory tests. Within the context of the DSM-IIIR criteria, dementia is understood to involve "a multifaceted loss of intellectual abilities, such as memory, judgment, abstract thought, and other higher cortical functions, and changes in personality and behaviour." (DSM-IIR, 1987).

In contrast, the NINCDS-ADRDA criteria set forth three categories of Alzheimer's Disease, including "probable," "possible," and "definite" Alzheimer's Disease. Clinical diagnosis of "possible" Alzheimer's Disease may be made on the basis of a dementia syndrome, in the absence of other neurologic, psychiatric or systemic disorders sufficient to cause dementia. Criteria for the clinical diagnosis of "probable" Alzheimer's Disease include (a) dementia established by clinical examination and documented by a test such as the Mini-Mental test (Foldstein et al., J. Psych. Res. 12:189-198, 1975); (b) deficits in two or more areas of cognition; (c) progressive worsening of memory and other cognitive functions; (d) no disturbance of consciousness; (e) onset between ages 40 and 90, most often after age 65; and (f) absence of systemic orders or other brain diseases that could account for the dementia. The criteria for definite diagnosis of Alzheimer's Disease include histopathologic evidence obtained from a biopsy, or after autopsy. Since confirmation of definite Alzheimer's Disease requires histological examination from a brain biopsy specimen (which is often difficult to obtain), it is rarely used for early diagnosis of Alzheimer's Disease.

One can also use neuropathologic diagnosis of Alzheimer's Disease, where the numbers of plaques and tangles in the neurocortex (frontal, temporal, and parietal lobes), hippocampus and amygdala are analyzed (Khachaturian, Arch. Neurol. 42:1097-1105; Esiri, "Anatomical Criteria for the Biopsy diagnosis of Alzheimer's Disease," Alzheimer's Disease, Current Research in Early Diagnosis, Becker and Giacobini (eds.), pp. 239-252, 1990).

One can also use quantitative electroencephalographic analysis (EEG) to diagnose Alzheimer's Disease. This method employs Fourier analysis of the beta, alpha, theta, and delta bands (Riekkinen et al., "EEG in the Diagnosis of Early Alzheimer's Disease," Alzheimer's Disease, Current Research in Early Diagnosis, Becker and Giacobini (eds.), pp. 159-167, 1990) for diagnosis of Alzheimer's Disease.

One can also diagnose Alzheimer's Disease by quantifying the degree of neural atrophy, since such atrophy is generally accepted as a consequence of Alzheimer's Disease. Examples of these methods include computed tomographic scanning (CT), and magnetic resonance imaging (MRI) (Leedom and Miller, "CT, MRI, and NMR Spectroscopy in Alzheimer's Disease," Alzheimer's Disease, Current Research in Early Diagnosis, Becker and Giacobini (eds.), pp. 297-313, 1990).

One can also diagnose Alzheimer's Disease by assessing decreased cerebral blood flow or metabolism in the posterior temporoparietal cerebral cortex by measuring decreased blood flow or metabolism by positron emission tomography (PET) (Parks and Becker, "Positron Emission Tomography and Neuropsychological Studies in Dementia," Alzheimer's Disease's, Current Research in Early Diagnosis, Becker and Giacobini (eds.), pp. 315-327, 1990), single photon emission computed tomography (SPECT) (Mena et al., "SPECT Studies in Alzheimer's Type Dementia Patients," Alzheimer's Disease, Current Research in Early Diagnosis, Becker and Giacobini (eds.), pp. 339-355, 1990), and xenon inhalation methods (Jagust et al., Neurology 38:909-912; Prohovnik et al., Neurology 38:931-937; and Waldemar et al., Senile Dementias: II International Symposium, pp. 399407, 1988).

One can also immunologically diagnose Alzheimer's disease (Wolozin, "Immunochemical Approaches to the Diagnosis of Alzheimer's Disease," Alzheimer's Disease, Current Research in Early Diagnosis, Becker and Giacobini (eds.), pp. 217-235, 1990). Wolozin and coworkers (Wolozin et al., Science 232:648-650, 1986) produced a monoclonal antibody "Alz50," that reacts with a 68-kDa protein "A68," which is expressed in the plaques and neuron tangles of patients with Alzheimer's disease. Using the antibody Alz50 and Western blot analysis, A68 was detected in the cerebral spinal fluid (CSF) of some Alzheimer's patients and not in the CSF of normal elderly patients (Wolozin and Davies, Ann. Neurol. 22:521-526, 1987).

One can also diagnose Alzheimer's disease using neurochemical markers of Alzheimer's disease. Neurochemical markers which have been associated with Alzheimer's Disease include reduced levels of acetylcholinesterase (Giacobini and Sugaya, "Markers of Cholinergic Dysfunction in Alzheimer's Disease," Alzheimer's Disease, Current Research in Early Diagnosis, Becker and Giacobini (eds.), pp. 137-156, 1990), reduced somatostatin (Tamminga et al., Neurology 37:161-165, 1987), a negative relation between serotonin and 5-hydroxyindoleacetic acid (Volicer et al., Arch Neurol. 42:127-129, 1985), greater probenecid-induced rise in homovanyllic acid (Gibson et al., Arch. Neurol. 42:489-492, 1985) and reduced neuron-specific enolase (Cutler et al., Arch. Neurol. 43:153-154, 1986).

Methods to Identify Subjects for Risk of or Having Down Syndrome

Down syndrome, also referred to as Trisomy 21, is the most common congenital cause of severe mental retardation. Down syndrome patients are usually diagnosed at birth, due to the characteristic physical features associated with trisomy 21. The physical phenotype of DS includes microcephaly, upward slanting eyes, broad neck, and hands that are small with in-curving fifth finger and a solitary simian crease across the palm. DS individuals are significantly shorter than the non-DS population, with an average height for adult males of around 5 feet and around 4.5 feet for females.

Neuropsychologically, individuals with DS display disproportionately impaired speech and expressive language skills, especially in articulation, phonology, and expressive syntax (Fowler, in Cicchetti & Beeghly eds., Children with Down Syndrome: A developmental perspective (pp. 302-328) New York: Cambridge University Press, 1990) and deficits in verbal short-term memory (Marcell & Armstrong, Am J Mental Deficiency 87:86-95 (1982); Varnhagen et al., Am J Mental Deficiency 91:398-405 (1987)). Imaging of DS patients shows they typically have reduced brain size (about 76% of normal) and reduced complexity of the convolutional pattern (Coyle et al., Brain Res Bull 16:773-87 (1986); Wisniewski, Am J Med Genet 7:274-81 (1990)). Small frontal lobes, a small operculum, a narrow superior temporal gyrus, and reduced volume of the hippocampus, cerebellum, and brainstem are typical.

One can also diagnose Down syndrome using diagnostic markers of Down syndrome such as those disclosed in US20130261020, WO2014051522, CA2739315, the contents of each of which are incorporated by reference in its entirety.

It should be understood that this invention is not limited to the particular methodology, protocols, and reagents, etc., disclosed herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although any known methods, devices, and materials may be used in the practice or testing of the invention, the methods, devices, and materials in this regard are disclosed herein.

Some embodiments of the invention are listed in the following paragraphs:

1. A method of treating a neurodegenerative disorder in a subject, the method comprising administering to the subject in need thereof an effective amount of an agent that inhibits or reduces translation of amyloid precursor protein, wherein the agent is a compound of Formula A or B, or a pharmaceutically acceptable salt thereof.

2. The method of paragraph 1, wherein the agent is a compound of Formula C or D, or a pharmaceutically acceptable salt thereof.

3. The method of paragraph 2, wherein the agent is selected from a compound of Formulas I-XII, or a pharmaceutically acceptable salt thereof.

4. The method of paragraph 3, wherein the agent is a compound of Formula I or XII, or a pharmaceutically acceptable salt thereof.

5. The method of any of paragraphs 1 to 4, wherein the neurodegenerative disorder is selected from the group consisting of Alzheimer's disease, Down syndrome, Parkinson's disease, Huntington's Disease, Amyotrophic Lateral Sclerosis (also termed Lou Gehrig's disease) and Multiple Sclerosis.

6. The method of paragraph 5, wherein the neurodegenerative disorder is Alzheimer's disease or Down syndrome.

7. The method of any of paragraphs 1 to 6, wherein the subject is a mammal.

8. The method of paragraph 7, wherein the mammal is a human.

9. A method of decreasing amyloid-beta production in a subject's brain, the method comprising administering to the subject in need thereof an effective amount of an agent that inhibits or reduces translation of amyloid precursor protein, wherein the agent is a compound of Formula A or B, or a pharmaceutically acceptable salt thereof.

10. The method of paragraph 9, wherein the agent is a compound of Formula C or D, or a pharmaceutically acceptable salt thereof.

11. The method of paragraph 10, wherein the agent is selected from a compound of Formulas I-XII, or a pharmaceutically acceptable salt thereof.

12. The method of paragraph 11, wherein the agent is a compound of Formula I or XII, or a pharmaceutically acceptable salt thereof.

13. The method of any of paragraphs 9 to 12, wherein the subject is in need for treating a neurodegenerative disorder.

14. The method of paragraph 13, wherein the neurodegenerative disorder is selected from the group consisting of Alzheimer's disease, Down syndrome, Parkinson's disease, Huntington's Disease, Amyotrophic Lateral Sclerosis (also termed Lou Gehrig's disease) and Multiple Sclerosis.

15. The method of paragraph 14, wherein the neurodegenerative disorder is Alzheimer's disease or Down syndrome.

16. The method of any of paragraphs 9-15, wherein the subject is a mammal.

17. The method of paragraph 16, wherein the mammal is a human.

18. The method of any of paragraphs 9-17, wherein amyloid-beta is Aβ-42.

19. A method of restoring or maintaining iron homeostasis in a subject's brain, the method comprising administering to the subject in need thereof an effective amount of an agent that inhibits or reduces translation of amyloid precursor protein, wherein the agent is a compound of Formula A or B, or a pharmaceutically acceptable salt thereof.

20. The method of paragraph 19, wherein the agent is a compound of Formula C or D, or a pharmaceutically acceptable salt thereof.

21. The method of paragraph 20, wherein the agent is selected from a compound of Formulas I-XII, or a pharmaceutically acceptable salt thereof.

22. The method of paragraph 21, wherein the agent is a compound of Formula I or XII, or a pharmaceutically acceptable salt thereof.

23. The method of any of paragraphs 19-22, wherein the subject is a mammal.

24. The method of paragraph 23, wherein the mammal is a human.

25. The method of paragraph 24, wherein the human has a neurodegenerative disorder.

26. Use of an agent which inhibits or reduces translation of amyloid precursor protein for the preparation of a medicament for treatment or prevention of a neurodegenerative disorder.

27. The use of paragraph 26, wherein the agent is a compound of Formula A or B, or a pharmaceutically acceptable salt thereof.

28. The use of paragraph 27, wherein the agent is a compound of Formula C or D, or a pharmaceutically acceptable salt thereof.

29. The use of paragraph 28, wherein the agent is selected from a compound of Formulas I-XII, or a pharmaceutically acceptable salt thereof.

30. The use of paragraph 29, wherein the agent is a compound of Formula I or XII, or a pharmaceutically acceptable salt thereof.

DEFINITIONS

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are useful to an embodiment, yet open to the inclusion of unspecified elements, whether useful or not.

As used herein the term "consisting essentially of" refers to those elements required for a given embodiment. The term permits the presence of elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise.

The term "disease", "disorder" is used interchangeably herein, refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, disorder, sickness, illness, complaint, affectation.

The terms "decrease", "reduce", or "inhibit" are all used herein to mean a decrease by a statistically significant amount. In some embodiments, the terms "decrease", "reduce", or "inhibit" can mean a decrease by at least 10% as compared to the concentration of APP or amyloid-beta before administration of the agent disclosed herein, for example a decrease by at least about 20%, or at least about 30%, or at least about 40%, or at least about 50%, or at least about 60%, or at least about 70%, or at least about 80%, or up to between about 90-95% or 90-99% decrease or any decrease of at least 10%-95% or 10-99% as compared to the concentration of APP or amyloid-beta before administration of the agent disclosed herein.

As used herein, the term "administer" refers to the placement of a composition into a subject by a method or route which results in at least partial localization of the composition at a desired site such that desired effect is produced. A compound or composition disclosed herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the compositions are administered by intravenous infusion or injection. In some embodiments, the compound is administered directly into the central nervous system.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin;

(7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The phrase "therapeutically-effective amount" or "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. For example, an amount of a compound administered to a subject that is sufficient to produce a statistically significant, measurable change in at least one symptom of a neurodegenerative disorder.

By "treatment", "prevention" or "amelioration" of a condition, disease, or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, at least one symptom of a disease or disorder is alleviated by at least 5%, at least 10%, at least 20%, at least 30%, at least 40%, or at least 50%.

The term "treatment", with respect to treatment of Alzheimer's disease, Down syndrome, or a disease associated with Aβ accumulation or aggregation refers to, inter alia, preventing the development of the disease, or altering the course of the disease (for example, but not limited to, slowing the progression of the disease), or reversing a symptom of the disease or reducing one or more symptoms and/or one or more biochemical markers in a subject, preventing one or more symptoms from worsening or progressing, promoting recovery or improving prognosis, and/or preventing disease in a subject who is free therefrom as well as slowing or reducing progression of existing disease. For a given subject, improvement in a symptom, its worsening, regression, or progression can be determined by an objective or subjective measure. For example, but not limited to, a reduction in a biochemical marker of Alzheimer's disease or Down syndrome, for example a reduction in APP production by 10%, or a reduction in the activation of glial cells, for example a reduction in cells expressing GFAP by 10%, would be considered effective treatments by the methods as disclosed herein. As alternative examples, a reduction in a symptom, for example, a slowing of the rate of memory loss by 10% or a cessation of the rate memory decline, or a reduction in memory loss by 10% or an improvement in memory by 10% would also be considered as affective treatments by the methods as disclosed herein.

Further, as used herein, the terms "treat" or "treatment" refer to both therapeutic treatment and prophylactic or preventative measures, wherein the object is to prevent or slow down (lessen) an undesired physiological change or disorder, such as the progression of Alzheimer's disease. Beneficial or desired clinical results can include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. Any particular treatment regimen can provide one or more such clinical results in one or more patients, and need not provide all such clinical results. "Treatment" can also mean prolonging survival as compared to expected survival if not receiving treatment. Those in need of treatment include those already with the condition or disorder as well as those prone to have the condition or disorder or those in which the condition or disorder is to be prevented.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein. The terms, "patient" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used as subjects that represent animal models of neuro-inflammatory disorders.

Certain compounds of the present invention and definitions of specific functional groups are also described in more detail below. For purposes of this invention, the chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

As used herein, the term "aliphatic" means a moiety characterized by a straight or branched chain arrangement of constituent carbon atoms and can be saturated or partially unsaturated with one or more (e.g., one, two, three, four, five or more) double or triple bonds.

As used herein, the term "alicyclic" means a moiety comprising a nonaromatic ring structure. Alicyclic moieties can be saturated or partially unsaturated with one or more double or triple bonds. Alicyclic moieties can also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with $C_3$-$C_8$ rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

As used herein, the term "alkyl" means a straight or branched, saturated aliphatic radical having a chain of carbon atoms. $C_x$ alkyl and $C_x$-$C_y$alkyl are typically used where X and Y indicate the number of carbon atoms in the chain. For example, $C_1$-$C_6$alkyl includes alkyls that have a chain of between 1 and 6 carbons (e.g., methyl, ethyl, propyl, isopropyl, butyl, sec-butyl, isobutyl, tert-butyl, pentyl, neopentyl, hexyl, and the like). Alkyl represented along with another radical (e.g., as in arylalkyl) means a straight or branched, saturated alkyl divalent radical having the number of atoms indicated or when no atoms are indicated means a bond, e.g., ($C_6$-$C_{10}$)aryl($C_0$-$C_3$)alkyl includes phenyl, benzyl, phenethyl, 1-phenylethyl 3-phenylpropyl, and the like. Backbone of the alkyl can be optionally inserted with one or more heteroatoms, such as N, O, or S.

In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. In some embodiments, a straight chain or branched chain alkyl has 5 or fewer carbon atoms, 10 or fewer carbon atoms, or 15 or fewer carbon atoms.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

Substituents of a substituted alkyl can include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF3, —CN and the like.

As used herein, the term "alkenyl" refers to unsaturated straight-chain, branched-chain or cyclic hydrocarbon radicals having at least one carbon-carbon double bond. $C_x$ alkenyl and $C_x$-$C_y$alkenyl are typically used where X and Y indicate the number of carbon atoms in the chain. For example, $C_2$-$C_6$alkenyl includes alkenyls that have a chain of between 1 and 6 carbons and at least one double bond, e.g., vinyl, allyl, propenyl, isopropenyl, 1-butenyl, 2-butenyl, 3-butenyl, 2-methylallyl, 1-hexenyl, 2-hexenyl, 3-hexenyl, and the like). Alkenyl represented along with another radical (e.g., as in arylalkenyl) means a straight or branched, alkenyl divalent radical having the number of atoms indicated. Backbone of the alkenyl can be optionally inserted with one or more heteroatoms, such as N, O, or S.

As used herein, the term "alkynyl" refers to unsaturated hydrocarbon radicals having at least one carbon-carbon triple bond. $C_x$ alkynyl and $C_x$-$C_y$alkynyl are typically used where X and Y indicate the number of carbon atoms in the chain. For example, $C_2$-$C_6$alkynyl includes alkynls that have a chain of between 1 and 6 carbons and at least one triple bond, e.g., ethynyl, 1-propynyl, 2-propynyl, 1-butynyl, isopentynyl, 1,3-hexa-diyn-yl, n-hexynyl, 3-pentynyl, 1-hexen-3-ynyl and the like. Alkynyl represented along with another radical (e.g., as in arylalkynyl) means a straight or branched, alkynyl divalent radical having the number of atoms indicated. Backbone of the alkynyl can be optionally inserted with one or more heteroatoms, such as N, O, or S.

The terms "alkylene," "alkenylene," and "alkynylene" refer to divalent alkyl, alkelyne, and alkynylene" radicals. Prefixes $C_x$ and $C_x$-$C_y$ are typically used where X and Y indicate the number of carbon atoms in the chain. For example, $C_1$-$C_6$alkylene includes methylene, (—$CH_2$—), ethylene (—$CH_2CH_2$—), trimethylene (—$CH_2CH_2CH_2$—), tetramethylene (—$CH_2CH_2CH_2CH_2$—), 2-methyltetramethylene (—$CH_2CH(CH_3)CH_2CH_2$—), pentamethylene (—$CH_2CH_2CH_2CH_2CH_2$—) and the like).

As used herein, the term "alkylidene" means a straight or branched unsaturated, aliphatic, divalent radical having a general formula=$CR_aR_b$. $C_x$ alkylidene and $C_x$-$C_y$alkylidene are typically used where X and Y indicate the number of carbon atoms in the chain. For example, $C_2$-$C_6$alkylidene includes methylidene (=$CH_2$), ethylidene (=$CHCH_3$), isopropylidene (=$C(CH_3)_2$), propylidene (=$CHCH_2CH_3$), allylidene (=$CH$—$CH$=$CH_2$), and the like).

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups. In some embodiments, the heteroalkyl has 5 or fewer carbon atoms, 10 or fewer carbon atoms, or 15 or fewer carbon atoms.

As used herein, the term "halogen" or "halo" refers to an atom selected from fluorine, chlorine, bromine and iodine.

A "halogen-substituted moiety" or "halo-substituted moiety", as an isolated group or part of a larger group, means an aliphatic, alicyclic, or aromatic moiety, as described herein, substituted by one or more "halo" atoms, as such terms are defined in this application. For example, halo-substituted alkyl includes haloalkyl, dihaloalkyl, trihaloalkyl, perhaloalkyl and the like (e.g. halosubstituted ($C_1$-$C_3$)alkyl includes chloromethyl, dichloromethyl, difluoromethyl, trifluoromethyl (—$CF_3$), 2,2,2-trifluoroethyl, perfluoroethyl, 2,2,2-trifluoro-1,1-dichloroethyl, and the like).

The term "aryl" refers to monocyclic, bicyclic, or tricyclic fused aromatic ring system. $C_x$ aryl and $C_x$-$C_y$aryl are typically used where X and Y indicate the number of carbon atoms in the ring system. An aryl group can comprise a 4-atom ring, a 5-atom ring, a 6-atom ring, a 7-atom ring, a 8-atom ring, a 9 atom ring, or more. Exemplary aryl groups include, but are not limited to, pyridinyl, pyrimidinyl, furanyl, thienyl, imidazolyl, thiazolyl, pyrazolyl, pyridazinyl, pyrazinyl, triazinyl, tetrazolyl, indolyl, benzyl, phenyl, naphthyl, anthracenyl, azulenyl, fluorenyl, indanyl, indenyl, naphthyl, phenyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl, and the like. In some embodiments, 1, 2, 3, or 4 hydrogen atoms of each ring can be substituted by a substituent.

The term "heteroaryl" refers to an aromatic 5-8 membered monocyclic, 8-12 membered fused bicyclic, or 11-14 membered fused tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively. $C_x$ heteroaryl and $C_x$-$C_y$heteroaryl are typically used where X and Y indicate the number of carbon atoms in the ring system. Heteroaryls include, but are not limited to, those derived from benzo[b]furan, benzo[b] thiophene, benzimidazole, imidazo[4,5-c]pyridine, quinazoline, thieno[2,3-c]pyridine, thieno[3,2-b]pyridine, thieno[2, 3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3cj pyridine, pyrrolo[3,2-c]pyridine, pyrrolo[3,2-b]pyridine, pyrrolo[2,3-d]pyrimidine, pyrrolo[3,2-d]pyrimidine, pyrrolo [2,3-b]pyrazine, pyrazolo [1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole, 2(1H)-pyridinone, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Some exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, 2-amino-4-oxo-3,4-dihydropteridin-6-yl, tetrahydroisoquinolinyl, and the like. In some embodiments, 1, 2, 3, or 4 hydrogen atoms of each ring may be substituted by a substituent.

The term "cyclyl" or "cycloalkyl" refers to saturated and partially unsaturated cyclic hydrocarbon groups having 3 to 12 carbons, for example, 3 to 8 carbons, and, for example, 3 to 6 carbons. $C_x$cyclyl and $C_x$-$C_y$cylcyl are typically used where X and Y indicate the number of carbon atoms in the ring system. The cycloalkyl group additionally can be optionally substituted, e.g., with 1, 2, 3, or 4 substituents. $C_3$-$C_{10}$cyclyl includes cyclopropyl, cyclobutyl, cyclopentyl, cyclohexyl, cyclohexenyl, 2,5-cyclohexadienyl, cycloheptyl, cyclooctyl, bicyclo[2.2.2]octyl, adamantan-1-yl, decahydronaphthyl, oxocyclohexyl, dioxocyclohexyl, thiocyclohexyl, 2-oxobicyclo [2.2.1]hept-1-yl, and the like.

Aryl and heteroaryls can be optionally substituted with one or more substituents at one or more positions, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF3, —CN, or the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$heterocyclyl and $C_x$-$C_y$heterocyclyl are typically used where X and Y indicate the number of carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyland the like.

The terms "bicyclic" and "tricyclic" refers to fused, bridged, or joined by a single bond polycyclic ring assemblies.

The term "cyclylalkylene" means a divalent aryl, heteroaryl, cyclyl, or heterocyclyl.

As used herein, the term "fused ring" refers to a ring that is bonded to another ring to form a compound having a bicyclic structure when the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems can be saturated, partially saturated, cyclyl, heterocyclyl, aromatics, heteroaromatics, and the like.

As used herein, the term "carbonyl" means the radical —C(O)—. It is noted that the carbonyl radical can be further substituted with a variety of substituents to form different carbonyl groups including acids, acid halides, amides, esters, ketones, and the like.

The term "carboxy" means the radical —C(O)O—. It is noted that compounds described herein containing carboxy moieties can include protected derivatives thereof, i.e., where the oxygen is substituted with a protecting group. Suitable protecting groups for carboxy moieties include benzyl, tert-butyl, and the like. The term "carboxyl" means —COOH The term "cyano" means the radical —CN.

The term, "heteroatom" refers to an atom that is not a carbon atom. Particular examples of heteroatoms include, but are not limited to nitrogen, oxygen, sulfur and halogens. A "heteroatom moiety" includes a moiety where the atom by which the moiety is attached is not a carbon. Examples of heteroatom moieties include —N=, —NR$^N$—, —N$^+$(O$^-$)=, —O—, —S— or —S(O)$_2$—, —OS(O)$_2$—, and —SS—, wherein R$^N$ is H or a further substituent.

The term "hydroxy" means the radical —OH.

The term "imine derivative" means a derivative comprising the moiety —C(NR)—, wherein R comprises a hydrogen or carbon atom alpha to the nitrogen.

The term "nitro" means the radical —NO$_2$.

An "oxaaliphatic," "oxaalicyclic", or "oxaaromatic" mean an aliphatic, alicyclic, or aromatic, as defined herein, except where one or more oxygen atoms (—O—) are positioned between carbon atoms of the aliphatic, alicyclic, or aromatic respectively.

An "oxoaliphatic," "oxoalicyclic", or "oxoaromatic" means an aliphatic, alicyclic, or aromatic, as defined herein, substituted with a carbonyl group. The carbonyl group can be an aldehyde, ketone, ester, amide, acid, or acid halide.

As used herein, the term, "aromatic" means a moiety wherein the constituent atoms make up an unsaturated ring system, all atoms in the ring system are sp$^2$ hybridized and the total number of pi electrons is equal to 4n+2. An aromatic ring canbe such that the ring atoms are only carbon atoms (e.g., aryl) or can include carbon and non-carbon atoms (e.g., heteroaryl).

As used herein, the term "substituted" refers to independent replacement of one or more (typically 1, 2, 3, 4, or 5) of the hydrogen atoms on the substituted moiety with substituents independently selected from the group of substituents listed below in the definition for "substituents" or otherwise specified. In general, a non-hydrogen substituent can be any substituent that can be bound to an atom of the given moiety that is specified to be substituted. Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, alkylcarbanoyl, alkylene, alkylidene, alkylthios, alkynyl, amide, amido, amino, amino, aminoalkyl, aralkyl, aralkylsulfonamido, arenesulfonamido, arenesulfonyl, aromatic, aryl, arylamino, arylcarbanoyl, aryloxy, azido, carbamoyl, carbonyl, carbonyls (including ketones, carboxy, carboxylates, CF$_3$, cyano (CN), cycloalkyl, cycloalkylene, ester, ether, haloalkyl, halogen, halogen, heteroaryl, heterocyclyl, hydroxy, hydroxy, hydroxyalkyl, imino, iminoketone, ketone, mercapto, nitro, oxaalkyl, oxo, oxoalkyl, phosphoryl (including phosphonate and phosphinate), silyl groups, sulfonamido, sulfonyl (including sulfate, sulfamoyl and sulfonate), thiols, and ureido moieties, each of which may optionally also be substituted or unsubstituted. In some cases, two substituents, together with the carbon(s) to which they are attached to, can form a ring.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy, n-propyloxy, isopropyloxy, n-butyloxy, iso-butyloxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The term "aralkyl", as used herein, refers to an alkyl group substituted with an aryl group (e.g., an aromatic or heteroaromatic group).

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups.

The term "sulfinyl" means the radical —SO—. It is noted that the sulfinyl radical can be further substituted with a variety of substituents to form different sulfinyl groups including sulfinic acids, sulfinamides, sulfinyl esters, sulfoxides, and the like.

The term "sulfonyl" means the radical —SO$_2$—. It is noted that the sulfonyl radical can be further substituted with a variety of substituents to form different sulfonyl groups including sulfonic acids (—SO$_3$H), sulfonamides, sulfonate esters, sulfones, and the like.

The term "thiocarbonyl" means the radical —C(S)—. It is noted that the thiocarbonyl radical can be further substituted with a variety of substituents to form different thiocarbonyl groups including thioacids, thioamides, thioesters, thioketones, and the like.

As used herein, the term "amino" means —NH$_2$. The term "alkylamino" means a nitrogen moiety having at least one straight or branched unsaturated aliphatic, cyclyl, or heterocyclyl radicals attached to the nitrogen. For example, representative amino groups include —NH$_2$, —NHCH$_3$, —N(CH$_3$)$_2$, —NH(C$_1$-C$_{10}$alkyl), —N(C$_1$-C$_{10}$alkyl)$_2$, and the like. The term "alkylamino" includes "alkenylamino," "alkynylamino," "cyclylamino," and "heterocyclylamino." The term "arylamino" means a nitrogen moiety having at least one aryl radical attached to the nitrogen. For example —NHaryl, and —N(aryl)$_2$. The term "heteroarylamino" means a nitrogen moiety having at least one heteroaryl radical attached to the nitrogen. For example —NHheteroaryl, and —N(heteroaryl)$_2$. Optionally, two substituents together with the nitrogen can also form a ring. Unless indicated otherwise, the compounds described herein containing amino moieties can include protected derivatives thereof. Suitable protecting groups for amino moieties include acetyl, tertbutoxycarbonyl, benzyloxycarbonyl, and the like.

The term "aminoalkyl" means an alkyl, alkenyl, and alkynyl as defined above, except where one or more substituted or unsubstituted nitrogen atoms (—N—) are positioned between carbon atoms of the alkyl, alkenyl, or alkynyl. For example, an ($C_2$-$C_6$) aminoalkyl refers to a chain comprising between 2 and 6 carbons and one or more nitrogen atoms positioned between the carbon atoms.

The term "alkoxyalkoxy" means —O-(alkyl)-O-(alkyl), such as —OCH$_2$CH$_2$OCH$_3$, and the like.

The term "alkoxycarbonyl" means —C(O)O-(alkyl), such as —C(=O)OCH$_3$, —C(=O)OCH$_2$CH$_3$, and the like.

The term "alkoxyalkyl" means -(alkyl)-O-(alkyl), such as —CH$_2$OCH$_3$, —CH$_2$OCH$_2$CH$_3$, and the like.

The term "aryloxy" means —O-(aryl), such as —O-phenyl, —O-pyridinyl, and the like.

The term "arylalkyl" means -(alkyl)-(aryl), such as benzyl (i.e., —CH$_2$phenyl), —CH$_2$— pyrindinyl, and the like.

The term "arylalkyloxy" means —O-(alkyl)-(aryl), such as —O-benzyl, —O—CH$_2$-pyridinyl, and the like.

The term "cycloalkyloxy" means —O-(cycloalkyl), such as —O-cyclohexyl, and the like.

The term "cycloalkylalkyloxy" means —O-(alkyl)-(cycloalkyl, such as —OCH$_2$cyclohexyl, and the like.

The term "aminoalkoxy" means —O-(alkyl)-NH$_2$, such as —OCH$_2$NH$_2$, —OCH$_2$CH$_2$NH$_2$, and the like.

The term "mono- or di-alkylamino" means —NH(alkyl) or —N(alkyl)(alkyl), respectively, such as —NHCH$_3$, —N(CH$_3$)$_2$, and the like.

The term "mono- or di-alkylaminoalkoxy" means —O-(alkyl)-NH(alkyl) or —O-(alkyl)-N(alkyl)(alkyl), respectively, such as —OCH$_2$NHCH$_3$, —OCH$_2$CH$_2$N(CH$_3$)$_2$, and the like.

The term "arylamino" means —NH(aryl), such as —NH-phenyl, —NH-pyridinyl, and the like.

The term "arylalkylamino" means —NH-(alkyl)-(aryl), such as —NH-benzyl, —NHCH$_2$— pyridinyl, and the like.

The term "alkylamino" means —NH(alkyl), such as —NHCH$_3$, —NHCH$_2$CH$_3$, and the like.

The term "cycloalkylamino" means —NH-(cycloalkyl), such as —NH-cyclohexyl, and the like.

The term "cycloalkylalkylamino"-NH-(alkyl)-(cycloalkyl), such as —NHCH$_2$— cyclohexyl, and the like.

It is noted in regard to all of the definitions provided herein that the definitions should be interpreted as being open ended in the sense that further substituents beyond those specified may be included. Hence, a $C_1$ alkyl indicates that there is one carbon atom but does not indicate what are the substituents on the carbon atom. Hence, a $C_1$ alkyl comprises methyl (i.e., —CH3) as well as —CR$_a$R$_b$R$_c$ where R$_a$, R$_b$, and R$_c$ caneach independently be hydrogen or any other substituent where the atom alpha to the carbon is a heteroatom or cyano. Hence, CF$_3$, CH$_2$OH and CH$_2$CN are all $C_1$ alkyls.

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

As used here in the term "isomer" refers to compounds having the same molecular formula but differing in structure. Isomers which differ only in configuration and/or conformation are referred to as "stereoisomers." The term "isomer" is also used to refer to an enantiomer.

The term "enantiomer" is used to describe one of a pair of molecular isomers which are mirror images of each other and non-superimposable. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate planepolarized light in different directions). Enantiomers generally have identical physical properties, such as melting points and boiling points, and also have identical spectroscopic properties. Enantiomers can differ from each other with respect to their interaction with plane-polarized light and with respect to biological activity.

The designations "R and S" are used to denote the absolute configuration of the molecule about its chiral center(s). The designations may appear as a prefix or as a suffix; they may or may not be separated from the isomer by a hyphen; they may or may not be hyphenated; and they may or may not be surrounded by parentheses.

The designations or prefixes "(+) and (−)" are employed to designate the sign of rotation of plane-polarized light by the compound, with (−) meaning that the compound is levorotatory (rotates to the left). A compound prefixed with (+) is dextrorotatory (rotates to the right).

The term "racemic mixture," "racemic compound" or "racemate" refers to a mixture of the two enantiomers of one compound. An ideal racemic mixture is one wherein there is a 50:50 mixture of both enantiomers of a compound such that the optical rotation of the (+) enantiomer cancels out the optical rotation of the (−) enantiomer.

The term "resolving" or "resolution" when used in reference to a racemic mixture refers to the separation of a racemate into its two enantiomorphic forms (i.e., (+) and (−); (R) and (S) forms). The terms can also refer to enantioselective conversion of one isomer of a racemate to a product.

The term "enantiomeric excess" or "ee" refers to a reaction product wherein one enantiomer is produced in excess of the other, and is defined for a mixture of (+)- and (−)-enantiomers, with composition given as the mole or weight or volume fraction $F_{(+)}$ and $F_{(−)}$ (where the sum of $F_{(+)}$ and $F_{(−)}$=1). The enantiomeric excess is defined as $*F_{(+)}−F_{(−)}*$ and the percent enantiomeric excess by $100 \times *F_{(+)}−F_{(−)}*$. The "purity" of an enantiomer is described by its ee or percent ee value (% ee).

Whether expressed as a "purified enantiomer" or a "pure enantiomer" or a "resolved enantiomer" or "a compound in enantiomeric excess", the terms are meant to indicate that the amount of one enantiomer exceeds the amount of the other. Thus, when referring to an enantiomer preparation, both (or either) of the percent of the major enantiomer (e.g. by mole or by weight or by volume) and (or) the percent enantiomeric excess of the major enantiomer may be used to determine whether the preparation represents a purified enantiomer preparation.

The term "enantiomeric purity" or "enantiomer purity" of an isomer refers to a qualitative or quantitative measure of the purified enantiomer; typically, the measurement is expressed on the basis of ee or enantiomeric excess.

The terms "substantially purified enantiomer," "substantially resolved enantiomer" "substantially purified enantiomer preparation" are meant to indicate a preparation (e.g. derived from non optically active starting material, substrate, or intermediate) wherein one enantiomer has been enriched over the other, and more preferably, wherein the other enantiomer represents less than 20%, more preferably less than 10%, and more preferably less than 5%, and still more preferably, less than 2% of the enantiomer or enantiomer preparation.

The terms "purified enantiomer," "resolved enantiomer" and "purified enantiomer preparation" are meant to indicate a preparation (e.g. derived from non optically active starting material, substrates or intermediates) wherein one enantiomer (for example, the R-enantiomer) is enriched over the other, and more preferably, wherein the other enantiomer (for example the S-enantiomer) represents less than 30%, preferably less than 20%, more preferably less than 10% (e.g. in this particular instance, the R-enantiomer is substantially free of the S-enantiomer), and more preferably less than 5% and still more preferably, less than 2% of the preparation. A purified enantiomer may be synthesized substantially free of the other enantiomer, or a purified enantiomer may be synthesized in a stereopreferred procedure, followed by separation steps, or a purified enantiomer may be derived from a racemic mixture.

The term "enantioselectivity," also called the enantiomeric ratio indicated by the symbol "E," refers to the selective capacity of an enzyme to generate from a racemic substrate one enantiomer relative to the other in a product racemic mixture; in other words, it is a measure of the ability of the enzyme to distinguish between enantiomers. A nonselective reaction has an E of 1, while resolutions with E's above 20 are generally considered useful for synthesis or resolution. The enantioselectivity resides in a difference in conversion rates between the enantiomers in question. Reaction products are obtained that are enriched in one of the enantiomers; conversely, remaining substrates are enriched in the other enantiomer. For practical purposes it is generally desirable for one of the enantiomers to be obtained in large excess. This is achieved by terminating the conversion process at a certain degree of conversion.

The term "analog" as used herein refers to a compound that results from substitution, replacement or deletion of various organic groups or hydrogen atoms from a parent compound. As such, some monoterpenoids can be considered to be analogs of monoterpenes, or in some cases, analogs of other monoterpenoids, including derivatives of monoterpenes. An analog is structurally similar to the parent compound, but can differ by even a single element of the same valence and group of the periodic table as the element it replaces.

The term "derivative" as used herein refers to a chemical substance related structurally to another, i.e., an "original" substance, which can be referred to as a "parent" compound. A "derivative" can be made from the structurally-related parent compound in one or more steps. The phrase "closely related derivative" means a derivative whose molecular weight does not exceed the weight of the parent compound by more than 50%. The general physical and chemical properties of a closely related derivative are also similar to the parent compound.

As used herein, the term "pharmaceutically-acceptable salts" refers to the conventional nontoxic salts or quaternary ammonium salts of therapeutic agents, e.g., from non-toxic organic or inorganic acids. These salts can be prepared in situ in the administration vehicle or the dosage form manufacturing process, or by separately reacting a therapeutic agent in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", J. Pharm. Sci. 66:1-19 (1977), content of which is herein incorporated by reference in its entirety.

In some embodiments of the aspects described herein, representative salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

Although methods and materials similar or equivalent to those disclosed herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology disclosed herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are disclosed herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments disclosed herein can be combined to provide further embodiments. Aspects of the disclosure can be modified, if necessary, to employ the compositions, functions and concepts of the above references and application to provide yet further embodiments of the disclosure.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

The technology disclosed herein is further illustrated by the following examples which in no way should be construed as being further limiting.

Example 1: 5'Untranslated Region Directed Blockers of Iron-Regulatory Protein-I Dependent Amyloid Precursor Protein Translation: Implications for Down Syndrome and Alzheimer's Disease Here, thirteen potent APP translation blockers were identified that acted selectively towards the uniquely configured iron-responsive element (IRE) RNA stem loop in the 5' untranslated region (UTR) of APP mRNA. These agents were 10-fold less inhibitory of 5'UTR sequences of the related prion protein (PrP) mRNA. Western blotting confirmed that the 'ninth' small molecule in the series selectively reduced neural APP production in SH-SY5Y cells at picomolar concentrations without affecting viability or the expression of α-synuclein and ferritin. APP blocker-9 (JTR-009), a benzimidazoal, reduced the production of toxic Aβ in SH-SY5Y neuronal cells to a greater extent than other well tolerated APP 5'UTR-directed translation blockers, including posiphen, that were shown to limit amyloid burden in mouse models of Alzheimer's disease (AD). RNA binding assays demonstrated that JTR-009 operated by preventing IRP1 from binding to the IRE in APP mRNA, while maintaining IRP1 interaction with the H-ferritin IRE RNA stem loop. Thus, JTR-009 constitutively repressed translation driven by APP 5'UTR sequences. Calcein staining showed that JTR-009 did not indirectly change iron uptake in neuronal cells suggesting a direct interaction with the APP 5'UTR. These studies provide key data to develop small molecules that selectively reduce neural APP and Aβ production at 10-fold lower concentrations than related previously characterized translation blockers. The data presented herein evidenced a novel therapeutic strategy of potential impact for people with trisomy of the APP gene on chromosome 21, which is a phenotype long associated with Down syndrome (DS) that can also cause familial Alzheimer's disease.

Disclosed herein is a novel APP 5'UTR-specific translation blocker of neuronal APP and A3 that operates at nanomolar concentrations while maintaining β-actin expression and cell viability [9]. JTR-009 is a benzimidazole that was found to reduce intracellular APP and toxic Aβ production in both SH-SY5Y neural cell lines and primary mouse neurons. Here the inventors have shed light on the mechanism of action of JTR-009, which is consistent with the drug intercalating into RNA sequences folded from the APP 5'UTR and irreversibly replacing IRP1 as the repressor of APP translation. These findings supported the pharmacological goal to reduce APP expression with therapeutic implications particularly for DS and AD.

Materials and Methods

Antibodies

Rabbit anti-human IRP1 antibody (Alpha Diagnostics International, San Antonio, Tex.) and anti-IRP I each generated the same results in the assays shown; mouse anti-human IRP2 (Santa Cruz Biotechnology, Santa Cruz, Calif.) detected the H-ferritin IRE-IRP2 interaction, and a second antibody to IRP2 was also utilized to confirm the selectivity of IRP2 binding as detected with the Santa Cruz Biotechnology antibody. Anti-β-actin, anti-α-tubulin, rabbit anti-APP C-terminal antibody (A8717) were from (Sigma, St. Louis, Mo.), and the APP N-terminal antibody (22C1I) was from Chemicon (Temecula, Calif.).

Cell Culture and Preparation of Lysates

Human SH-SY5Y neuroblastoma cells were cultured in DMEM supplemented with 10% FBS (Invitrogen, Carlsbad, Calif.) and penicillin/streptomycin (Bio-Whittaker, Walkersville, Md.). Cells were exposed to JTR-009 (0-100 1.1M, Calbiochem) and iron (50 FM, National Institute of Standards and Technology (NIST), Gaithersburg, Md.), provided to cells as ferrous ammonium sulfate. Cytoplasmic protein lysates were prepared by homogenizing the cells in ribonucleoprotein inunnunoprecipitation buffer (25 mM Tris, pH 7.4, 1% Nonidet P-40, 0.5% sodium deoxycholate, 15 mM NaCl, protease inhibitors, RNase inhibitor, and 10 uM DTT). For preparation of conditioned medium for Aβ and LDH measurements, cells were treated for 48-72 hours with each compound as described in the legends. 1 mL was used for total Aβ determination by ELISA as described by Biosource International according to manufacturers conditions (see Ref [8]).

Primary cortical neurons from wild type mice and from the PAC-Tg(SNCA(wt) human SNCA genomic mice [22] were cultured as outlined by the method of Ray et al., 2009 [23]. The embryonic (E15-18) pups were recovered after sacrificing pregnant females, separated out the brain, and removed the meninges and blood vessels. The cortices were then dissected out and placed them in separate Eppendorf tubes containing 500 uL of HBSS without $Ca^{+2}/Mg^{+2}$ salts supplemented with 1 mM sodium pyruvate and 10 mM HEPES, pH 7.4. On ice, individual cells were isolated by titrating 10 times using a glass pasture pipette with the tip barely fire polished. The volume was adjusted to 1.5 mL, by adding 1 mL of HBSS with $Ca^{+2}/Mg^{+2}$ salts+Na. pyruvate+ HEPES, restoring the divalent cations by adding HBSS so that the non-dispersed tissue could settle for 5 min, on ice. In the tissue culture laminar hood, the supernatant was transferred into a new 15 mL tube and centrifuged for 1 minute at 900 rpm, 4° C. The pellet was gently re-suspended in 2 mL of HBSS with $Ca^{+2}/Mg^{+2}$ salts+Na pyruvate+ HEPES and took an aliquot for counting (2 mL for approx 5 embryos). The cells were then plated at ~$1 \times 10^5$ cells/well of a 24 well or $2 \times 10^5$/in 12 well plates. Each set of plates was coated with poly D-lysine containing poly L-lysine coverslips for micro immuncytochemical confirmation of neuronal integrity.

Methodology of Molecular Screens

The 110,000 compounds of the molecular library of LDDN at Harvard were screened to identify novel and more potent APP 5'UTR-directed inhibitors [21]. The LDDN library had already yielded small molecules that inhibit mesangial cell proliferation [24], following three-dimensional pharmacophore modeling and screening. A second Molecular Libraries Screening Centers Network HTS was conducted at the Columbia University Genome Center to generate hits as listed on PUBCHEM (AID: 1285), from which the dose-response assays identified 50 lead APP 5'UTR-directed luciferase reporter inhibitors. Two classes of APP 5'UTR-directed translation blockers from the second screen exhibited a potent $IC_{50}$ in the $10^{-8}$ M range. These were directly measured and found not to inhibit luciferase enzyme activity. A shortlist of the thirteen most selective APP 5'UTR inhibitors were pooled from both screens. These thirteen leads were tricyclic aromatic compounds that included two major classes of hits: compounds with a benzimidazole backbone, i.e. APP blockers 2, −7, and −9 (JTR-009) and compounds with a benzothiazole backbone, i.e. APP blockers −8 and −13. The compounds with a benzothiazole backbone were also identified to be similar to PFTα, another benzothiazole, and P53 inhibitor, by showing protection against oxidative injuries in synaptosomes from wild-type mice and preserving presynaptic terminals in cultured hippocampal neurons exposed to etoposide [25] [26]). The anti-APP 5'UTR efficacy of the 13 top inhibitors was directly compared with their anti-APP efficacy by Western blotting of lysates prepared from SH-SY5Y cells.

Western Blotting

After cells were exposed to increasing concentrations of the compounds as outlined in each figure legend, cytoplasmic protein lysates were prepared by homogenizing the cells in midRIPA buffer (25 mM Tris pH 7.4, 1% NP40, 0.5% sodium deoxycholate, 15 mM NaCl, protease inhibitors, RNase inhibitor and 10 μM DTT). Western blotting for APP was performed using the N-terminal 22C11 antibody (Millipore, Inc) and the A8717 C-terminal specific APP antibody (Sigma, inc), while αsyn was detected using mouse monoclonal anti-αsyn (BD Transduction Laboratories) and anti-β-actin (Chemicon). The blots were developed using chemiluminescence (PIERCE, Rockford, Ill.) and visualized with a Phosphoimager (BioRad, Hercules, Calif.). The bands were quantified using QuantityOne® software (BioRad).

RNA Quantification qRT-PCR was conducted to measure the capacity of JTR-009 to change steady state levels of APP inRNA levels, as was previously described (see Ref [6]). Desferrioxamine treatment was used for a positive control to assess changes to the steady state levels of both APP mRNA and transferrin receptor mRNAs. Primers for β-actin were employed as a control for an mRNA previously shown to be unchanged by desferrioxamine and other inducers [6]. Experiments were carried out on the ABI Prism 7000 sequence detection system (Applied Biosystems). Total RNA was isolated using TRIzol reagent (Sigma) according to the manufacturer's instructions. cDNA was synthesized with SuperScript III first-strand qPCR supermix (Invitrogen) according to the manufacturer's instructions. The primers to β-actin, TfR1 were designed and ordered from Invitrogen. The APP primer set was purchased from Qiagen and has been benchmarked on several reports for accurate measurement of APP mRNA levels.

Transfections and Luciferase Reporter Assays for Counterscreens

APP 5'UTR-Luciferase inhibitor compounds obtained from the preliminary HTS of pIRES-APP-5'UTR transfectants were picked, and the dose-response assays were conducted at 0.1, 1.0, and 5.0 μM (based on the exact molecular weights of the compounds). For the purpose of counter-screening, pIRES-PrP-5'UTR)-transfected SH-SY5Y cells were plated in 384-well black plates, and the identified compound hits that were not cytotoxic were manually added to the cells. Each hit was added in 5 wells, and this was repeated twice on 2 different days. There was a positive control and negative control column of cells as previously described [21]. The inhibition of luciferase was calculated, and the average of the values obtained was considered (see data shown in Table 1).

TABLE 1

$IC_{50}$ (nM) for APP 5'UTR Blockers in pIRES-APP-5'UTR and pIRES-PrP-5'UTR transfectants calculated from inhibition curves in 384-plate assays to reduce 5'UTR driven luciferase expression [21].

| Agent | 1 | 2 | 3 | 4 | 5 | 6 | 7 | 8 | 9 | 10 | 11 | 12 | 13 |
|---|---|---|---|---|---|---|---|---|---|---|---|---|---|
| $IC_{50}$ | 700 | 800 | 750 | 80 | 5000 | 1000 | 500 | 80 | 400 | 900 | 3,000 | 3000 | 100 |
| $IC_{50}$ | 700 | 5000 | 750 | 400 | 5000 | 1000 | 1000 | 80 | 4000 | 2000 | 10,000 | 7000 | 500 |

Biotinylated RNA Pulldown Assay

Biotinylated RNA oligonucleotides: H-ferritin IRE (biotin-5'-GGG UUU CCU GCU UCA ACAGUG CUU GGA CGG AAC CCG G-3' (SEQ ID NO: 18)) and APP IRE (5'-biotin-GC GGU GGC GGC GCG GGC AGA GCA AGG ACG CGG CGG AU-3' (SEQ ID NO: 19)) were purchased from Invitrogen. Cell lysates (100 μg) were incubated with 100 nM biotinylated oligonucleotide for each of the IREs, for 3 hours at room temperature. Paramagnetic streptavidin-conjugated Dynabeads (Invitrogen) were washed with ribonucleoprotein immunoprecipitation buffer, added into lysates to bind IRP(1/2)-biotinylated-RNA complexes, and incubated for 1 hour at room temperature. After five washes, the proteins that bound to the beads were analyzed by Western blotting for IRP1, IRP2, and biotin. The blots were developed with chemiluminescence (Pierce) and visualized with a 4000 MP VersaDoc™ Imaging System (Bio-Rad). The IREs-bound IRPs were quantified by Quantity One® software (Bio-Rad).

Calcein Assay

Cells were loaded with calcein after incubation with 0.1 μM of Calcein-AM for 10 min in 0.15 M NaCl-20 mM HEPES buffer, pH 7.4, with 0.1% BSA at 37° C., an action followed by extensive washing with NaCl-HEPES buffer to remove extracellular bound calcein. The cells were aliquoted at $5 \times 10^4$-$1 \times 10^5$ cells/well in 96-well plates containing test compounds at 10 μM and incubated for 30 min in a humidified 37° C. incubator with 5% $CO_2$ before baseline fluorescence was obtained at 485/520 nm (excitation/emission) with 0.1% DMSO, as the vehicle control, and DTPA as a strong iron chelator control to block all iron uptake. Using Using a SpectraMax M5 plate reader and SoftMax Pro software (Molecular Devices, Sunnyvale, Calif.), the fluorescence was then measured 30 min after the addition of 10 µM ferrous ammonium sulfate in 500 µM ascorbic acid (AA). The percentage of fluorescence quench was calculated relative to 200 µM DTPA, which was added as a blocking control, and DMSO as a vehicle control, as follows:

$$\Delta F = (F_0 - F_f)/F_0 \qquad (1)$$

where ΔF is the change in fluorescence, or fluorescence quench observed in any well. $F_0$ represents the fluorescence after 30 min of the compound, and $F_f$ represents the fluorescence 30 minutes after addition of Fe. These results were normalized to the blocking and vehicle controls as follows:

$$\Delta F_n = (F_{compound} - F_{min})/(F_{max} - F_{min}) \qquad (2)$$

where $\Delta F_n$ is the normalized quench observed after addition of iron. $F_{compound}$ is the ΔF observed with the compound, $F_{min}$ is the average ΔF of the DMSO control, and $F_{max}$ is the average ΔF of the DTPA control.

With this normalization, 100% indicates that the test compound is as potent as DTPA in blocking iron-induced quenching, and 0% indicates no inhibition of iron quenching by the test compound or the same quench as observed with the DMSO vehicle control. Compounds with $\Delta F_n$ between 0% and 100% are defined as inhibitors of iron uptake. Negative values for ΔF represents compounds that facilitate iron uptake into cells. The criteria for active compounds to be further investigated were arbitrarily set as $\Delta F_n = 50-100\%$ quenching for iron uptake inhibitors and $<-50\%$ quenching for iron uptake facilitators.

ELISA Measurement of Secreted Aβ levels and Lactase Dehydrogenase (LDH)

After reaching 80% confluence, a SH-SY5Y cells were 1:3 split onto two 12-well plates. After allowing the cells to settle for 24 hours, the medium was switched to a 1% FBS DMEM (Dulbecco's modified essential medium supplemented with 1% FBS and penicillin/streptomycin). Aβ Assays: Total Aβ amyloid levels were assessed as previously described (8) and AP-42 levels were measured by use of ELISA according to manufacturer's instructions (Covance Chemiluminescent BetaMark x-42 ELISA). LDH assay: The 1% FBS medium was recommended by the LDH Cytotoxicity Kit (Cayman Chemical, Ann Harbor, Mich.) to reduce interference as FBS also contains LDH. Cells were exposed to 10-fold increases in concentrations of JTR-009 reconstituted in IX PBS (0.1 nM-100 µM) compared to PBS as a control for 48 hours. Thus, eight wells on each 12-well were treated for 48-hour after which time 100 µL of supernatant was extracted from each of the treated wells and transferred to a 96-well plate. A LDH standard from the kit was also added to the plate. Using the reaction mixture in the kit, LDH absorbance values were obtained with a SpectraMax M5e plate reader and SoftMax Pro software ((Molecular Devices, Sunnyvale, Calif.)).

MTS Assay for Neuronal Viability

Cell viability was determined using MTT (thiazolyl blue tetrazolium) viability assays. Cells were grown in 96 well plates and treated as indicated above. After treatment, they were incubated with 20 µL of 5 mg MTT (Sigma)/1 mL PBS solution for 3.5 hours. The media was aspirated from the cells and 150 µL of solvent (0.1% Nondet P-40, 4 mM HCl in isopropanol) was added to each well and the plate shaken for 15 minutes. The absorbance was then read at 590 nm using a SpectraMax M5e plate reader and SoftMax Pro software (Molecular Devices, Sunnyvale, Calif.).

Results

Figure 1B:
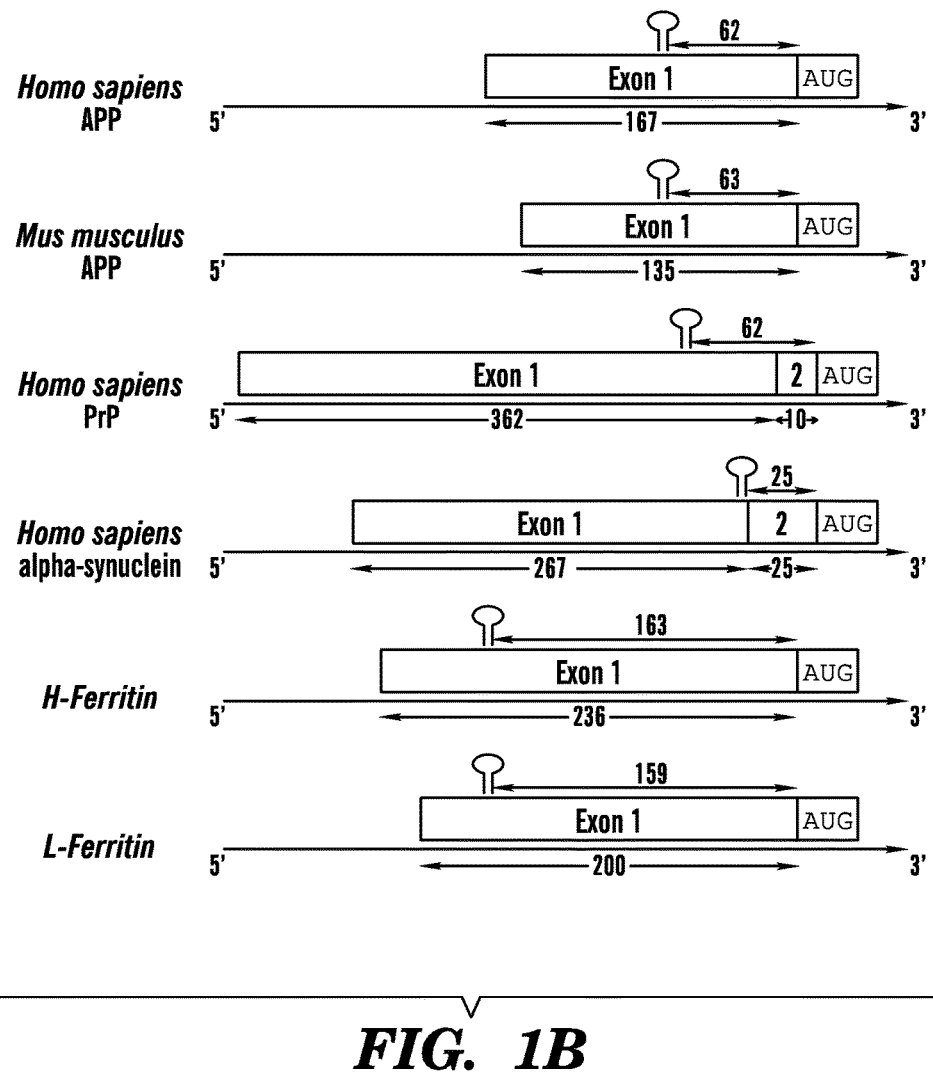
Figure 1D:
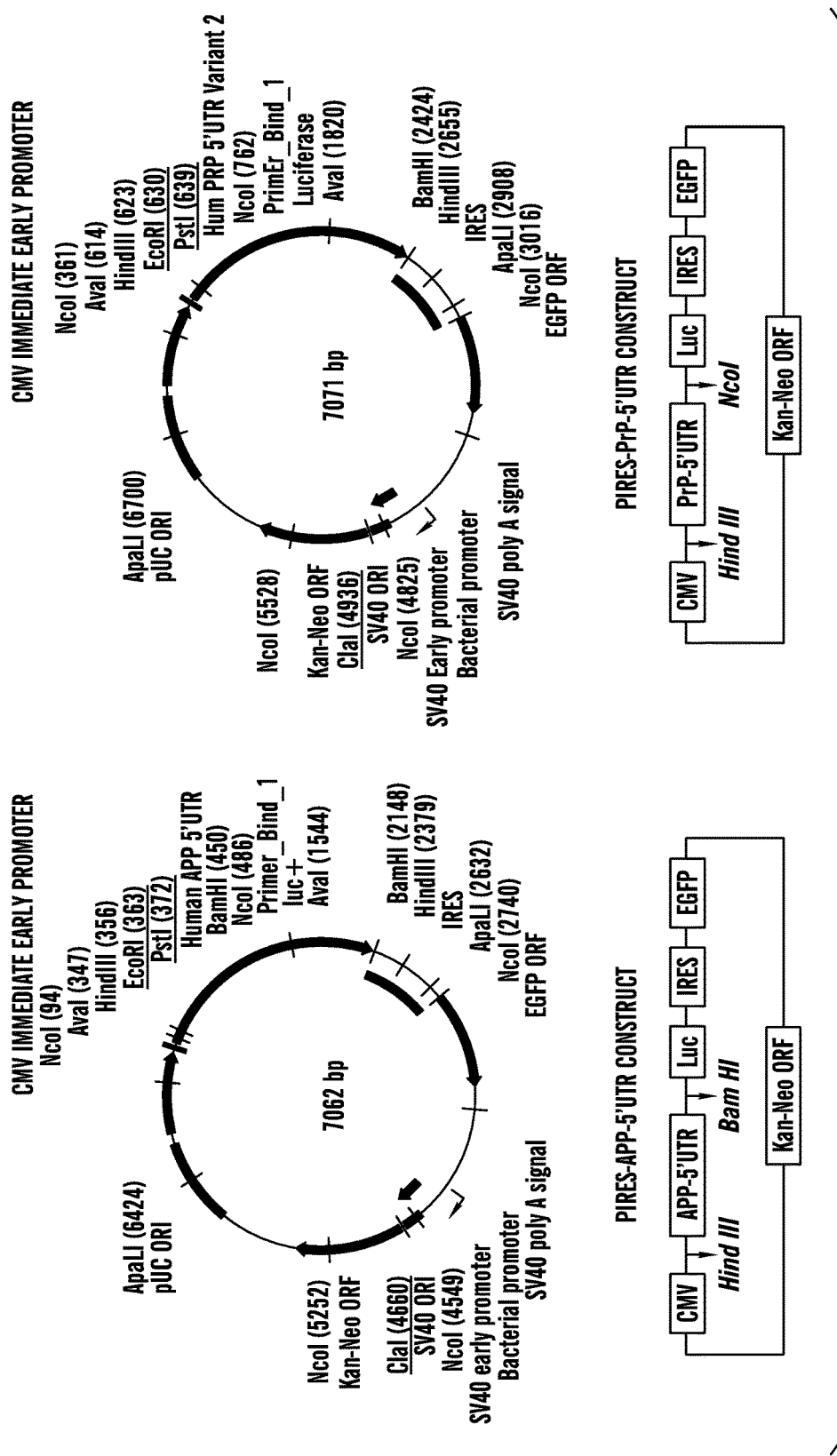

A: Selectivity of APP 5'UTR Translation Blockers from PrP 5'UTR-Based Counter-Screen FIG. 1A shows the specific RNA stem-loops encoded by the 5'UTRs of several neurodegenerative disease transcripts, specifically those for APP, PrP, and α-synuclein (SNCA). Each mRNA encodes uniquely configured variations of an IRE RNA stem loop that potentially bind to the IRP translational repressors in their 5'UTRs. The prion PrP 5'UTR was chosen as a stringent counter control for ensuring that APP 5'UTR directed compounds would be sufficiently specific not to inhibit luciferase reporter gene expression in matched PrP 5'UTR-driven transfectants. FIGS. 1B and 1C shows the maps and alignments of the 5'UTRs encoding IRE stem loops in the neurodegenerative transcripts for APP and αsyn relative to the canonical ferritin L- and H-chain IRE stem loops)[21]. FIG. 1C presents that this homology extends to that of the PrP 5'UTR, which encodes an IRE-like sequence, although diverged from the proven APP IRE (NCBI, Clustal software, [27]). Alignments elucidated a 56% similarity between this region of the 5'UTR of PrP mRNA (splice variant-2) and APP IRE sequences. This homology is centered around the CAGUGN loop domain of the canonical ferritin IRE and the projected IRP1 binding AGU/AGA tri-loops that were shown to be key for IRPI and IRP2 binding and translation repression [6,28]. The PrP (Vt2) 5'UTR was therefore deemed a stringent screening control to ensure specificity of the APP 5'UTR-directed translation blockers. FIG. 1D shows the complete coordinates of the screening constructs, pIRES-APP-5'UTR and pIRES-PrP-5'UTR, which were matched for insertion of equal length 5'UTRS for screen/counter-screen comparisons in transfection based assays (Bandyopadhyay et al., 2006).

The inventors conducted a screening campaign of library of 110,000 compounds with the stable transfected SH-SY5Y cells expressing the constructs shown in FIG. 1D. To identify APP 5'UTR-specific translation blockers from LDDN Harvard (see ref [21]) and from the Columbia University Genome center, the inventors then counter-screened against the PrP 5'UTR and shortlisted thirteen potent inhibitors to be further characterized. In FIG. 1D, the listed constructs were employed to conduct these transfection based assays to ensure that the 13 APP specific leads were not also PrP inhibitors. Table 1 lists the $IC_{50}$ of each of these inhibitors with respect to their dose-responsive capacity to reduce APP 5'UTR-driven luciferase expression relative to their $IC_{50}$ values against PrP 5'UTR expression. In Table 1, the calculations demonstrated a satisfactory >5-fold difference in $IC_{50}$ values for APP blockers JTR-004, JTR-009 and JTR-0013 and 3-fold difference for JTR-0010 and JTR-0011 (shown in bold lettering).

Several APP 5'UTR blockers exhibited closer-than-expected differences in $IC_{50}$ values when counter-assayed in dose response experiments against the PrP (vt-2) 5'UTR. To explain this finding, it is noted that these constructs and cell lines encoded 100 nucleotide RNA targets with unexpectedly closeness of 56% sequence identity by gap alignment between the 5'UTR of the APP and the PrP transcripts, as described previously [21]. This finding is consistent with recent reports that PrP is an iron exporter similar to APP (ferroxidase-II), underlying their newly found functional equivalence in addition to each being pathogenic proteins [5,29]. For this reason, of the thirteen confirmed leads (designated JTR-001 through JTR-0013), several may indeed provide a new class of agents that limit expression of both APP and PrP. All thirteen leads increased cell viability in SH-SYSY cells as measured by the MTT assay (see MTS assays for JTR-005 and JTR-009 in FIG. 3D).

Of the remaining leads that exhibited low toxicity and high selectivity towards APP 5'UTR sequences, three (JTR-002, JTR-007, JTR-009) harbored planar tricyclic benzimidazole backbones, and two (JTR-008, JTR-0013) were benzothiazoles. JTR-009 was selected for further studies as a result of two independent transfection-based determinations, which showed that this benzimidazole 10-fold more potently inhibited APP 5'UTR driven translation relative to the PrP 5'UTR (Table 1). The anti-stroke agent, pifithrin-alpha (PFTα), was a closely related benzothiazole to JTR-0013, and was previously found to be a selective APP translation inhibitor in assays. PFTα was already shown to be an in vivo acting inhibitor of tumor suppressor protein p53 [25] whereas other benzothiazole leads were similar to the Pittsburgh compound B (PiB) [30,31].

Figure 2:
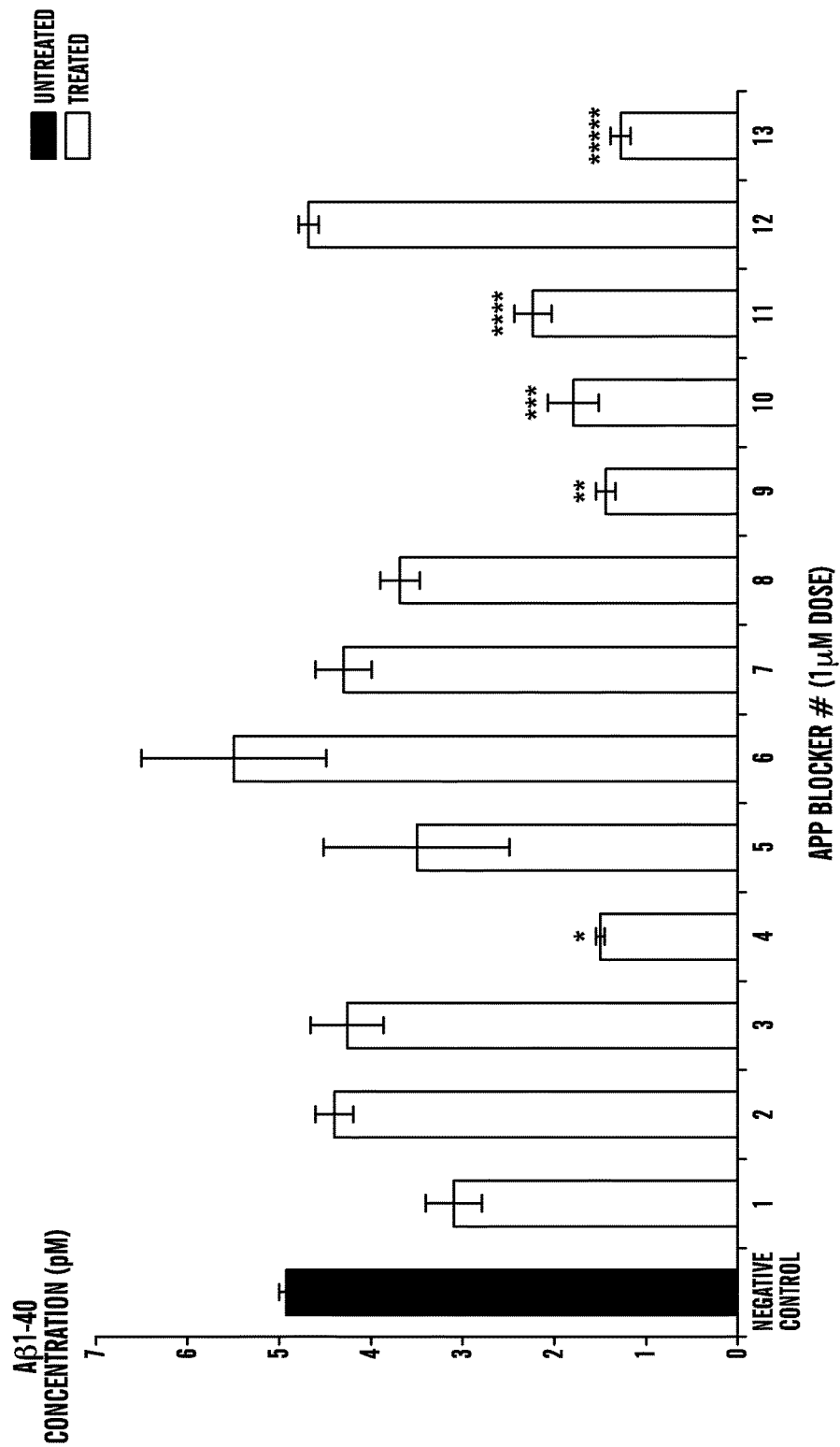
FIG. 2 shows the relative capacity of thirteen APP 5'UTR translation blockers to reduce Aβ levels in the conditioned medium of SH-SY5Y cells. Following 48-hour treatment (1 µM) for each inhibitor, the histogram shows reduction of total Aβ levels confirmed after averaging five independent samplings from the following:—JTR-009 treated<control, $p<0.01$. Total Aβ levels were also documented for the APP blockers JTR-004, JTR-10, JTR-0011, JTR-0013 (N=5). Data are means±SEM, N=5, *=$p<0.01$, =$p<0.01$, *=$p<0.0013$, **=$p<0.01$, ***=$p<0.011$, where each treatment was analyzed by ANOVA+Dunnett's post hoc test compared to untreated samples. JTR-009 was the ninth and JTR-005 was fifth in the series of 13 APP translation blockers.

The inventors next measured the relative extent to which the top thirteen APP 5'UTR blockers reduced Aβ secretion from SH-SY5Y cells after 48 hours of 1 μM treatment. Five drugs showed significant reductions in levels of total A13 peptide (JTR-004 (3-fold inhibition), JTR-009 (3-fold inhibition), JTR-0010 (2-fold inhibition), JTR-0011 (2-fold inhibition) and JTR-0013 (3-fold inhibition). With the exception of JTR-006 and -0012, each of the other APP 5'UTR directed inhibitors (1 μM dose) modestly reduced Aβ levels as measured by use of an ELISA (Biosource Int.) (See FIG. 2), a finding that confirmed which APP translation blockers reduced levels of cellular APP template sufficiently enough to reduce Aβ peptide output from SH-SY5Y cells.

Figure 3A:
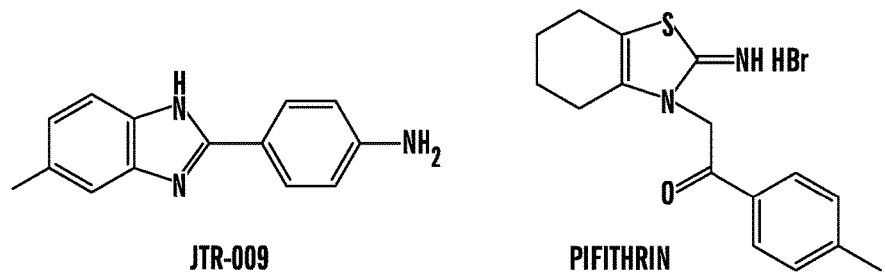
FIGS. 3A-3E show the effect of JTR-009 to reduce the steady state levels of APP in SH-SY5Y cells with a high degree of selectivity in the absence of changes to the levels of β-actin and α-synuclein (SNCA).
Figure 3B:
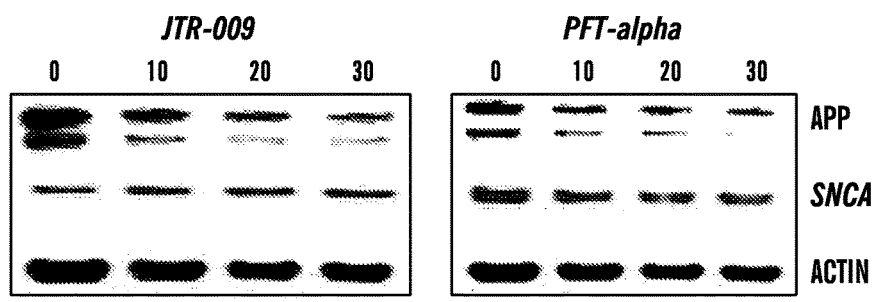
Figure 3C:
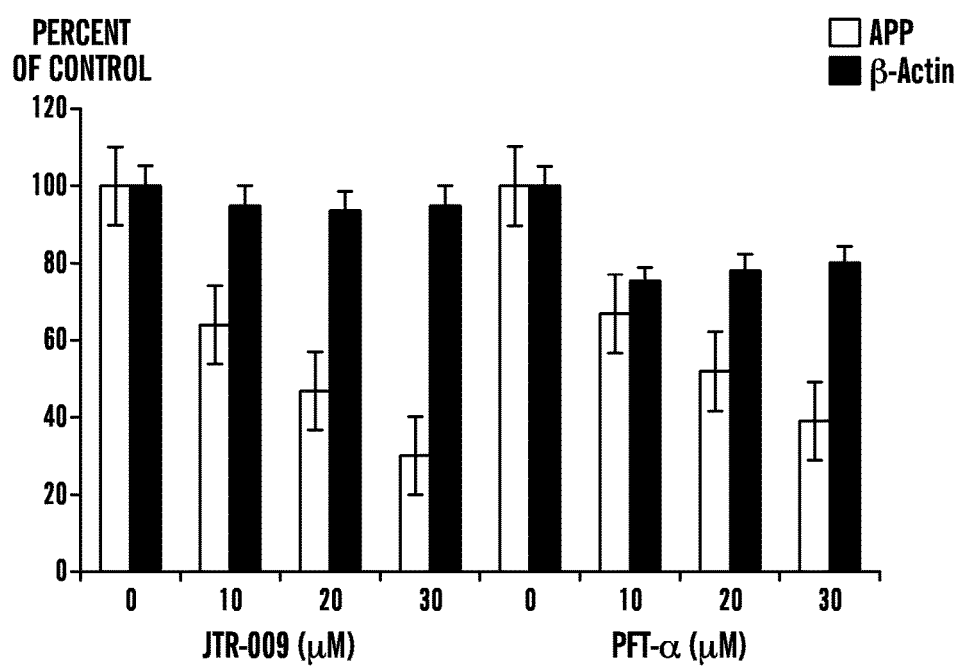
Figure 3D:
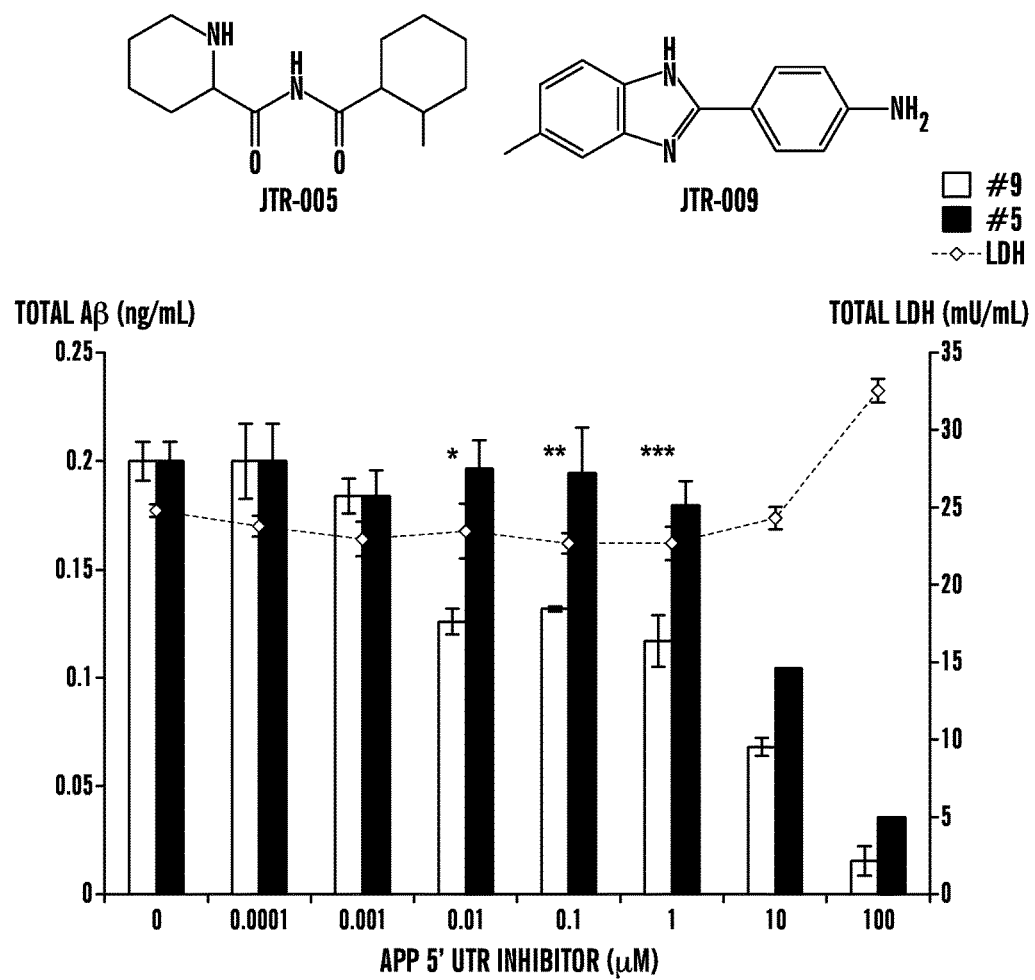
Figure 3E:
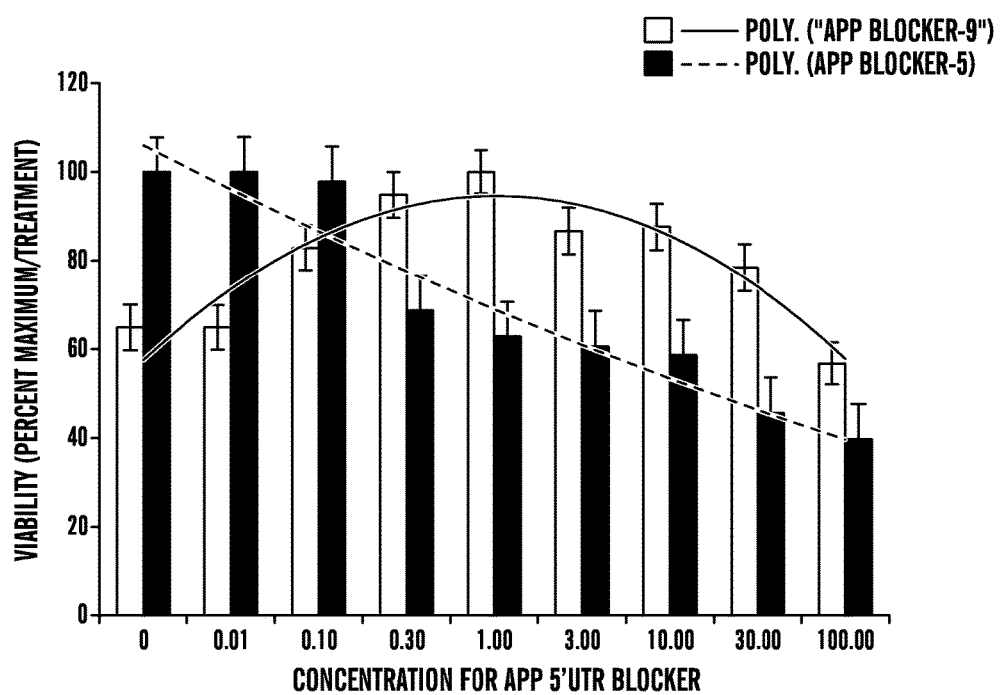

Of these, JTR-009 has consistently provided maximal cell viability (MTT assays see FIG. 3D). Thus JTR-009, as a translation blocker of APP mRNA, was sufficiently specific towards APP 5'UTR sequences and was considered to be a bona fide anti-amyloid agent (inhibition of Aβ by JTR-009 was 3-fold, ANOVA: $p=0.0046$, N=5 by pair-wise comparison of groups). JTR-009 was advanced for further analysis of the mechanism of the APP 5'UTR as a regulatory domain for APP gene expression at the level of message translation and as a candidate for future analog-based drug development as an anti-APP and anti-Aβ blocker for potential DS and AD therapy.

B: JTR-009: The Most Selective and Potent of the Thirteen Top APP 5'UTR-Directed Translation Blockers Consistently, JTR-009 was a highly specific APP 5'UTR translation blocker of luciferase reporter gene expression and also of steady state levels of APP (see Table 1 and FIG. 3). (Significantly, JTR-009 was an equally potent suppressor of Aβ peptide levels (FIGS. 2 and 3) [21]. Pifitluin (PFT-a), a well tolerated anti-apoptotic drug that has a benzothiazole structure similar to JTR-0013, was employed for the purpose of comparison with JTR-009. Therefore, as proven APP 5'UTR inhibitors, the benzimidazole JTR-009 and the benzothiazole pifithrin were compared for their relative capacities to limit APP expression in SH-SY5Y cells. In FIG. 3A, a representative Western blotting experiment demonstrated that both JTR-009 and PFTα dose dependently reduced APP translation. In FIG. 3B densitometry quantified from five separate experiments, including the one shown, demonstrated a 50% reduction of APP at 20 μM concentrations (48 hour treatment) after standardization for β-actin. JTR-009 reduced APP levels to 30% of control levels at 30 μM, while maintaining both (β-actin and α-synuclein (SNCA) levels (N=5, p=0.003). Several similar western blots experiments showed that JTR-009, but not PFTα, had sufficient specificity to limit APP while also maintaining β-actin and αsyn levels (48 hours). It's consistently found that PFTα, which has a benzothiazole backbone like JTR-0013, inhibited neural APP with the same potency as JTR-009 but was less specific since PFTα co-reduced αsyn levels (another IRE encoding mRNA [32]) as well as β-actin (FIGS. 3A and 3B).

Dose-responsive comparisons of JTR-009 with another APP 5'UTR-screened inhibitor, JTR005, were then assessed at equimolar concentrations to demonstrate the differential capacities of these two agents to limit Aβ secretion from SH-SY5Y cells (FIG. 3C). JTR-009 consistently inhibited secreted Aβ at concentrations as low as 10 nM (FIG. 3C). The fifth inhibitor in the series, JTR-005, was a typical comparative control compound since it is also a tricyclic planar compound but without a benzimidazole backbone. JTR-005 also targeted the APP 5'UTR (>PrP 5'UTR), although at 10-fold less potency than JTR-009. Consistent with this fact, JTR-009 reduced Aβ levels at lower concentrations than JTR-005 without causing any significant cell death as measured by an LDH cytotoxicity assay at concentrations up to 10 μM (FIG. 3C).

The relative cellular toxicity of the APP 5'UTR inhibitors JTR-005 and JTR-009 was determined by the MTT assay for cellular mitochondrial activity. FIG. 3D shows a representative experiment where the mean values for MTS absorbance was a reflection of viability after treatment of the cells with JTR-009 compared to JTR-005 at 0.01 μM (Percent of maximal viability for each treatment ±SEM (N=3)). These results consistently showed that mitochondrial staining was compromised by increased doses of JTR-005 whereas JTR-009 sustained cellular viability at 80% compared to controls, for concentrations of the drug as high as 100 μM. In sum, JTR-009 increased the relative viability of SH-SY5Y from escalating doses from 1 nM to 1 μM and sustained high viability to 30 μM concentrations. JTR-009 is thus ranked as the most potent and least toxic APP 5'UTR inhibitor (FIG. 3).

Figures 4A, 4B:
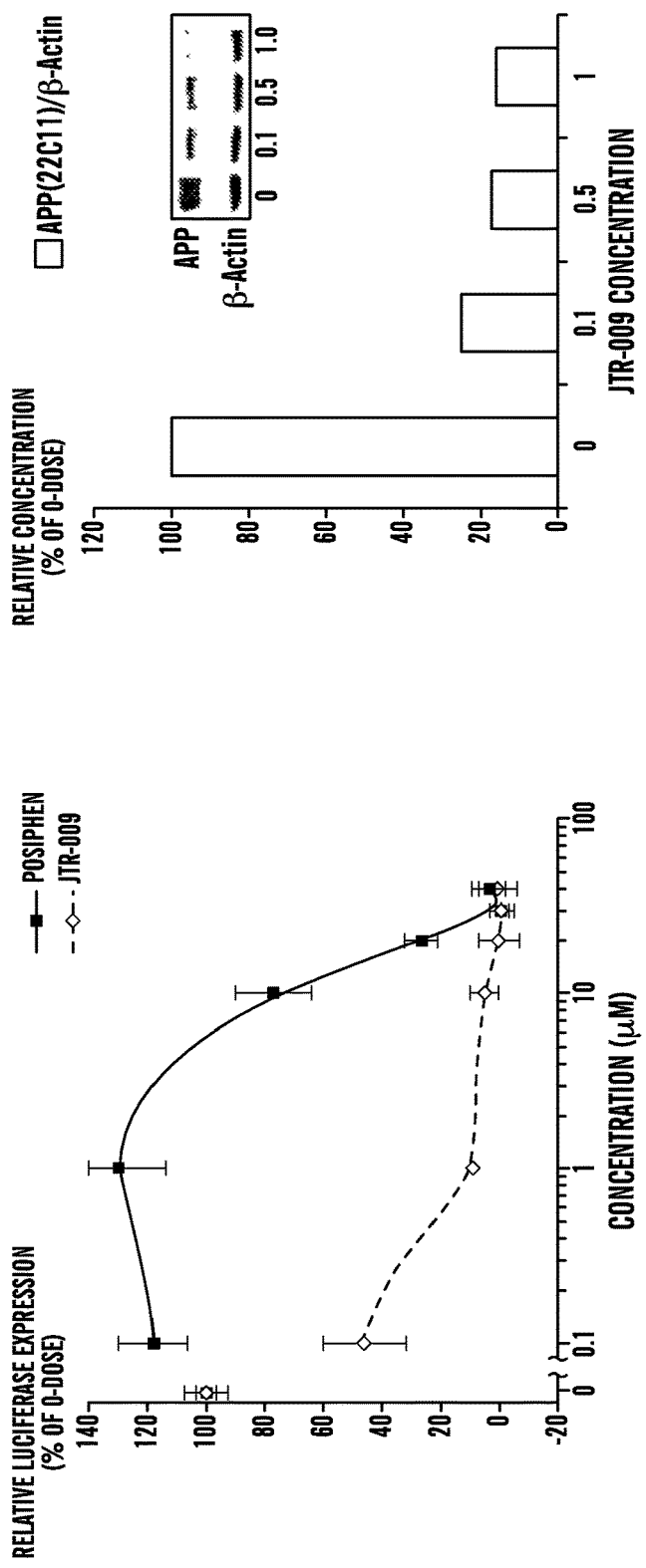
FIGS. 4A-4F show evaluation of the potency and selectivity of APP blocker-9.

C. JTR-009 as a Low-Dose Acting Compound in Both SH-SYSY Cells and Primary Cortical Neurons Relative to Posiphen as a Well-Tolerated APP 5'UTR Acting Agent The anticholinesterase, phenserine (PS), and its (+)-enantiomer, posiphen were previously characterized as APP 5'UTR-directed drugs. Indeed, posiphen passed Phase 1 clinical trials for AD, exhibiting anti-amyloid efficacy [31, 32, 33, 34]. A direct comparison of the inhibitory potency of JTR-009 and posiphen is shown in FIG. 4A). Here, the comparative IC50 of posiphen to reduce APP 5'UTR-luciferase expression was 5 μM whereas JTR-009 was maximally 50-fold more potent (see also Table 2). At 0.1 μM drug concentrations, JTR-009 treatment reduced APP 5'UTR activity two-fold (N=4, p<00015) whereas posiphen increased APP 5'UTR activity by 15% (p<0.0299 under matched conditions). These experiments were highly reproducible and confirmed the potency of the action of JTR-009 compared to posiphen as a well-tolerated APP 5'UTR-directed translation blacker that had previously been reported to display anti-amyloid efficacy in viva [33][34].

TABLE 2

Comparative $IC_{50}$ of JTR-009 relative to posiphen to inhibit APP 5'UTR driven luciferase expression relative to suppression of APP and Aβ levels in SH-SY5Y cells and primary neurons

| Drug | APP 5'UTR Inhibition ($IC_{50}$) | APP and amyloid-beta Inhibition ($IC_{50}$) | Specificity (×10 of $IC_{50}$) | Toxicity (MTT) |
|---|---|---|---|---|
| JTR-009 | 100 nM | 100 nM (max 10 nM) | β-actin (×20), αsyn (×20) | 100 μM |

TABLE 2-continued

Comparative IC$_{50}$ of JTR-009 relative to posiphen to inhibit
APP 5'UTR driven luciferase expression relative to suppression
of APP and Aβ levels in SH-SY5Y cells and primary neurons

| Drug | APP 5'UTR Inhibition (IC$_{50}$) | APP and amyloid-beta Inhibition (IC$_{50}$) | Specificity (×10 of IC$_{50}$) | Toxicity (MTT) |
|---|---|---|---|---|
| Posiphen | 5 μM | 1 μM (Refs 27, 33) | β-actin (×20), αsyn (×1) | 100 μM |

Figures 4C, 4D:
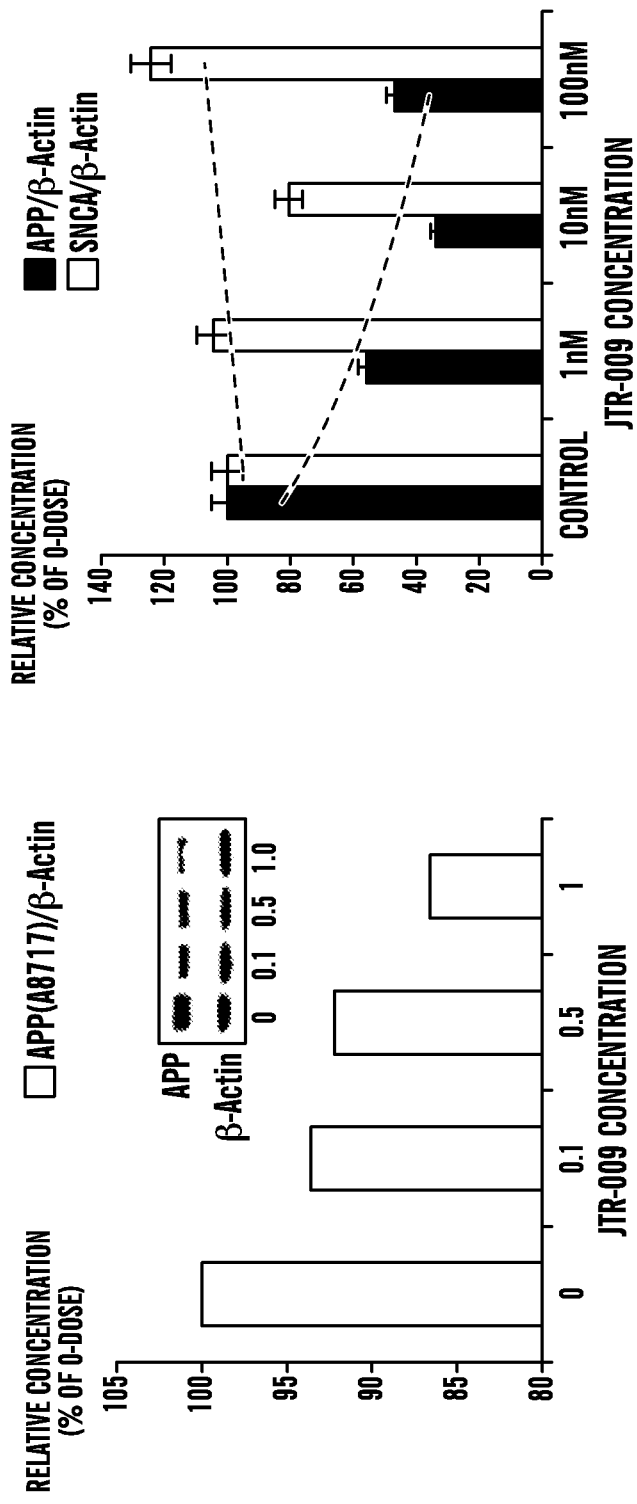

In the experiments represented by FIGS. 4B-4C, at 80% confluence, SH-SY5Y cells were tested with JTR-009 at the 0.1 μM, 0.5 μM and 1 μM concentrations indicated. After 48 hours of treatment, the cells were collected in lysis buffer and analyzed by multiple western blots. The inventors consistently observed a low dose efficacy of JTR-009 to limit APP expression in SH-SY5Y cells whereas, even at higher doses, the compound maintained cell viability (N=7). These western blot data demonstrated that JTR-009 consistently reduced APP levels ((β-actin standardized in SH-SY5Y neural cells) (FIGS. 4B and 4C) at equivalent concentrations. Here, both A8717 (APP C-terminal specific in FIG. 4C) and 22C11 (APP N-terminal specific in FIG. 4B) antibodies were used to detect APP whereas β-actin was used as a loading standard in two separate experiments. In sum, JTR-009 effectively limited APP production on SH-SY5Y cells at doses as low as 100 nM.

Shown in FIG. 4D, JTR-009 reduced APP levels by 60% at concentrations as low as 10 nM in primary mouse cortical neurons while α-synuclein (SNCA) levels were unchanged and cell viability was maintained. The histogram shows the measured levels of APP as assessed with the 22C11 APP specific N-terminal antibody for western blots after standardization with (β-actin. The average pair-wise reduction of SNCA levels after control/JTR-009-treatment was at a 50% threshold for 0.001 μM drug exposure to cells for 48 hours. These same treatment conditions left α-synuclein expression unchanged (p<0.01, analyzed by ANOVA).

Figure 4E:
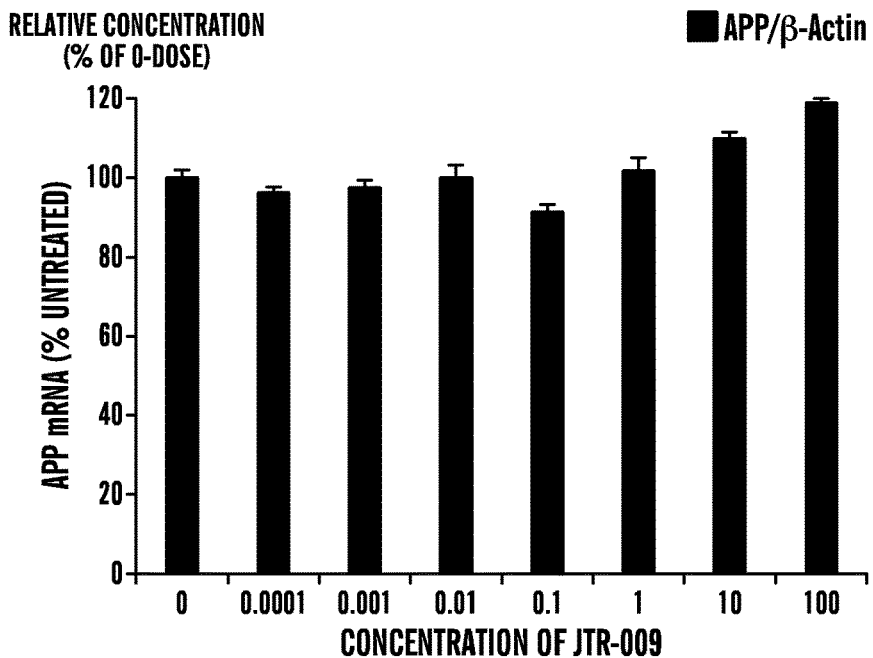

Of significance, APP Blocker-9 did not reduce APP mRNA levels to account for the reduction of precursor protein as judged by qRT-PCR analysis (N=4). In fact, APP mRNA levels were unchanged at increasing doses from 0.1 nM to 10 μM drug (FIG. 4E). Thus, at concentrations that ablated APP protein expression by >75%, APP mRNA levels were unchanged. Indeed the steady state levels of APP mRNA were found increased at concentrations of JTR-009 that were greater than 10 μM. Specifically, exposure of SH-SY5Y cells to 100 μM JTR-009 increased APP mRNA levels by ~10% whereas APP protein expression was nearly completely blocked (FIGS. 4A-4D compared to FIG. 4E). These data underscore that JTR-009 blocks APP expression at the level of APP mRNA translation and not at the level of APP transcription.

Figure 4F:
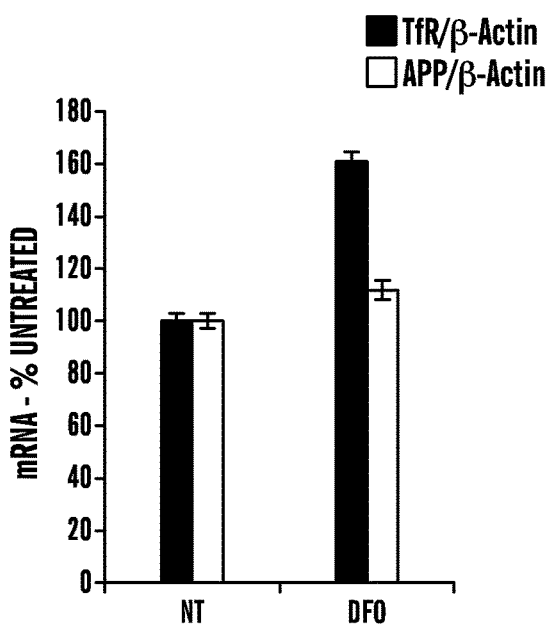

As a positive control, transferrin receptor mRNA levels were 2-fold increased in the presence of iron chelation with desferrioxamine (FIG. 4F). By contrast, APP mRNA was unchanged by iron chelation with desferrioxamine, as previously reported [6].

Figure 5B:
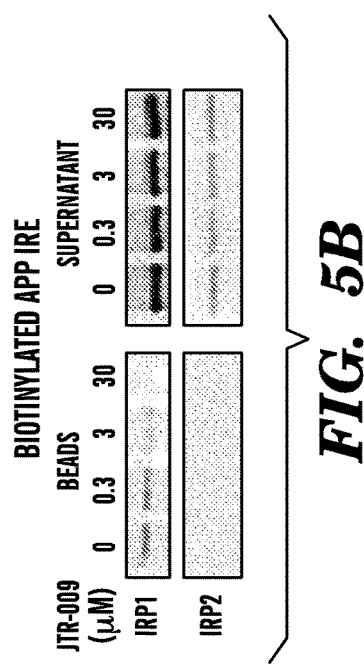
Figure 5C:
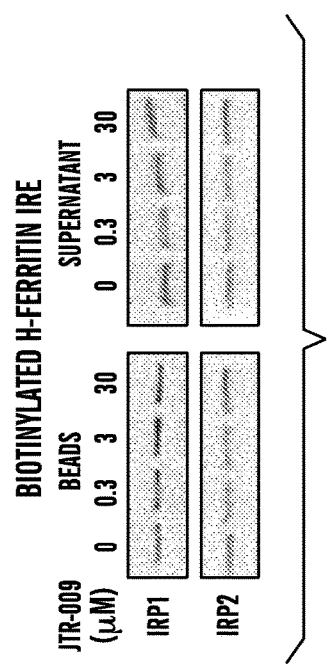
Figure 5A:
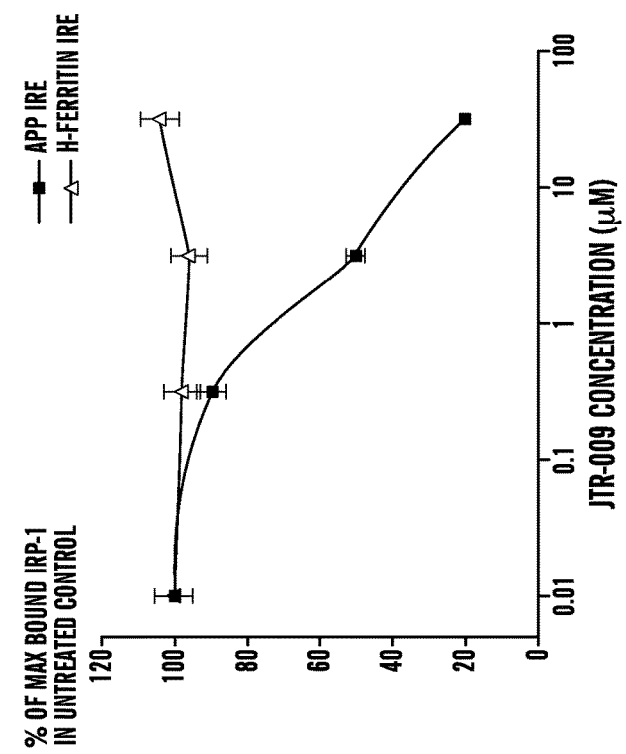

D. Mechanism of Action: JTR-009 is a Benzimidazole and Irreversibly Replaces IRP1 from Binding to the APP 5Utranslated Region When evaluating the mechanism of JTR-009, it was noted that a low molecular weight RNA intercalator had been previously reported from the same molecular library source as JTR-009 [35], and this agent had been shown to prevent a tau-mRNA splicing event that can cause frontotemporal dementia [35]. Therefore, using SH-SY5Y cells, biotinylated RNA pulldown assays (FIG. 6A) were employed to measure the effect of JTR-009 on the binding of IRP1 to the APP 5UTR (FIG. 5). Multiple biotinylated RNA pulldown assays provided data to confirm that this benzimidazole-based molecule acted "on-target" to substitute for IRP1 interaction as a repressor of APP translation at the site of the APP iron-responsive element RNA stem loop. FIG. 5B showed that administration of JTR-009 to SH-SY5Y cells dose dependently diminished the percent of IRP1 bound to biotinylated APP IRE RNA probes. Densitometry, as shown in FIG. 5B, quantitated that IRP1 binding was reduced by 20% (±2%) at 0.3 μM, by 50% (±5%) at 3 μM, and was completely inhibited at 30 μM (±1%) JTR-009 (N=7, p=0.003). Confirming specificity, full interaction between IRP1 and IRP2 and the H-ferritin for IRE probes were always maintained during conditions of induction with JTR-009 (Densitometry in FIG. 5A is shown to reflect a representative Western blot in FIG. 5C)).

Figure 6A:
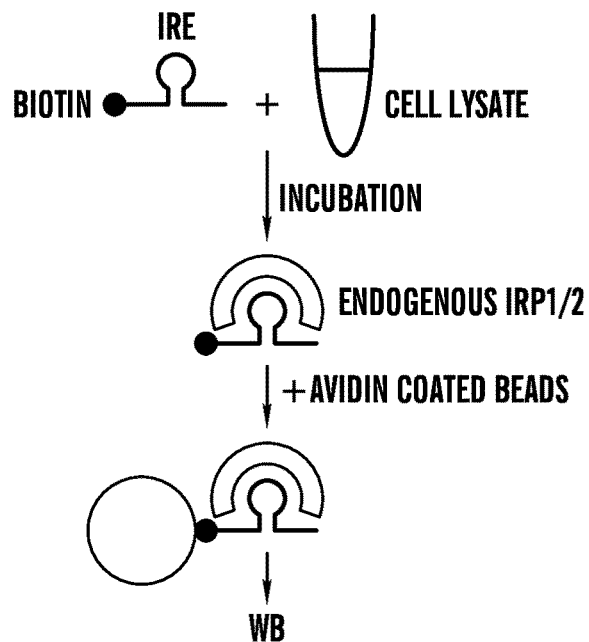
FIGS. 6A-6C show RNA binding assay to measure the capacity of JTR-009 to replace IRP1 binding to biotinylated probes encoding core APP IRE sequences compared to IRP1 binding to the H-ferritin IRE sequences (N=4).
Figure 6A:
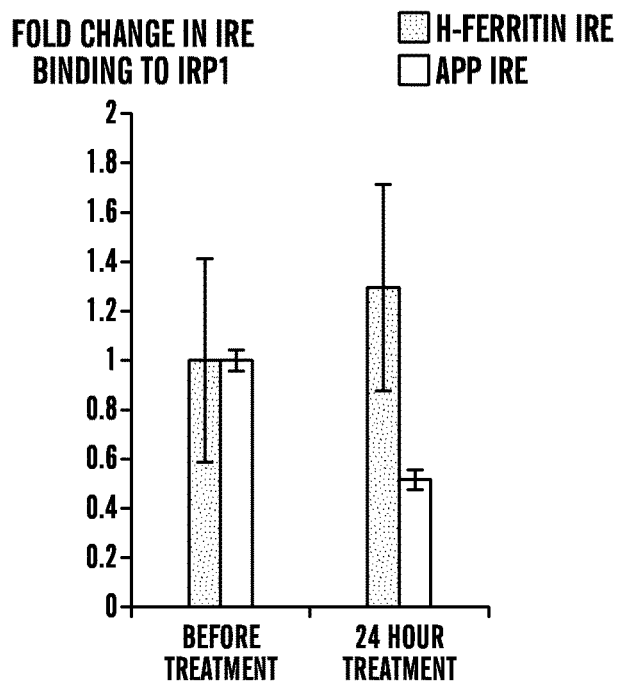

The data in FIG. 5E provides a representative Western blot experiment from 7 independent experiments when using JTR-009 at 0.3 μM, 3 μM and 30 μM concentrations to inhibit APP expression in the lysate/supernatant fractions of SH-SY5Y cells subjected to RNA pulldown analysis (FIG. 6A). Consistently, it was observed that JTR-009 blocked APP expression as shown by the decreased levels of the precursor when detected with both C- and N-terminal specific antibodies. This reduction of APP levels directly correlated to the elimination of IRP1 binding to APP 5'UTR sequences. FIG. 5D shows densitometry to obtain the average reductions of APP levels from multiple Western blots as represented by FIG. 5E (N=6 for each set). A 70%±5% reduction of APP was observed at 30 μM (N=4, p=0.02) and 35% at 3 μM JTR-009 (p=0.01, Dunnetts post-hoc test).

E. JTR-009 Reduced APP Expression Via its IRE in an Iron Independent Manner

Figure 7:
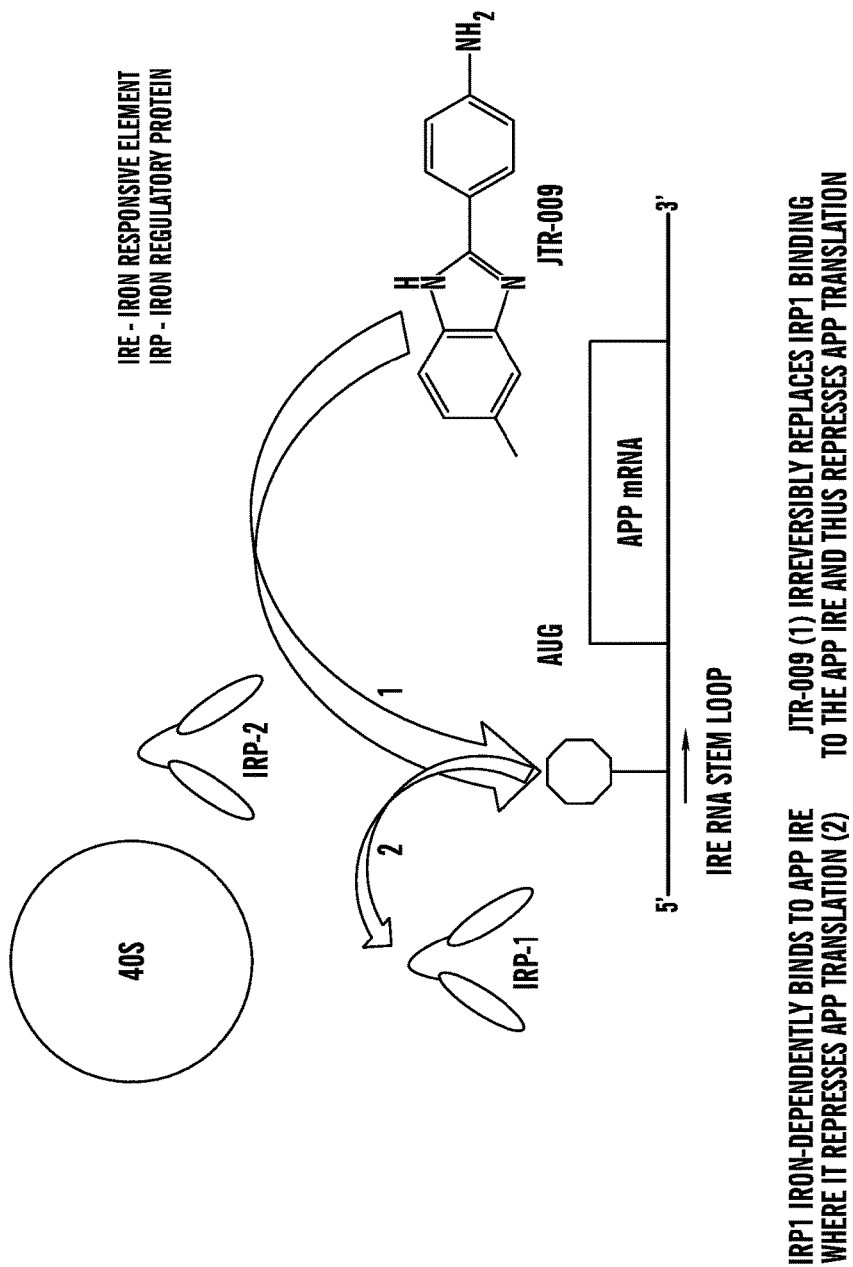
FIG. 7 is a model for the action of the benzimidazole JTR-009 to act as an inhibitor of APP translation by irreversibly replacing the iron dependent translation repressor IRP1 from interacting with APP 5'UTR sequences. Binding of JTR-009 selectively targeted APP 5'UTR sequences and then was found to repress APP levels leading to reduced amyloid levels without perturbing cellular iron uptake.

To confirm an "on-target" mechanism for JTR-009 and its relative iron-independence when acting via APP 5'UTR, the inventors had previously performed a molecular determination of the iron-dependent, reversible binding of IRP1 to the APP IRE stem loop (Kd=30 pM) [6]. The data shown in FIG. 5 is consistent with the model that JTR-009 substituted for IRP1 binding to APP 5'UTR sequences. In FIG. 6A, the inventors compared the extent to which JTR-009 decreased IRP1 binding of APP-IRE in SH-SY5Y cells compared to H-Ferritin-IRE RNA probes. Here, the results consistently showed that 3 μM JTR-009 (48 hour exposure) reduced IRP I binding to the APP IRE by 2-fold whereas under the same conditions this benzimidazole displayed no inhibitory change in binding to H-ferritin IRE probes. These data were consistent with the conclusion that JTR-009 bound selectively to the APP IRE sequences and not to related RNA probes encoding the ferritin-H IRE, an observation consistent with the proposed mechanism of action of JTR-009 as shown in FIG. 7.

Figure 6B:
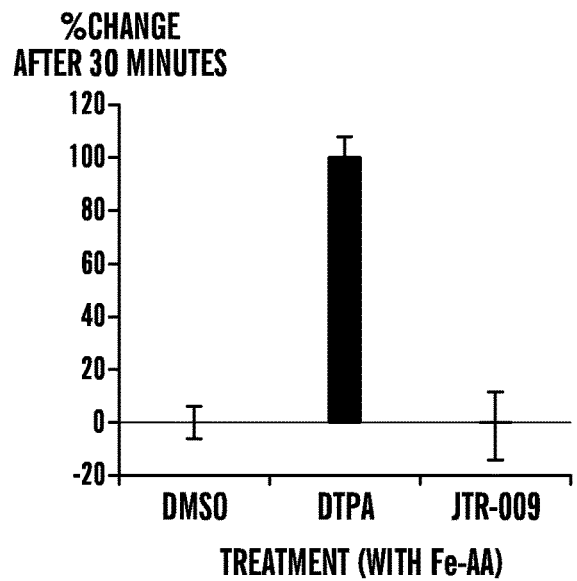
Figure 6C:
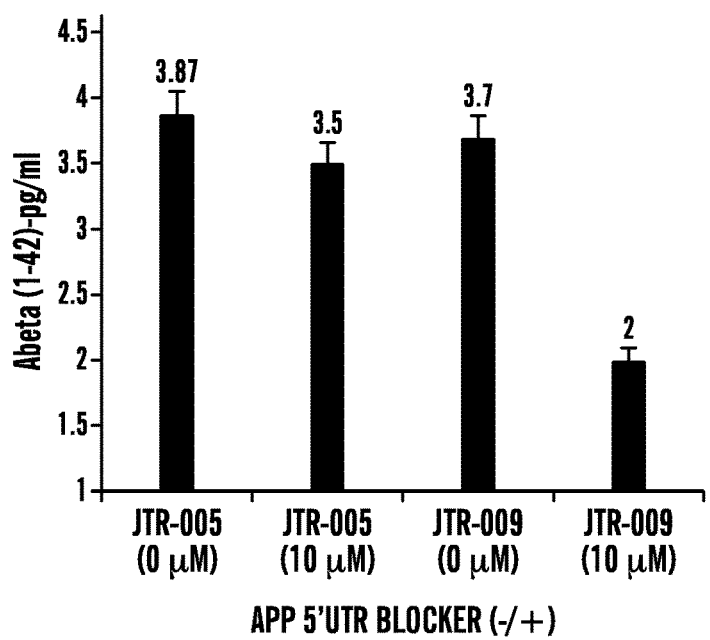

The effect of JTR-009 on iron homeostasis was directly measured in a calcein uptake assay in SH-SY5Y cells (FIG. 6B). The drug (DTPA) was the positive control as an extracellular chelator that completely blocks iron uptake. Normalized results were graphed and these data showed that DMSO caused 0±6% inhibition of the amount of calcein stain (proportional to iron levels) and DTPA caused 100±8% inhibition. Of note, JTR-009 induced a −1±13% inhibition of calcein staining. Thus under these conditions, the inventors systematically observed that JTR-009 had little or no effect on iron uptake (TfR dependent and independent uptake pathways).

Aβ-42 peptide is the critical APP derived peptide to trigger the aggregation of amyloid in both AD and DS and is critically linked to tau induced neurotoxicity [36]. Thus, the inventors tested and reproducibly demonstrated that JTR-009 limited Aβ-42 secretion from SH-SY5Y cells by more than two fold. In this representative experiment, a chemiluminescent BetaMark x-42 ELISA assay for Aβ-42 measurement was employed (Covance, inc). The assays were carried out according to the manufacture's conditions such that the standard curve was linear and the measured points were within the 'standards' range. JTR-005 exhibited only a 20% reduction of Aβ-42 output after the same 3-day treatment as that of JTR-009 (72 hour treatment).

In sum, these experiments demonstrated that JTR-009 operated by direct pathways to reduce APP translation an Aβ-42 output and the compound did not act via indirect pathways as a secondary iron chelator in which case the drug would be expected to activate binding of IRP1 as a translational repressor. The working model shown in FIG. 7 evidenced that JTR-009 interacts directly with the APP IRE RNA stem loop.

DISCUSSION

RNA-directed drugs have long been used to treat infectious diseases, e.g. antibiotic aminoglycosides, and small RNA-directed molecules have been used to control gene expression in cell culture models [37] (e.g. therapeutic control of viral Hepatitis C/HIV gene expression [38]). In mammals, endogenous up-regulation of the translation of the iron storage protein ferritin by 'yohimbine', as a ligand of its native RNA, was shown to enhance protection of cells from Fe-catalyzed oxidative stress [39].

It was previously demonstrated that it is feasible to generate pharmacological anti-amyloid efficacy by targeting the 5'UTR sequences in the amyloid precursor protein (APP) transcript [40]. Certainly, iron chelation with desferioxamine increased RNA protein interactions between Iron-regulatory Protein-1 and the transcript that translates APP, a pharmacological treatment predicted to reduce levels of Aβ peptide both in vitro and in vivo [6,8]. It was also reported on the use of FDA pre-approved drugs as inhibitors directed against the 5'UTR of the APP transcript. For example, the tricyclic benzoxazole paroxetine (serotonin-specific reuptake inhibitor) and the antioxidant N-acetyl cysteine (NAC) suppressed APP 5'UTR driven translation of a luciferase reporter gene and actively limited APP mRNA translation and Aβ production in neural cells lines without altering amyloid precursor-like protein-1 (APLP1) levels [41]. Both paroxetine and NAC subsequently displayed in vivo anti-amyloid efficacy in APP transgenic mice [8], an approach extended to the use of agents of potential benefit to Parkinson's disease patients for whom proven FDA drugs limited the translation of SNCA mRNA by targeting SNCA 5'UTR sequences [32].

As a second example of the use of APP 5'UTR-directed inhibitors, the well-characterized drug posiphen was found to block translation of APP and limit amyloid levels, both in neural cells lines [42,43] and in mice in vivo [33]. Posiphen operated in the micromolar range and, like the other well-characterized APP 5'UTR-directed inhibitor pifithrin, limited expression of APP but also that of (β-actin and α-synuclein (FIG. 3)).

Here, the inventors introduced the mechanism-of-action of a new class of APP translation inhibitors with improved potency and selectivity to the uniquely folded APP 5'UTR target. The in vitro and ex vivo action of APP blocker-9 (JTR-009) was characterized, a significantly more potent and more selective translation blocker than posiphen. The data in Table 2 summarizes the repress APP expression in SH-SY5Y cells and in primary neurons.

The stringent counter-screens identified that the ninth of the series of the thirteen APP translation blockers displayed a 2-fold higher capacity to inhibit APP 5'UTR-conferred luciferase expression in pIRES-APP-5'UTR transfectants relative to PrP 5'UTR repression of luciferase expression in the pIRES-PrP-5UTR cells. Other APP 5'UTR inhibitors such as JTR-008 (a benzothiazole) did not exhibit selectivity in this counter-screen (Table 1). In sum, APP 5'UTR directed translation blockers, such as JTR-009, offer an improvement on the use of both phenserine and its stereoisomer posiphen, both of which were shown to block APP translation and limit Aβ expression upon administration to human clinical trial volunteers [34].

Contrary to the action of iron specific chelators that promote repression of APP translation by IRP1, the mechanism-of-action of JTR-009 in SH-SY5Y cells was consistent with this small molecule acting "on-target" to directly intercalate into the RNA stem loop that encodes the iron-responsive element RNA stem-loop in APP mRNA. The data in FIG. 5 was representative of multiple tests (N=8), showing that JTR-009 reduced APP mRNA translation in SH-SY5Y cells correlated with its substitution for IRP1 binding to APP 5'UTR sequences. Consistent with this, several of the chemical features of the hits from the second HTS undertaken at Columbia University screen were common to the first screen, including a potential structure-activity relationship (SAR), since five of the thirteen leads fell into two related classes of compounds: compounds with benzimidazole backbones and compounds with benothiazole backbones. These compounds may also intercalate into the APP 5'UTR RNA secondary structure as aromatic planar molecules, each capable of forming hydrogen bonds with the phosphate backbone of RNA helix (26).

Two models can be tested to explain how JTR-009 acts to inhibit APP translation with such high selectivity. JTR-009 is a benzimidazole that may alter intracellular kinase signaling so as to replace IRP1 for another, as yet unidentified, translation repressor of APP via its 5'UTR. However, a more likely mode is that JTR-009 operates by a mechanism of drug action similar to that observed for other benzimidazoles [26,44] and that is, by selectively intercalating between the bases stacked in the unique RNA stem loop folded by APP IRE sequences (see FIG. 1A and FIG. 7). This model is further backed by examples of other RNA-targeting drugs that intercalate with the tau mRNA stem loop that can modulate splicing events relevant to the onset of frontotemporal dementia [45]. By irreversibly replacing IRP1 as the binding partner of the APP IRE stem loop, JTR-009 could directly interfere with ribosome scanning of the APP 5'UTR by the 40S ribosome prior to translation of the precursor (see model in FIG. 7). This tricyclic benzimidazole compound did not change the binding pattern between IRP1 and the classic H-ferritin IRE (FIG. 6), confirming its selectivity [6]. The $IC_{50}$ for its translational inhibition of APP was <1 μM, as established from dose-responsive assays [46].

Calcein assays were used to determine that pharmacological reduction of APP was not mediated by indirect changes to iron levels to change APP expression and Aβ production (FIG. 6B). Therefore, JTR-009 was sufficiently selective to the APP IRE stem loop to reduce APP, while not changing several biomarkers of intracellular iron status of cells. Since APP translation was previously shown to be closely controlled in response to intracellular iron levels, this scenario was originally thought to be a possible mechanism [6]. Instead, the binding of IRP1 and IRP2 to the ferritin IRE was unaffected by exposure of neural cells lines to JTR-009 (FIGS. 5 and 6). Together with the lack of changes of cellular calcein stains, these data evidenced that JTR-009 exerted a direct action on APP and blocked amyloid without gross perturbations to iron homeostasis (See FIG. 7).

The prolonged use of JTR-009 would be predicted to limit APP mRNA translation to thus reduce intracellular APP levels, a situation that causes greater iron retention within cells with the loss of APP facilitated iron export by ferroportin [5]. However, the results disclosed herein showed little or no change in intracellular iron content after treatment of SH-SY5Y (or primary neurons) with JTR-009. Thus, the reduced amount of iron to be exported predicted from loss of APP could have been compensated by less iron uptake by transferrin bound or unbound pathways [5]. Another attractive model is that JTR-009 increased translation of ferroportin at the same time as it inhibited APP production, which explains the reason that intracellular iron levels were unchanged in response to JTR-009. For example, JTR-009 could have altered IRP1 binding to the IRE in DMTI mRNA and/or ferroportin mRNA to account for the predicted compensatory increase in cellular iron expected by loss of APP expression since APP is an iron export fetToxidase [5].

Consistent with the capacity of JTR-009 to maintain correct iron balance and to operate as a potent anti-amyloid agent, this benzimidazole-enhanced cell viability was observed by use of MTS and LDH assays. In fact, JTR-009 was pharmacologically non-toxic in SH-SY5Y cells as measured by MTS assay (FIG. 3D). Dose-responsive measurements confirmed the IC50 against the APP 5'UTR to be in the 1 nM to 100 nM range while the APP 5'UTR-directed JTR-009, only displayed cell toxicity at concentrations >30 μM in SH-SY5Y cells and in primary neurons. Significantly, JTR-009 exhibited a similar toxicity at 100 μM in SH-SY5Y cells as was previously demonstrated for posiphen (+ve control) [21].

Certainly JTR-009 was a highly selective APP inhibitor that operated at very low concentrations in the nanomolar range, as has been evident in other kinase inhibitors. The series of experiments shown in FIG. 4 revealed that low doses of JTR-009 typically reduced APP expression. Intracellular APP inhibition was quantified by densitometry such that both the N-terminus 22C11 antibody and the C-terminus A8717 antibody of APP were cross-referenced. It was found that each of the APP 5'UTR inhibitors lowered Aβ secretion from SH-SY5Y neuroblastoma cells (FIG. 2), albeit at levels near the limits of detection for Aβ (pg/mL range).

Of note, the potency of JTR-009 to inhibit APP 5'UTR conferred translation was greater than posiphen (FIG. 4A). In primary mouse E-18 neurons, JTR-009 inhibited APP levels with no reduction of β-actin at doses as low as 1 nM and, dose-responsively, as high as 100 nM (FIG. 4D). The same concentrations of JTR-009 demonstrated no significant changes to α-synuclein levels (the western blots were standardized to 0-actin) (FIG. 4D).

The inventors sought to more stringently identify novel agents as translation blockers specifically of APP 5'UTR sequences by counter-screening APP inhibitor leads against the PrP (Vt-2) 5'UTR. To this purpose, the inventors employed SH-SH5Y cells stably transfected with the pIRES-APP-5'UTR and pIRES-PrP-5'UTR constructs, which expressed a lucifcrase reporter driven respectively by the APP and PrP (V2) 5'UTRs (FIG. 1D). While undertaking the counter-screens, the inventors identified an unexpectedly close 56% identity between PrP and APP mRNAs as well as a putative IRP1 binding site in the 5'untranslated regions in both mRNAs. These similarities provided an explanation as to why the dose-responsive counter-screen identified similar $IC_{50}$ values for both APP and PrP 5'UTR dependent inhibition of luciferase reporter expression (Table 1).

Consistent with these observations, recent reports linked the function of both APP [5,6] and PrP to a common role in iron transport where both these neurodegenerative gene products are differentially increased by iron [29,47]. APP mRNA encodes a fully functional IRE [6] and the inventors' bioinformatic alignments showed that secondary structures of the 5'UTRs of several neurodegenerative transcripts also appear to encode IRE RNA stern loops, for instance in the related 5'UTR of PrP mRNAs (FIG. 1). This unexpected close sequence similarity between the PrP 5'UTR to that of the APP 5'UTR may explain why many of the top APP specific inhibitors were found to also repressed prion (PrP) expression. Certainly these two neurodegenerative proteins are linked with a common role in iron transport and metabolism [29] where recent discoveries also show an in vivo interaction of the Aβ amyloid protein and the PrP prion during the progression of neurodegenerative disease [48]. However, these findings also underscored the specificity of JTR-009, which inhibited APP expression 10-fold more actively than that of the prion PrP protein.

The single major conclusion from this work is that APP 5'UTR sequences indeed are a significant regulator of Aβ precursor expression in neural cells. In this report, it was via APP 5'UTR-dependent pathways that the inventors pharmacologically limited the steady state levels of APP not only in SH-SY5Y cells but also in primary cortical neurons. These APP 5'UTRs-directed inhibitors are currently being tested as representatives of a class of intercalators that exhibit high selectivity in reducing APP production in SH-SY5Y neuroblastoma cells. They also limited Aβ production with little or no perturbation of cellular iron homeostasis while maintaining neuronal viability. Such capabilities are the requirements for future drugs with therapeutic potential for AD and Down syndrome. On a technical level, the optimal compound was shown to be a benzimidazole, JTR-009, that limits APP translation at less than one nanomolar concentrations with little evidence of neurotoxicity. This tricyclic compound inhibits APP translation by directly interacting with the IRE in the 5'UTR of APP mRNA, irreversibly replacing IRP1 as a repressor of translation. JTR-009 was 10-fold more effective to limit APP translation than posiphen, a well-tolerated APP 5'UTR-directed translation blocker [33].

REFERENCES FOR EXAMPLE 1

1. Mackenzie I R, Rademakers R, Neumann M (2010) TDP-43 and FUS in amyotrophic lateral sclerosis and frontotemporal dementia. Lancet Neurol 9: 995-1007.
2. Darnell J C, Van Driesche S J, Zhang C, Hung K Y, Mele A, et al. (2011) FMRP stalls ribosomal translocation on mRNAs linked to synaptic function and autism. Cell 146: 247-261.
3. Lovell M A, Robertson J D, Teesdale W J, Campbell J L, Markesbery W R (1998) Copper, iron and zinc in Alzheimer's disease senile plaques. J Neurol Sci 158: 47-52.

4. Bandyopadhyay 5, Huang X, Lahiri D K, Rogers J T (2011) Novel drug targets based on metallobiology of Alzheimer's disease. Expert Opin Ther Targets 14: 1177-1197.
5. Duce J A, Tsatsanis A, Cater M A, James S A, Robb E, et al. (2010) Iron-export ferroxidase activity of beta-amyloid precursor protein is inhibited by zinc in Alzheimer's disease. Cell 142: 857-867.
6. Cho H H, Cahill C M, Vanderburg C R, Scherzer C R, Wang B, et al. (2010) Selective translational control of the Alzheimer amyloid precursor protein transcript by iron regulatory protein-I. J Biol Chem 285: 31217-31232.
7. Stys A, Galy B, Starzynski R R, Smuda E, Drapier J C, et al. (2011) Iron regulatory protein 1 outcompetes iron regulatory protein 2 in regulating cellular iron homeostasis in response to nitric oxide. J Biol Chem 286: 22846-22854.
8. Tucker S, Ahl M, Cho H H, Bandyopadhyay S, Cuny G D, et al. (2006) RNA Therapeutics Directed to the Non Coding Regions of APP mRNA, In Vivo Anti-Amyloid Efficacy of Paroxetine, Erythromycin, and N-acetyl cysteine. Cliff Alzheimer Res 3: 221-227.
9. Salehi A, Delcroix J D, Belichenko P V, Zhan K, Wu C, et al. (2006) Increased App Expression in a Mouse Model of Down's Syndrome Disrupts NGF Transport and Causes Cholinergic Neuron Degeneration. Neuron 51: 29-42.
10. Salehi A, Faizi M, Colas D, Valletta J, Laguna J, et al. (2009) Restoration of Norepinephrine-Modulated Contextrual memory in a Mouse Model of Down Syndrome. Science Translational Medicine 1: 1-9.
11. Granic A, Padmanabhan J, Norden M, Potter H (2012) Alzheimer Abeta peptide induces chromosome mis-segregation and aneuploidy, including trisomy 21: requirement for tau and APP. Mol Biol Cell 21: 511-520.
12. Hooli B V, Mohapatra G, Mattheisen M, Parrado A R, Roehr J T, et al. (2012) Role of common and rare APP DNA sequence variants in Alzheimer disease. Neurology 78: 1250-1257.
13. Rovclet-Lecrux A, Hannequin D, Raux G, Meur N L, Laquerriere A, et al. (2006) APP locus duplication causes autosomal dominant early-onset Alzheimer disease with cerebral amyloid angiopathy. Nat Genet 38: 24-26.
14. Perry G, Nunomura A, Hirai K, Zhu X, Perez M, et al. (2002) Is oxidative damage the fundamental pathogenic mechanism of Alzheimer's and other neurodegenerative diseases? Free Radic Biol Med 33: 1475-1479.
15. Smith C D, Carney J M, Starke-Reed P E, Oliver C N, Stadtman E R, et al. (1991) Excess brain protein oxidation and enzyme dysfunction in normal aging and in Alzheimer disease. Proc Natl Acad Sci USA 88: 10540-10543.
16. Butterfield D A (2012) Oxidative stress in Alzheimer disease: synergy between the Butterfield and Markesbery laboratories. Neuromolecular Med 13: 19-22.
17. Kwon O D, Khaleeq A, Chan W, Pavlik V N, Doody R S (2012) Apolipoprotein E polymorphism and age at onset of Alzheimer's disease in a quadriethnic sample. Dement Geriatr Cogn Disord 30: 486-491.
18. Wisniewski T, Castano E M, Golabek A, Vogel T, Frangione B (1994) Acceleration of Alzheimer's fibril formation by apolipoprotein E in vitro. Am J Pathol 145: 1030-1035.
19. Nilsson L N, Arendash G W, Leighty R E, Costa D A, Low M A, et al. (2004) Cognitive impairment in PDAPP mice depends on ApoE and ACT-catalyzed amyloid formation. Neurobiol Aging 25: 1153-1167.
20. McNaughton D, Knight W, Guerreiro R, Ryan N, Lowe J, et al. (2012) Duplication of amyloid precursor protein (APP), but not prion protein (PRNP) gene is a significant cause of early onset dementia in a large U K series. Neurobiol Aging 33: 426 e413-421.
21. Bandyopadhyay S, Ni J, Ruggiero A, Waishe K, Rogers M S, et al. (2006) A high-throughput drug screen targeted to the 5'untranslated region of Alzheimer amyloid precursor protein mRNA. J Biomol Screen 11: 469-480.
22. Kuo Y M, Li Z, Jiao Y, Gaborit N, Pani A K, et al. (2010) Extensive enteric nervous system abnormalities in mice transgenic for artificial chromosomes containing Parkinson disease-associated alpha-synuclein gene mutations precede central nervous system changes. Hum Mol Genet 19: 1633-1650.
23. Ray B, Bailey J A, Sarkar S, Lahiri D K (2009) Molecular and immunocytochemical characterization of primary neuronal cultures from adult rat brain: Differential expression of neuronal and glial protein markers. J Neurosci Methods 184: 294-302.
24. Kurogi Y, Miyata K, Okamura T, Hashimoto K, Tsutsumi K, et al. (2001) Discovery of novel mesangial cell proliferation inhibitors using a three-dimensional database searching method. J Med Chem 44: 2304-2307.
25. Gilman C P, Chan S L, Guo Z, Zhu X, Greig N, et al. (2003) p53 is present in synapses where it mediates mitochondrial dysfunction and synaptic degeneration in response to DNA damage, and oxidative and excitotoxic insults. Neuromolecular Med 3: 159-172.
26. Schulz W G, Nieman R A, Skibo E B (1995) Evidence for DNA phosphate backbone alkylation and cleavage by pyrrolo{1,2-a]benzimidazoles: small molecules capable of causing base-pair-specific phosphodiester bond hydrolysis. Proc Natl Aead Sei USA 92: 11854-11858.
27. Mikkilineni 5, Cantuti-Castelvetri 1, Cahill C M, Balliedier A, Greig N H, et al. (2012) The anticholinesterase phenserine and its enantiomer posiphen as 5'untranslated-region-directed translation blockers of the Parkinson's alpha synuclein expression. Parkinsons Dis 2012: 142372.
28. Goforth J13, Anderson S A, Nizzi C P, Eisenstein R S (2010) Multiple determinants within iron-responsive elements dictate iron regulatory protein binding and regulatory hierarchy. Rna16: 154-169.
29. Singh A, Kong Q, Luo X, Petersen R B, Meyerson H, et al. (2009) Prion protein (PrP) knock-out mice show altered iron metabolism: a functional role for PrP in iron uptake and transport. PLoS One 4: e6115.
30. Wolk D A, Klunk W (2009) Update on amyloid imaging: from healthy aging to Alzheimer's disease. Curr Neurol Neurosci Rep 9: 345-352.
31, Mathis C A, Wang Y, Holt D P, Huang G F, Debnath M L, et al. (2003) Synthesis and evaluation of 11C-labeled 6-substituted 2-arylbenzothiazoles as amyloid imaging agents, J Med Chem 46:2740-2754.
32. Rogers J T, Mikkilineni 5, Cantuti-Castelvetri I, Smith D H, et al. (2011) The alpha-synuclein 5'untranslated region targeted translation blockers: anti-alpha synuclein efficacy of cardiac glycosides and Posiphen, J Neural Transm 118: 493-507.
31 Lahiri D K, Chen D, Maloney B, Holloway H W, Yu Q S, et al. (2007) The experimental Alzheimer's disease drug posiphen [(+)-phenserinej lowers amyloid-beta peptide levels in cell culture and mice. J Pharmacol Exp Ther 320: 386-396.
34. Maccecchini M Roffman M, Greig N H (2009) Posiphen lowers amyloid precursor protein and amyloid j3 as well as acetylcholinesterase levels in culture, animals and humans Alzheimer's & Dementia 5(45): 47-48.
35. Donahue C P, Ni J, Rozners E, Glicksman M A, Wolfe M S (2007) Identification of tau stem loop RNA stabilizers, J Biomol Screen 12: 789-799.
36. Iijima K, Gatt A, Iijima-Ando K (2013) Tau Ser262 phosphorylation is critical for Abeta42-induced tau toxicity in a transgenic Drosophila model of Alzheimer's disease. Hum Mol Genet 19: 2947-2957.
37, Werstuck G, Green, M R (1998) Controlling gene expression in living cells through small molecule-RNA interactions. Science 282: 296-298.
38. Lancaster A M, Jan E, Sarnow P (2006) Initiation factor-independent translation mediated by the hepatitis C virus internal ribosome entry site. Rna 12: 894-902.
39. Tibodeau J D, Fox P M, Ropp P A, Theil E C, Thorp H H (2006) The up-regulation of ferritin expression using a small-molecule ligand to the native mRNA, Proc Natl Acad Sci USA 103: 253-257.
40. Venti A, Giordano T, Eder P, Lahiri D K, Greig N H, et al. (2004) The Integrated Role of Desferrioxamine and Phenserine Targeted to an Iron-Responsive Element in the APP-mRNA 5t-Untranslated Region. Ann N Y Acad Sci 1035: 34-48.
41. Morse L I, Payton S M, Cuny G D, Rogers J T (2004) FDA-Preapproved Drugs Targeted to the Translational Regulation and Processing of the Amyloid Precursor Protein. J Mel Neurosci 24: 129-136.
42. Shaw K T, Utsuki T, Rogers J, Yu Q S, Sambamurti K, et al. (2001) Phenserine regulates translation of beta-amyloid precursor protein mRNA by a putative interleukin-1 responsive element, a target for drug development. Proc Natl Acad Sci USA 98: 7605-7610.
43. Utsuki T, Yu Q S, Davidson D, Chen D, Holloway H W, et al. (2006) Identification of novel small molecule inhibitors of amyloid precursor protein synthesis as a route to lower Alzheimer's disease amyloid-beta peptide. J Pharmacol Exp Ther 318: 855-862.
44, Skibo E B, Islam I, Heileman M J, Schulz W G (1994) Structure-activity studies of benzimidazole-based DNA-cleaving agents. Comparison of benzimidazole, pyrrolobenzimidazole, and tetrahydropyridobenzimidazole analogues. J Med Chem 37: 78-92.
45. Donahue C P, Muratore C, Wu J Y, Kosik K S, Wolfe M S (2006) Stabilization of the tau exon 10 stem loop alters pre-mRNA splicing. J Biol Chem 281: 23302-23306.
46. Hamy F, Felder E R, Heizmann G, Lazdins J, Aboul-ela F, et al. (1997) An inhibitor of the Tat/TAR RNA interaction that effectively suppresses HIV-1 replication. Proc Natl Acad Sci USA 94: 3548-3553.
47. Singh A, Isaac A O, Luo X, Mohan M L, Cohen M L, et al. (2009) Abnormal brain iron homeostasis in human and animal priori disorders. PLoS Pathog 5: e1000336.
48. Morales R, Estrada L D, Diaz-Espinoza R, Morales-Scheihing D, Sara M C, et al. (2012) Molecular cross talk between misfolded proteins in animal models of Alzheimer's and prion diseases. J Neurosci 30: 4528-4535.
49. Friedlich A L, Tanzi R E, Rogers J T (2007) The 5'-untranslated region of Parkinson's disease alpha-synuclein messenger RNA contains a predicted iron responsive element. Mol Psychiatry 12: 222-223.

Example 2: Characterization of Several RNA Intercalators that Limit Translation Conferred by the '5 Untranslated Region JTR-009 likely intercalates directly into bases stacked to form the RNA stem loop encoded by APP IRE sequences, and thereby permanently substitutes for Fe-inducible binding of IRP1 to the APP 5'UTR (Kd, 30 µM). This class of intercalator was found to be 50 fold more potent to block APP translation than posiphen and NAC. JTR-009 can be readily tested to in vivo slow ribosome scanning of the APP 5'UTR and limit APP translation (Aβ) as a therapy for DS individuals who express an extra copy of the APP gene and exhibit increased AD-like amyloidosis and dementia (Bandyopadhyay et al., 2006).

Ten close commercial analogs of JTR-009, chosen from chemical structures predicted to improve its potency for blocking APP translation and bioavailability, are characterized by Formulas II-XI. These commercial analogs, as well as JTR-009, BL-1 and other compounds of Formulas A-D, can be tested for their capacity to limit translation of APP, to thus favorably reduce Aβ levels in B6-R1:40 mice. B6-R1: 40 mice is a unique mouse model of DS that expresses all the chromosome 16 APP isoforms under the translational control of the complete human APP 5'UTR. The top agents should reset oxidative iron balance resulting from APP over-expression and thus increased ferroportin-dependent iron export from DS neurons.

Steps for investigating the ex vivo potency/mechanism of action of a compound that blocks APP translation via the APP 5'UTR RNA target include:

1. Establish the potency of the compound to inhibit APP expression and limit Aβ production using (IC-50) in primary cortical E-18 neurons from B6-R1:40 mice (http://jaxmice-.jax.org/strain/005300.html). Quantitative western blots can be used to measure levels of APP relative to that of compensatory APLP-1/-2 to assure drug specificity. B6-R1:40 cortical neurons provide sufficiently high Aβ expression within the sensitivity range of the ELISAs that are routinely ran to confirm anti-Aβ efficacy (Biosource, int.). Cell viability can be checked by MTS staining for intracellular mitochondrial viability and use LDH levels to check cell membrane integrity. For these assays both NAC and posiphen are employed as positive controls as well-characterized APP 5'UTR directed translation blockers.

2. Employ RNA gel shift assays to profile how each APP 5'UTR blocker limits rates of APP translation as correlated with changed IRP1 binding to the APP 5'UTR. These experiments can be conducted in dose-responsive and time-course format to determine if the pattern of IRP1/2 translational repression of APP and ferritin in primary neurons is the same as for SH-SY5Y cells. Biotinylated RNA pull-down assays were previously employed to measure the drug-induced changes to the binding constant between IRP1 and the IREs encoded by H-ferritin and APP mRNAs (Cho et al., 2010). [Scatchard analysis: the binding Kd for APP IRE to rIRP1=30 pM and Kd for H-ferritin-IRE to rIRP-1=40 pM, as benchmarked to reproduce the known interactions between IRP1/IRP2 with the ferritin-H IRE by RNA gel-shifts (Cho et al., 2010)].

3. Measure the extent to which a compound influences iron homeostasis and thus neuronal viability in B6-R1:40 cortical neurons. Calcein staining can determine intracellular iron levels and the extent to which neuronal exposure to the compound alters intracellular REDOX-active iron correlated to protein carbonylation as an indicator of oxidative stress in cultured neurons (Duce et al., 2010). Neuronal viability is routinely assessed by flurojade staining of neurons.

Figure 9:
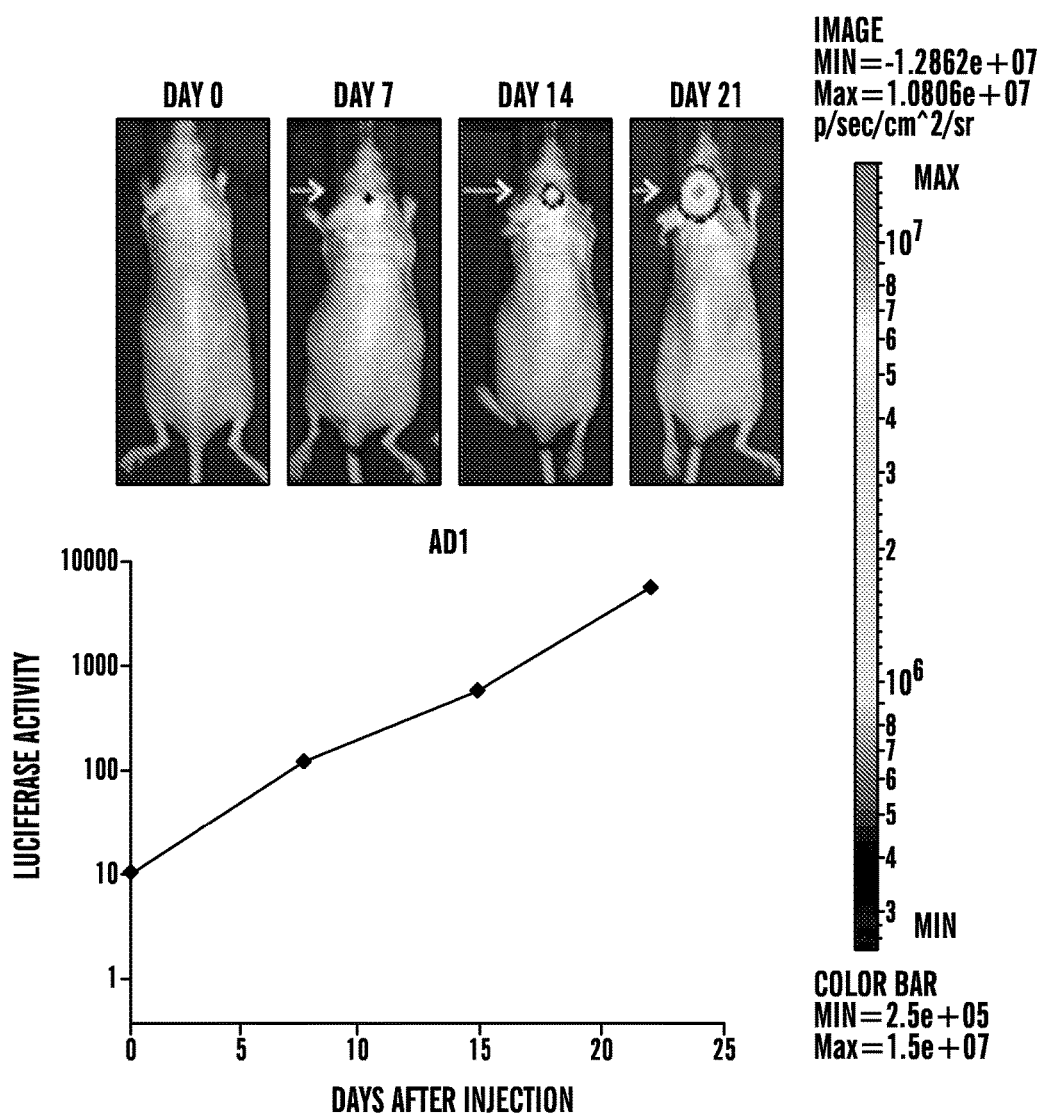
FIG. 9 shows bioluminescence imaging of APP 5'UTR conferred translation of a luciferase reporter gene. Shown are images of brain immunoluminescence recorded in typical nude mouse intracrannially injected (frontal cortex) with human SH-SY5Y cells stably transfected with APP 5'UTR-Luc mRNA plasmid ($2\times10^5$ cells in 2 μL PBS). The arrows show APP translation via its 5'UTR of mRNA using luciferase as the reporter. This was imaged at day 7, 14, and 21, using an IVIS 100 Bioluminescence Imaging System (Xenogen, Caliper Life Science, Inc.). By day 7 there is sufficient luciferase expression in the mouse brain to permit its use to monitor APP 5'UTR directed inhibitors (co-administered day-7 till 21). Technical specifications: Resolution<0.2 mm; Imaging size>1024×1024; and Field of View 10×10 cm to 25×25 cm.

4. Use the in vivo/ex vivo coupled bioluminescence imaging method developed by the inventors for monitoring real time APP 5'UTR conferred gene expression (FIG. 9). This method can serve to optimize a dosing regimen of the compound for the best conditions to inhibit APP 5'UTR-luciferase expression in vivo. APP 5'UTR blockers were routinely administered to mice by oral gavage at 0, 2.5, 5, 20, 35, 50, and 65 mg/kg/day. After 21 days and a further three days drug treatment, one can monitor the capacity of APP 5'UTR blockers to limit luciferase expression using a readout from a small animal bioluminescence scanner (Xenogen, inc.). This in vivo bioluminescence detection of APP 5'UTR inhibition analysis is routinely conducted to establish the relative in vivo pharmacokinetics of the compound to enter into the brain. These events are recorded and compared with absorption of JTR-009 by mass spectroscopy and HPLC to determine the optimal administration into B6-R1: 40 DS mice for the in vivo experiments.

Selected age and sex matched cohorts of B6-R1.40 mice are employed to assess in vivo the anti-amyloid efficacy of a compound that blocks APP translation (e.g., a compound of Formulas A-D, or I-XII) relative to posiphen and NAC. Power analysis showed B6-R1.40 mice as young as two months of age can detect a 20% decrease in Aβ levels (p=0.05) (n=12). The capacity of the compound is assessed to block Aβ using B6-R1.40 mice beginning before the age when they exhibit clear plaque deposition (~12 months). The mice are treated for 12 weeks from 11-14 months (see refs (Komarova et al., 2003; Lahiri et al., 2007) with a dosing regimen (Table 3).

TABLE 3

Treatments of B6-R1.40 mice with APP translation blockers

| Treatment | Duration | Outcome | Fe homeostasis | Viability/ specificity | Cognition |
|---|---|---|---|---|---|
| Placebo | 11-14 months | Aβ & APP | IRP1/APPI RE | APLP-1-2/β-actin | 13 mo |
| JTR-009 | 11-14 months | Aβ & APP | IRP1/APP IRE | APLP-1-2/β-actin | 13 mo |
| Posiphen | 11-14 months | Aβ & APP | IRP1/APP IRE | APLP-1-2/β-actin | 13 mo |
| Analog of JTR-009 | 11-14 months | Aβ & APP | IRP1 APP IRE | APLP-1-2/β-actin | 13 mo |
| NAC | 11-14 months | Aβ & APP | IRP1/APP IRE | APLP-1-2/β-actin | 13 mo |

In Table 3, mice are divided (n=12 mice/cohort) (Tucker et al., 2006). Mice are administered 3 months treatment with optimally formulated JTR-009, NAC and posiphen (positive controls). Outcomes: Staining with APP antibody CT15 for APP and CTFs/dystrophic neuritis, Aβ-40, Aβ-42 by benchmarked Aβ ELISA. The following are the outcome measures of in vivo APP 5'UTR inhibition:

1. Microscopic analysis of brain amyloid. Thioflavine stain of left hemispheres (Aβ stain of right hemispheres).
2. Quantitative APP specific western blotting with 22C11/A8717 antibodies are compared to matched qRTPCR data in order to characterize the efficacy reduce translation of APP mRNA.
3. Immunohistochemical determination of neuronal viability after NeuroJade staining. The relative extent to which APP 5'UTR blockers rescue DS neurons from entry into premature mitotic cell cycle events (CCEs) is tested. Notably, R1.40 mice exhibit neuronal CCEs 6-8 months before detectable amyloid beta deposition; thus limiting APP translation should reduce dose of APP processing products that cause CCE neuronal death (Varvel et al., 2008).
4. Behavioral tests for cognitive function by Y-maze and Water maze.
5. Measure the capacity of APP 5'UTR blockers to adjust iron balance. JTR-009, NAC and posiphen treatments are assessed to determine how they may enhance neural viability by resetting IRP1/IRP2 mediated translation of both ferroportin and L- and H-chain ferritin mRNAs thus to restore iron homeostasis. This is measured from harvested brain tissue using the techniques as described. In accord, increased REDOX-active iron in liver and brain is assessed for potentially significant increased protein carbonylation, as indeed occurs in APP knockout mice when fed high iron diets (ANOVA+Dunnett's T post hoc tests) (Duce et al., 2010).

What is claimed is:

1. A method of treating a neurodegenerative disorder in a subject, the method comprising administering to the subject in need thereof an effective amount of a compound selected from compounds of Formulas I-XII, or a pharmaceutically acceptable salt thereof:

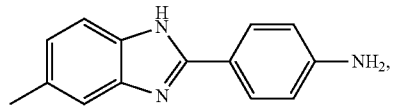

Formula I

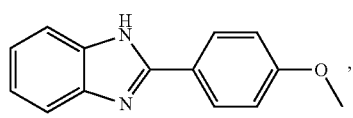

Formula II

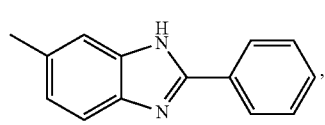

Formula III

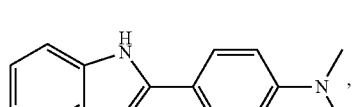

Formula IV

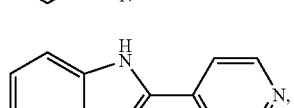

Formula V

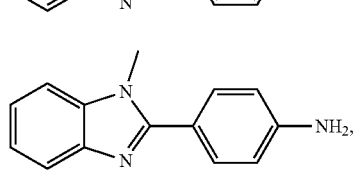

Formula VI

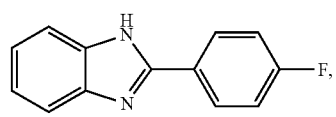

Formula VII

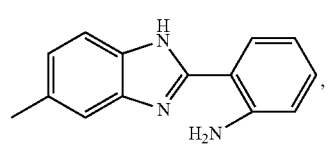

Formula VIII

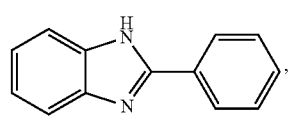

Formula VIIII

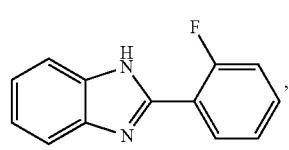

Formula X

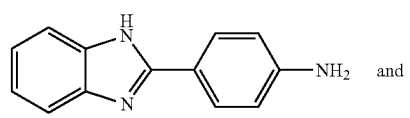

Formula XI

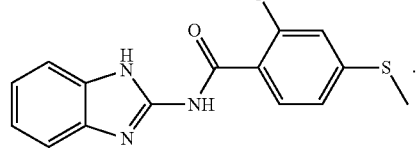

Formula XII

2. The method of claim 1, wherein the compound is a compound of Formula I or XII, or a pharmaceutically acceptable salt thereof.

3. The method of claim 1, wherein the neurodegenerative disorder is selected from the group consisting of Alzheimer's disease, Down syndrome, Parkinson's disease, Huntington's Disease, Amyotrophic Lateral Sclerosis (also termed Lou Gehrig's disease) and Multiple Sclerosis.

4. The method of claim 3, wherein the neurodegenerative disorder is Alzheimer's disease or Down syndrome.

5. The method of claim 1, wherein the subject is a mammal.

6. The method of claim 5, wherein the mammal is a human.

7. A method of decreasing amyloid-beta production in a subject's brain, the method comprising administering to the subject in need thereof an effective amount of a compound selected from compounds of Formulas I-XII, or a pharmaceutically acceptable salt thereof:

Formula I
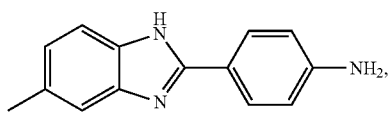

Formula II
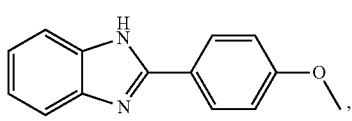

Formula III
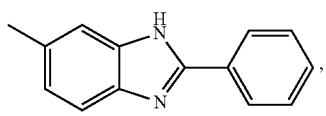

Formula IV
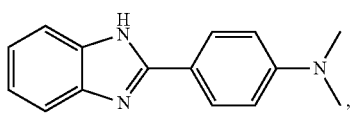

Formula V
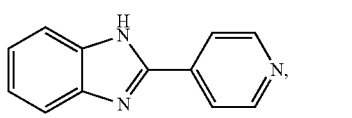

Formula VI
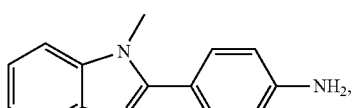

Formula VII
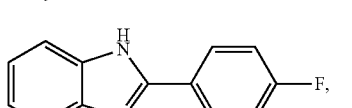

Formula VIII
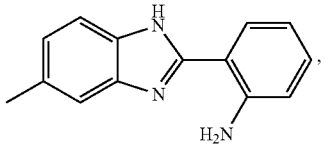

Formula VIIII
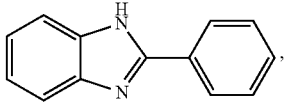

Formula X
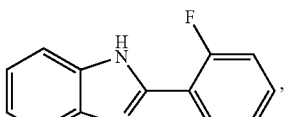

Formula XI
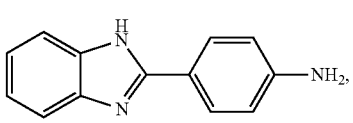

Formula XII
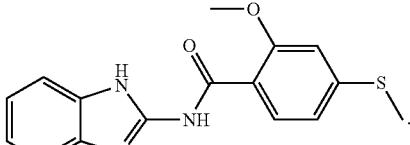

8. The method of claim 7, wherein the compound is a compound of Formula I or XII, or a pharmaceutically acceptable salt thereof.

9. The method of claim 7, wherein the subject is in need for treating a neurodegenerative disorder.

10. The method of claim 9, wherein the neurodegenerative disorder is selected from the group consisting of Alzheimer's disease, Down syndrome, Parkinson's disease, Huntington's Disease, Amyotrophic Lateral Sclerosis (also termed Lou Gehrig's disease) and Multiple Sclerosis.

11. The method of claim 10, wherein the neurodegenerative disorder is Alzheimer's disease or Down syndrome.

12. The method of claim 7, wherein the subject is a mammal.

13. The method of claim 12, wherein the mammal is a human.

14. The method of claim 7, wherein amyloid-beta is Aβ-42.

* * * * *